US012721825B2

(12) United States Patent
Tochtrop et al.

(10) Patent No.: US 12,721,825 B2
(45) Date of Patent: Sep. 1, 2026

(54) COMPOSITIONS AND METHODS FOR THE TREATMENT OF OCULAR DISORDERS

(71) Applicants: Case Western Reserve University, Cleveland, OH (US); The Regents of the University of California, Oakland, CA (US); The United States Government as Represented by the Department of Veteran Affairs, Washington, DC (US)

(72) Inventors: Gregory Tochtrop, Cleveland, OH (US); Philip Kiser, Cleveland, OH (US); Jianye Zhang, Cleveland, OH (US); Krzysztof Palczewski, Oakland, CA (US)

(73) Assignees: CASE WESTERN RESERVE UNIVERSITY, Cleveland, OH (US); THE REGENTS OF THE UNIVERSITY OF CALIFORNIA, Oakland, CA (US); THE UNITED STATES GOVERNMENT REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 411 days.

(21) Appl. No.: 18/263,758

(22) PCT Filed: Feb. 1, 2022

(86) PCT No.: PCT/US2022/014757

§ 371 (c)(1),
(2) Date: Aug. 1, 2023

(87) PCT Pub. No.: WO2022/165427

PCT Pub. Date: Aug. 4, 2022

(65) Prior Publication Data

US 2024/0122876 A1 Apr. 18, 2024

Related U.S. Application Data

(60) Provisional application No. 63/144,242, filed on Feb. 1, 2021.

(51) Int. Cl.
*A61K 31/137* (2006.01)

(52) U.S. Cl.
CPC .................................. *A61K 31/137* (2013.01)

(58) Field of Classification Search
CPC .................................................... A61K 31/137
See application file for complete search history.

(56) References Cited

U.S. PATENT DOCUMENTS 11,253,489 B2 * 2/2022 Palczewski ............. A61P 27/02
12,144,788 B2 * 11/2024 Palczewski .......... A61K 31/135

FOREIGN PATENT DOCUMENTS

WO WO 2018157129 * 8/2018

OTHER PUBLICATIONS

Pubchem, Substance Record for SID 38320868, Available Date: Dec. 5, 2007 [retrieved on Mar. 23, 2022].
C/D/N Isotopes Inc., Material Safety Data Sheet, Jan. 1, 2014 [retrieved on May 23, 2022).

* cited by examiner

*Primary Examiner* — Rei Tsang Shiao
(74) *Attorney, Agent, or Firm* — Tarolli, Sundheim, Covell & Tummino LLP

(57) ABSTRACT

A method of treating an ocular disorder in a subject in need thereof includes administering to the subject a therapeutically effective amount of a compound of formula (I) or a pharmaceutically acceptable salt, tautomer, or solvate thereof.

12 Claims, 9 Drawing Sheets

A

B emixustat, 24, 57, 58, 49, 59

C

D

E

A emixustat or
$^{2}H_{2}$-emixustat (58)

not observed

ACU-5201 or
$^{2}H_{1}$-ACU-5201

NOCV analyses

COMPOSITIONS AND METHODS FOR THE TREATMENT OF OCULAR DISORDERS

RELATED APPLICATION

This application claims priority from U.S. Provisional Application No. 63/144,242, filed Feb. 1, 2021, the subject matter of which is incorporated herein by reference in its entirety.

GOVERNMENT FUNDING

This invention was made with government support under 1904530 awarded by The National Science Foundation, and W81XWH-16-1-0699 awarded by The Department of Defense. The government has certain rights in the invention.

BACKGROUND

Retinal photoreceptor cells can respond to light throughout life because they continuously regenerate a light-sensitive chromophore and photoreceptor structures. Defects in various proteins involved in these processes cause photoreceptor degeneration. Light-detection is mediated by a group of G protein-coupled receptor proteins called opsins located in rod and cone photoreceptor cells of the retina. The light-absorbing chromophore of most vertebrate opsins is 11-cis-retinal. Absorption of a photon by an opsin pigment causes isomerization of the chromophore to all-trans-retinal. Regeneration of the visual chromophore following light exposure is dependent upon an enzymatic pathway referred to as the visual cycle.

To understand why human vision declines with age, considerable research has focused on the retina, especially the layer of rod and cone photoreceptor cells that convert light into electrical signals. However, age-related decreases in retinal photoreceptor cell function cannot be explained alone by rod/cone cell loss, abnormal retinal plasticity, or any acute signs of retinal disease. Rather, there are pathological events that take place over time, including the aberrant metabolism of all-trans-retinal that can interfere with normal photoreceptor function.

All-trans-retinal, when released from rhodopsin, primarily re-enters the visual cycle. However, in some individuals, it also can persist as an unbound potentially toxic aldehyde or react with other molecules to create toxic compounds such as N-retinylidene-N-retinylethanolamine (A2E) and retinal dimers. These events are thought to contribute to the etiology of blinding diseases such as age-related macular degeneration (AMD) and Stargardt disease.

Various therapeutic strategies have been developed to combat the aberrant metabolism of retinoids including all-trans-retinal. One of these involves the inhibition of the retinoid isomerase (RPE65), a key enzyme of the visual cycle, to slow the generating of all-trans-retinal without significantly impairing vision. Complete suppression of RPE65 activity, however, has undesirable blinding consequences, thus only attenuated or partial suppression of RPE65 is desirable. A second strategy is to lower the toxic effects of unbound all-trans-retinal and temporarily sequester it by adduction to a primary amine. Since most RPE65 inhibitors contain an amino group, they can play a dual role to both slow the metabolism of all-trans-retinal as well as sequester it.

SUMMARY

Embodiments described herein relate to compounds that include primary amines for use in the treatment of ocular disorders, such as ocular diseases and disorders related to aberrant all-trans-retinal accumulation in a subject's ocular tissue. It has been discovered that all-trans-retinal, a retinoid metabolite naturally produced during visual processing, is highly toxic when present at elevated levels. To lower its toxicity, therapeutic compounds that include primary amines have been identified in the Example below that can be delivered to and retained in the eye to modulate the visual (retinoid) cycle.

The compounds described herein have strategically incorporated deuterium and/or fluorine to modulate the compounds' potency and metabolism. Regioselective incorporation of fluorine can impact pKa modulation; alter target selectivity through conformational variations or changes in specific hydrophobic interactions; and alter tissue-specific penetration (e.g., central nervous system (CNS)), through modification of lipophilicity. These effects of fluorination are in addition to the well-established strategy of replacing metabolically labile hydrogens with C—F bonds. Regioselective incorporation of deuterium can be used to attenuate amine oxidation and rapid metabolic elimination via engineering a localized primary isotope effect. Collectively, the compounds have improved potency, absorption, selectivity, and metabolism to mitigate the toxicity of all-trans-retinal in age-related blindness.

In some embodiments, the compounds can have formula (I):

(I)

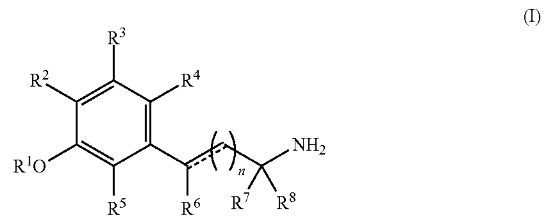

or be a pharmaceutically acceptable salt, tautomer, or solvate thereof;

wherein n is an integer from 0 to 6;

$R^1$ is a substituted or unsubstituted $C_1$-$C_{12}$ alkyl, $C_2$-$C_{12}$ alkenyl, $C_2$-$C_{12}$ alkynyl, $C_3$-$C_{12}$ aryl, heteroaryl, heterocyclyl, or $C_6$-$C_{12}$ alkaryl;

$R^2$, $R^4$, and $R^5$ are each independently H or F;

$R^3$ is H, F, or an alkyl or a fluoro alkyl group that includes at least three carbon atoms;

$R^6$ is H, $CH_3$, or OH;

$R^7$ and $R^8$ are H or D, wherein at least one of $R^7$ or $R^8$ is D if $R^2$, $R^4$, and $R^5$ are H; and the dashed line is an optional bond.

In some embodiments, at least one of $R^7$ or $R^8$ is D. For example, both of $R^7$ and $R^8$ can be D.

In some embodiments, at least one of $R^2$ or $R^5$ is F. For example, $R^2$ can be F.

In other embodiments, $R^1$ is selected from the group consisting of:

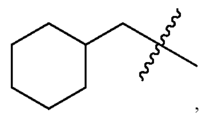

,

-continued

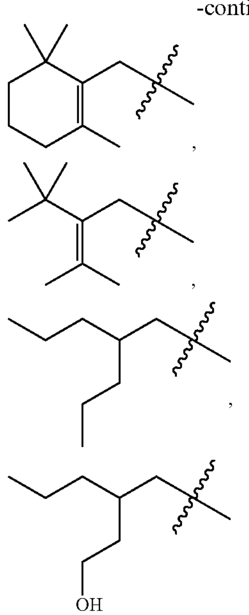

and fluoro derivatives thereof. For example, $R^1$ can be selected from the group consisting of:

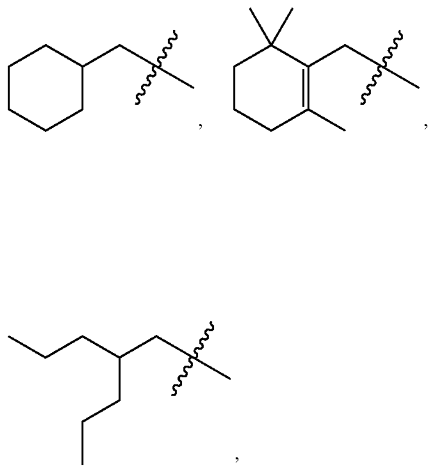

and fluoro derivatives thereof.

In some embodiments, $R^3$ is a branched or cyclic $C_3$-$C_{24}$ alkyl or fluoroalkyl. For example, $R^3$ can be selected from the group consisting of:

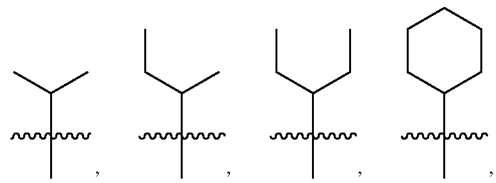

and fluoro derivatives thereof.

In other embodiments, the compound can have formula (II):

(II)

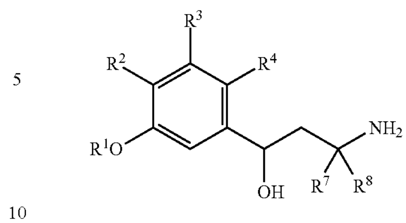

or be a pharmaceutically acceptable salt, tautomer, or solvate thereof;

wherein $R^1$ is a substituted or unsubstituted $C_1$-$C_{12}$ alkyl, $C_2$-$C_{12}$ alkenyl, $C_2$-$C_{12}$ alkynyl, $C_3$-$C_{12}$ aryl, heteroaryl, heterocyclyl, or $C_6$-$C_{12}$ alkaryl;

$R^2$ and $R^4$ are each independently H or F;

$R^3$ is H, F, or an alkyl or a fluoro alkyl group that includes at least three carbon atoms; and $R^7$ and $R^8$ are H or D, wherein at least one of $R^7$ or $R^8$ is D if $R^2$ and $R^4$ are H.

In some embodiments, at least one of $R^7$ or $R^8$ is D. For example, both of $R^7$ and $R^8$ can be D.

In some embodiments, $R^2$ can be F.

In other embodiments, $R^1$ is selected from the group consisting of:

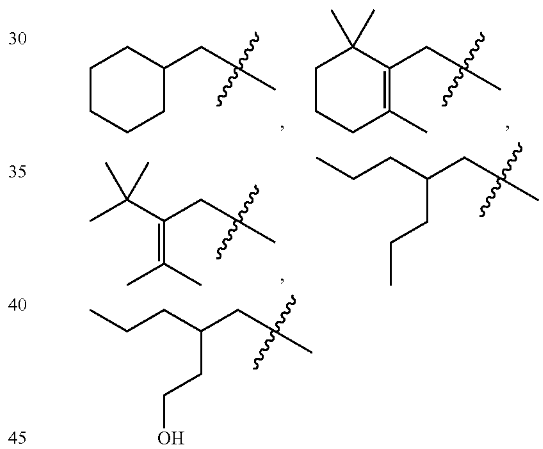

and fluoro derivatives thereof. For example, $R^1$ can be selected from the group consisting of:

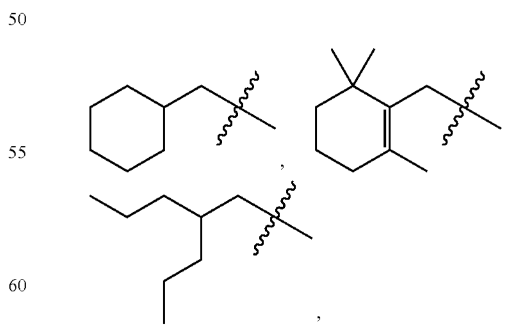

and fluoro derivatives thereof.

In some embodiments, $R^3$ is a branched or cyclic $C_3$-$C_{24}$ alkyl or fluoroalkyl. For example, $R^3$ can be selected from the group consisting of:

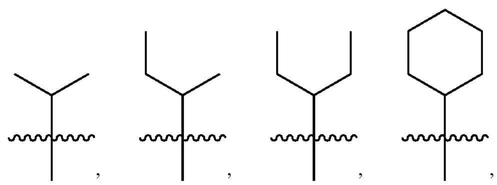

and fluoro derivatives thereof.

In still other embodiments, the compound can have formula (III):

(III)

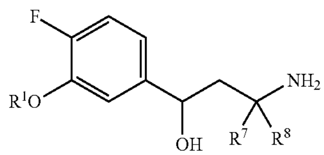

or be a pharmaceutically acceptable salt, tautomer, or solvate thereof;

wherein $R^1$ is a substituted or unsubstituted $C_1$-$C_{12}$ alkyl, $C_2$-$C_{12}$ alkenyl, $C_2$-$C_{12}$ alkynyl, $C_3$-$C_{12}$ aryl, heteroaryl, heterocyclyl, or $C_6$-$C_{12}$ alkaryl; and $R^7$ and $R^8$ are H or D.

In some embodiments, at least one of $R^7$ or $R^8$ is D. For example, both of $R^7$ and $R^8$ can be D.

In some embodiments, $R^1$ is selected from the group consisting of:

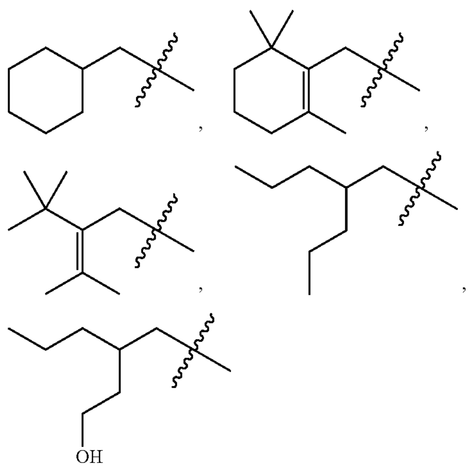

and fluoro derivatives thereof. For example, $R^1$ can be selected from the group consisting of:

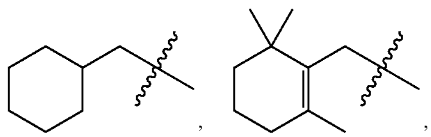

-continued

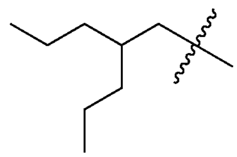

and fluoro derivatives thereof.

In other embodiments, the compound can formula (IV):

(IV)

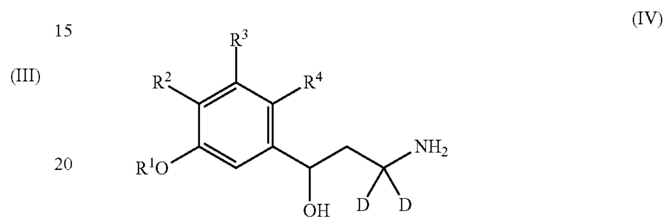

or be a pharmaceutically acceptable salt, tautomer, or solvate thereof;

wherein $R^1$ is a substituted or unsubstituted $C_1$-$C_{12}$ alkyl, $C_2$-$C_{12}$ alkenyl, $C_2$-$C_{12}$ alkynyl, $C_3$-$C_{12}$ aryl, heteroaryl, heterocyclyl, or $C_6$-$C_{12}$ alkaryl;

$R^2$ and $R^4$ are each independently H or F; and $R^3$ is H, F, or an alkyl or a fluoro alkyl group that includes at least three carbon atoms.

In some embodiments, $R^2$ can be F.

In other embodiments, $R^1$ is selected from the group consisting of:

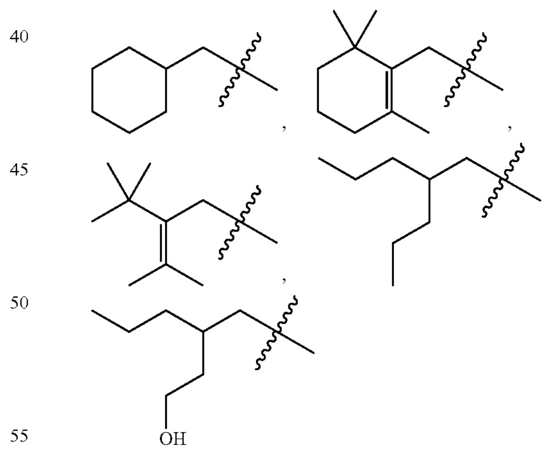

and fluoro derivatives thereof. For example, $R^1$ can be selected from the group consisting of:

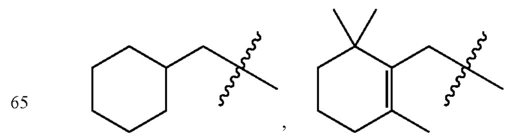

-continued

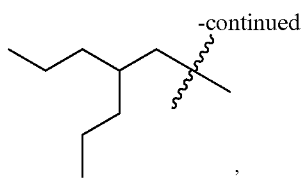

, and fluoro derivatives thereof.

In some embodiments, $R^3$ is a branched or cyclic $C_3$-$C_{24}$ alkyl or fluoroalkyl. For example, $R^3$ can be selected from the group consisting of:

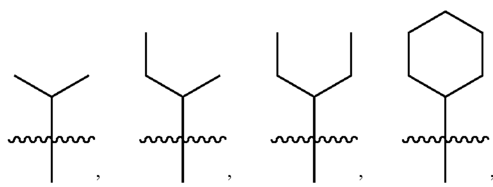

and fluoro derivatives thereof.

In other embodiments, the compound can have formula (V):

(V)

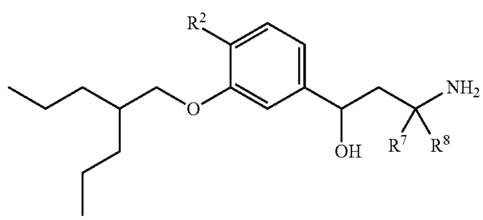

or be a pharmaceutically acceptable salt, tautomer, or solvate thereof;

wherein $R^2$ is H or F; and $R^7$ and $R^8$ are each independently H or D, and wherein at least one of $R^7$ or $R^8$ is D if $R^2$ is H.

In some embodiments, at least one of $R^7$ or $R^8$ is D. For example, both of $R^7$ and $R^8$ can be D.

In other embodiments, $R^2$ can be F.

In other embodiments, the compound can have formula (VI):

(VI)

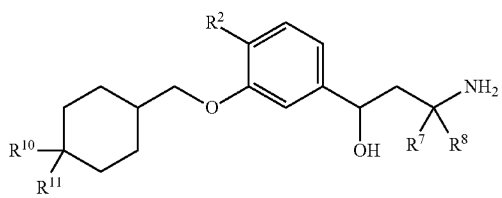

or be a pharmaceutically acceptable salt, tautomer, or solvate thereof;

wherein $R^2$ is H or F;

$R^7$ and $R^8$ are each independently H or D, and wherein at least one of $R^7$ or $R^8$ is D if $R^2$ is H; and $R^{10}$ and $R^{11}$ are each independently H or F.

In some embodiments, at least one of $R^7$ or $R^8$ is D. For example, both of $R^7$ and $R^8$ can be D.

In some embodiments, $R^2$ is F.

In other embodiments, the compound can be selected from:

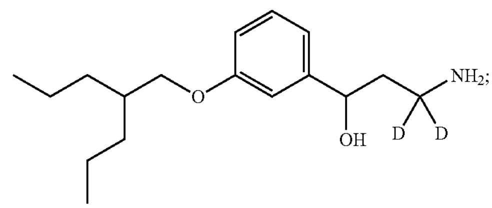

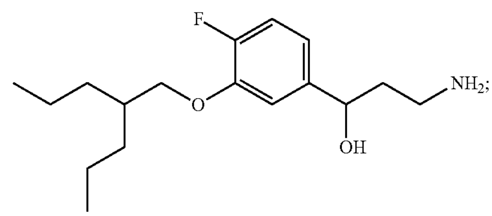

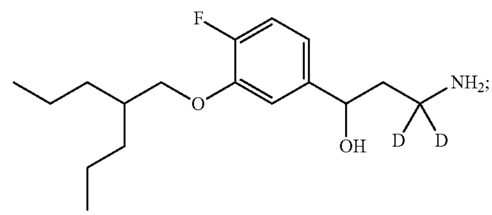

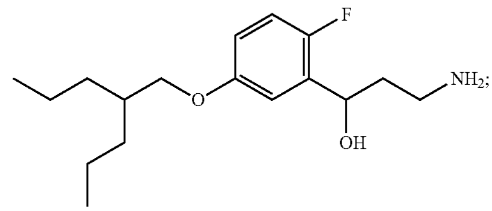

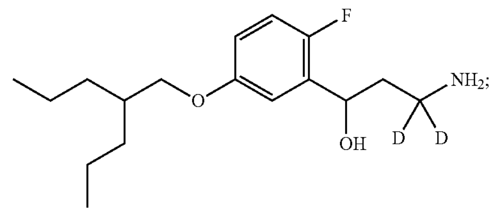

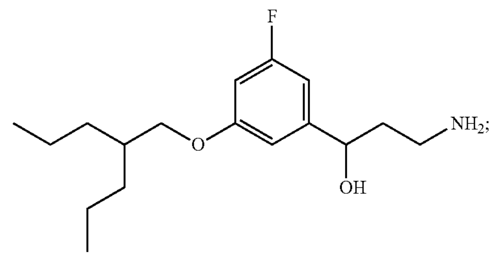

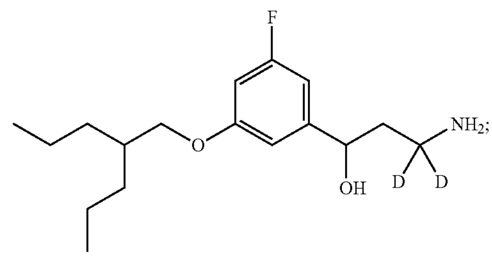

-continued
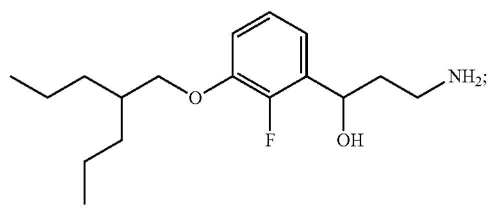
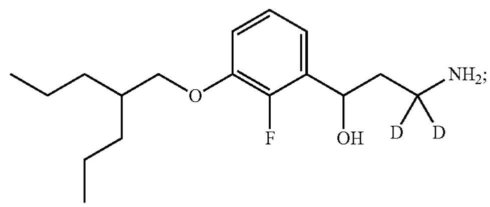
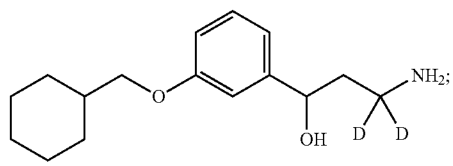
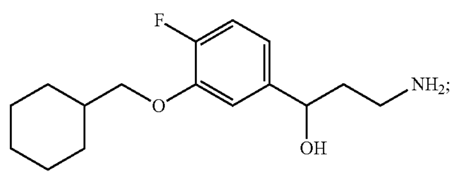
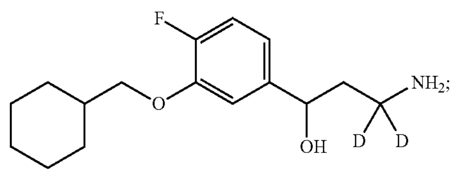
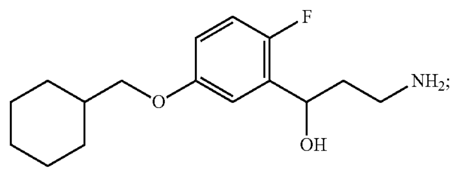
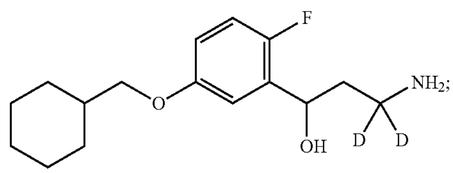
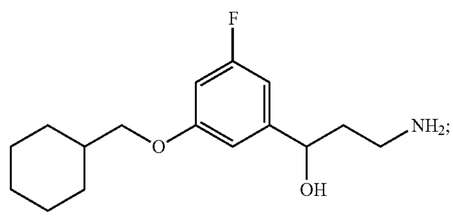
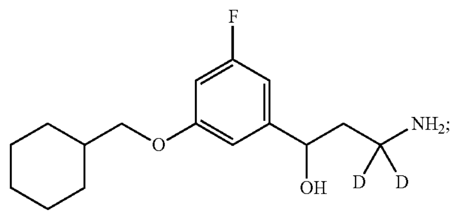
-continued
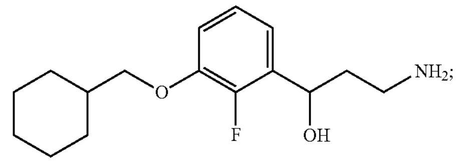
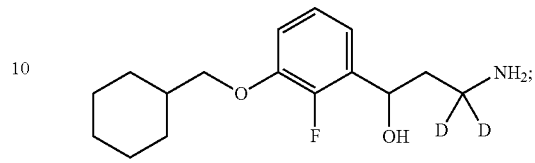
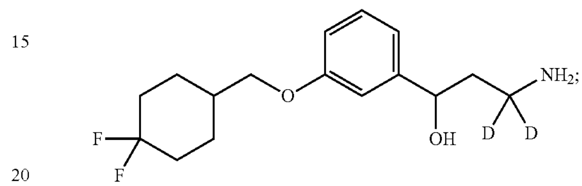
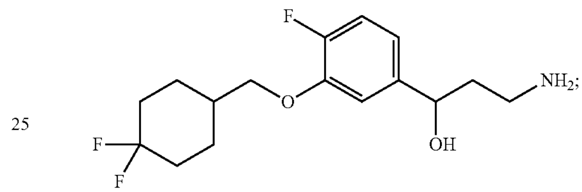
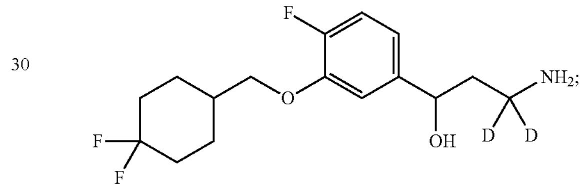
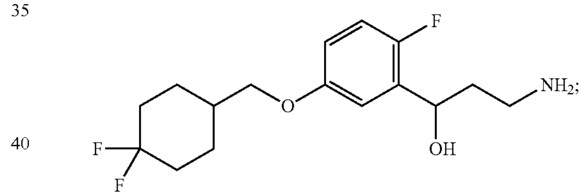
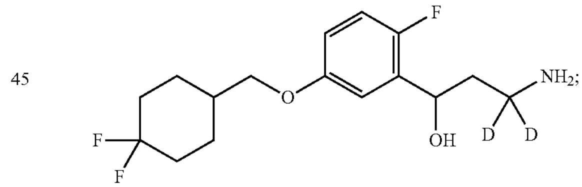
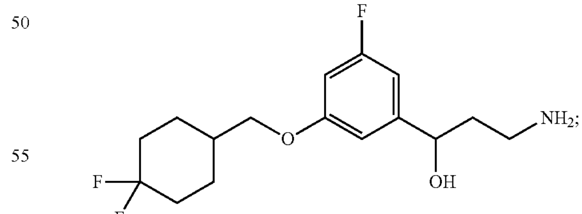
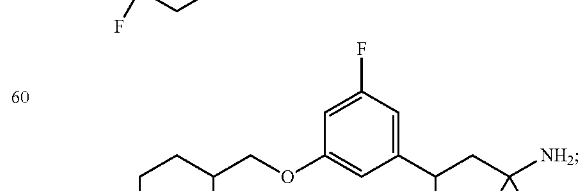
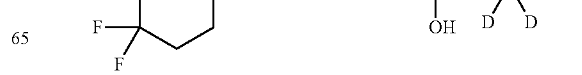

-continued

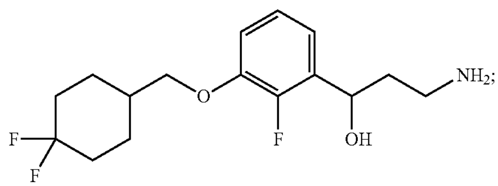

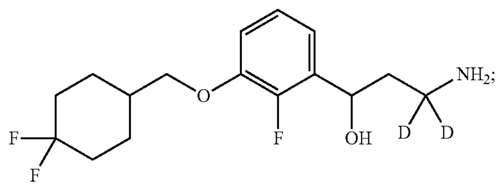

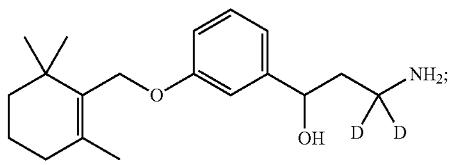

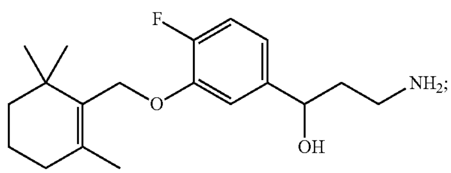

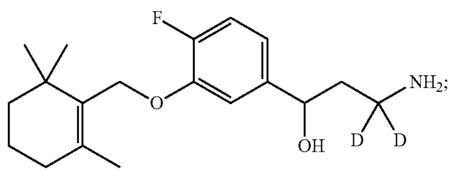

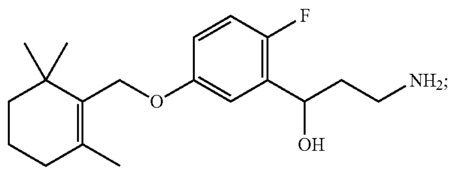

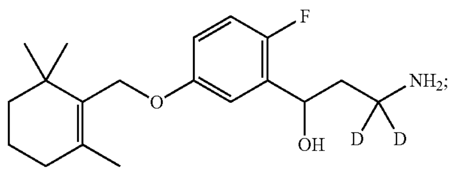

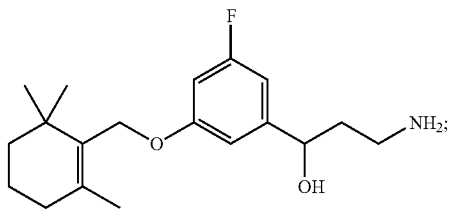

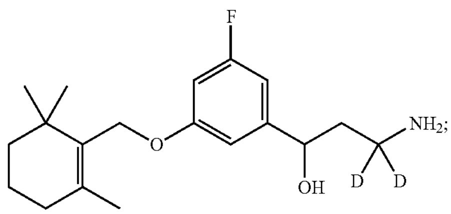

-continued

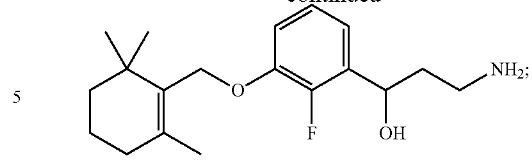

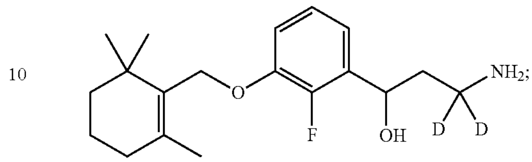

or a pharmaceutically acceptable salt, tautomer, or solvate thereof.

In some embodiments, the compound upon administration to a subject transiently sequesters all-trans-retinal in ocular tissue of the subject by forming a reversible Schiff-base with the all-trans-retinal. The compound does not adversely affect normal retinoid cycle performance.

In some embodiments, the compound can inhibit RPE65 enzymatic activity in the subject.

In some embodiments, the compound can be delivered to the subject by at least one of topical administration, systemic administration, intravitreal injection, and intraocular delivery.

In some embodiments, the compound can be provided in an ocular preparation for sustained delivery.

In other embodiments, a therapeutically effective amount of a compound described herein can be administered to a subject in need thereof to treat an ocular disorder. The ocular disorder can include at least one of light induced retinal degeneration, macular degeneration, Stargardt's disease, geographic atrophy, and retinitis pigmentosa.

In some embodiments, the compound does not cause night blindness in the subject.

Other embodiments described herein relate to a pharmaceutical composition that includes a pharmaceutically acceptable carrier and a compound selected from:

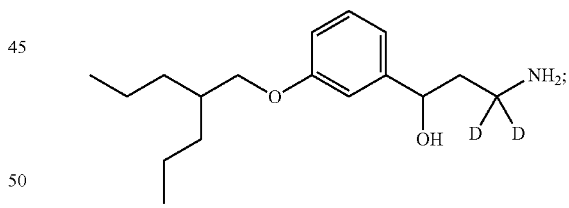

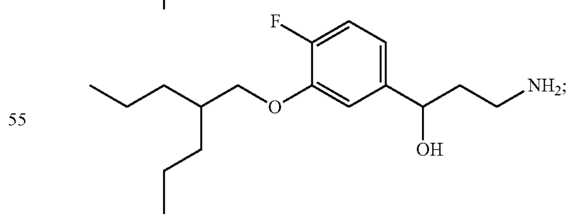

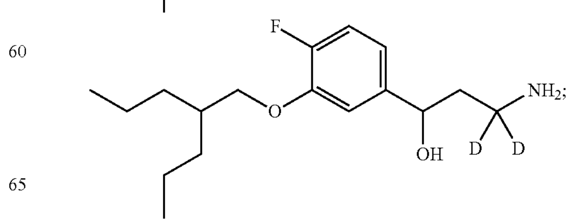

-continued
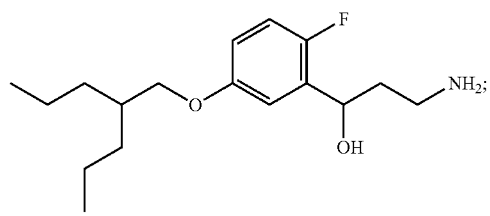
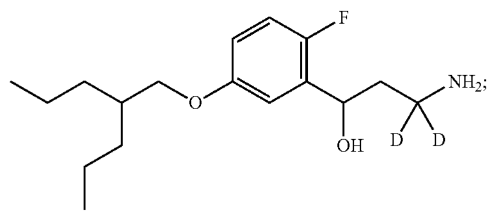
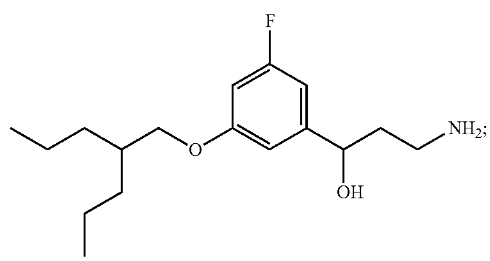
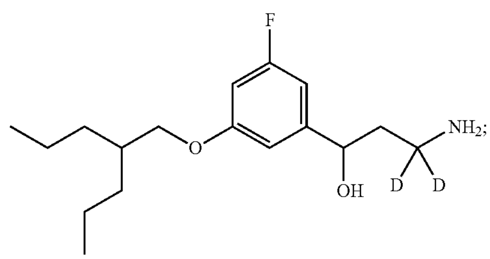
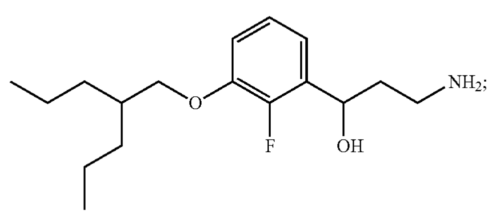
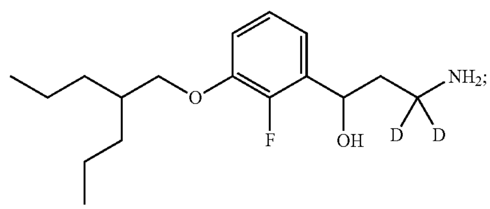
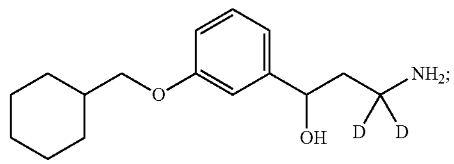
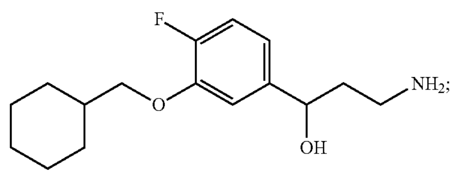
-continued
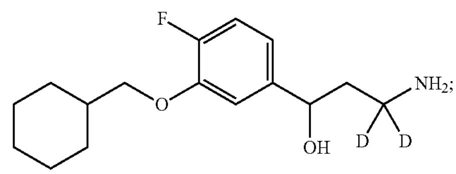
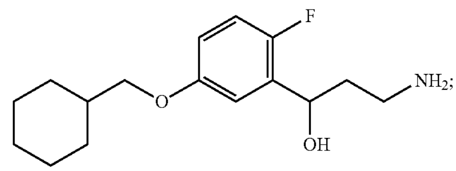
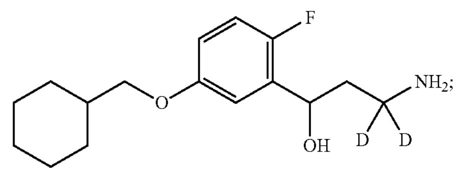
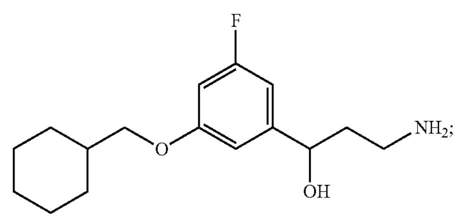
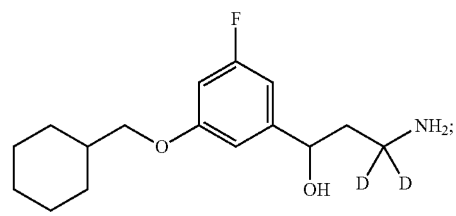
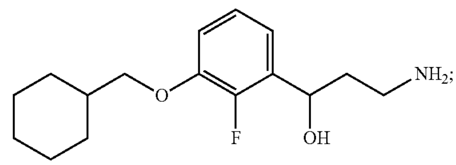
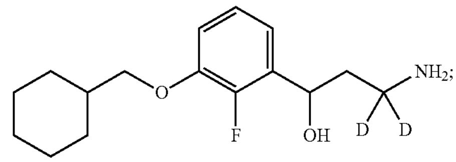
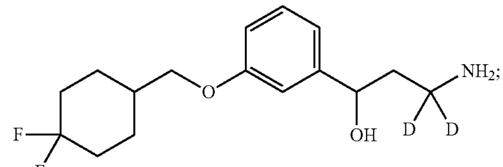
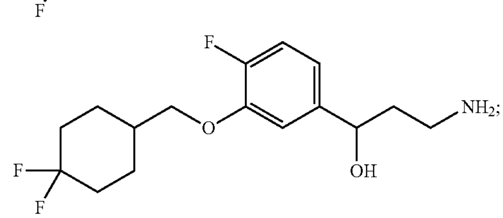

-continued

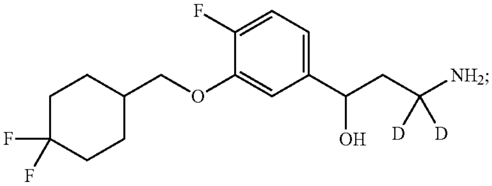

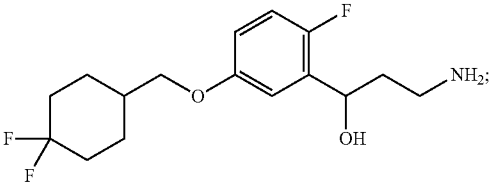

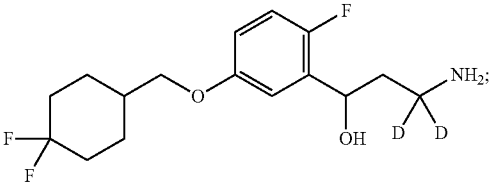

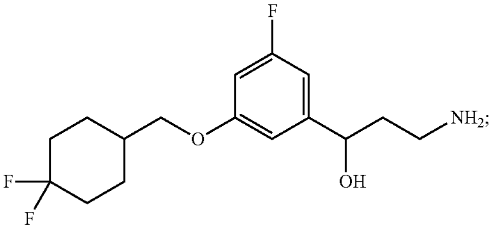

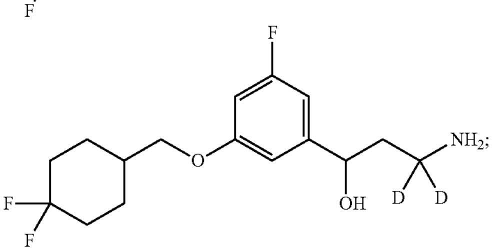

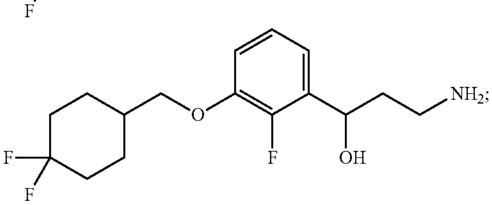

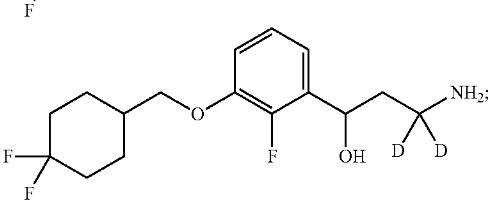

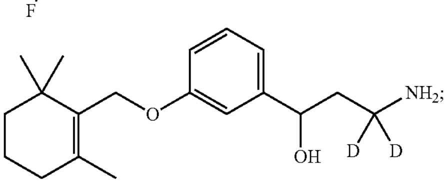

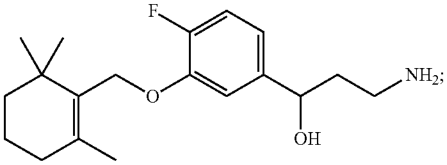

-continued

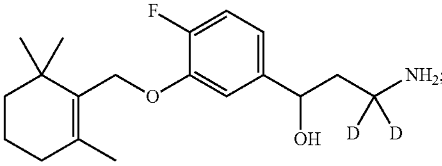

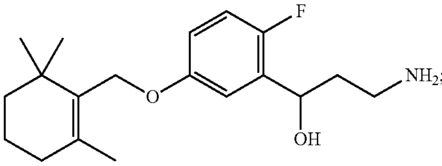

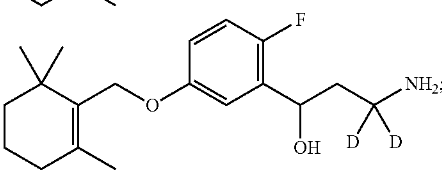

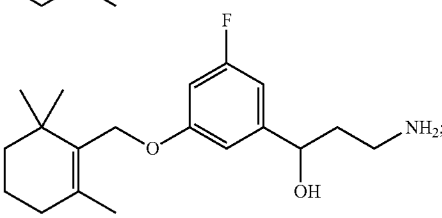

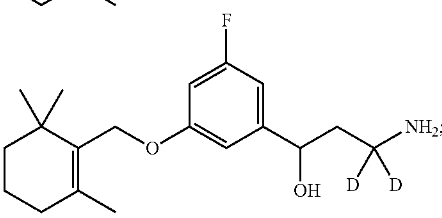

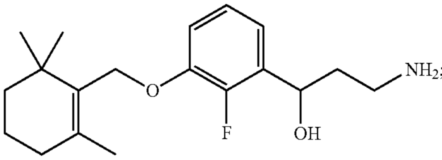

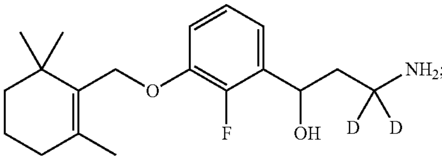

or a pharmaceutically acceptable salt, tautomer, or solvate thereof.

DETAILED DESCRIPTION

Figure 1A:
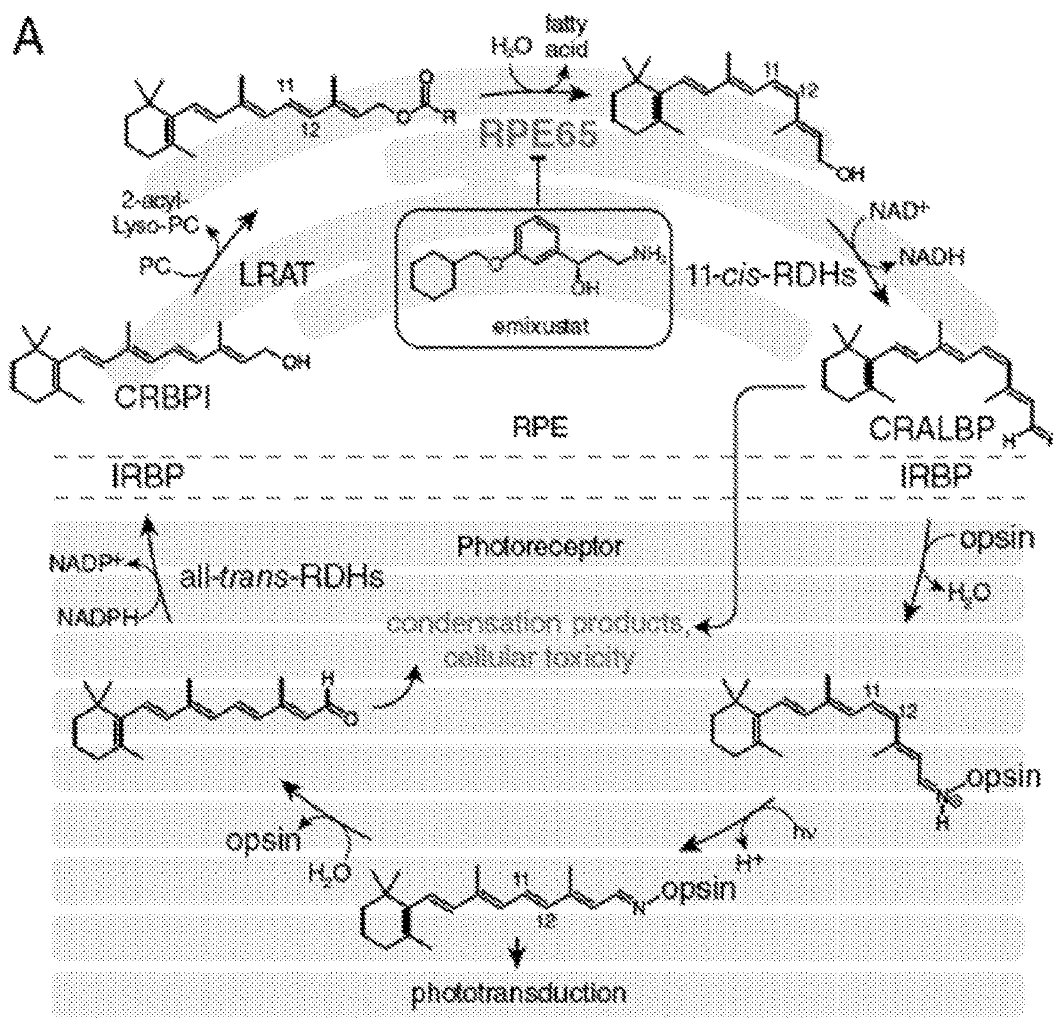
FIGS. 1(A-C) illustrate pharmacodynamics and pharmacokinetics of visual cycle modulators. A) Visual cycle modulators such as emixustat inhibit RPE65, thus blocking the key trans/cis isomerization step of the visual cycle. Slowing of the visual kinetics reduces the formation of toxic retinaldehyde condensation products in the retina. B) Sites of emixustat modification in vivo and strategies to modify its metabolism. Emixustat is cleared primarily by two oxidative pathways involving C-4"-hydroxylation of its cyclohexyl ring by cytochrome P450 enzymes and oxidative deamination by the enzyme vascular adhesion protein-1 (VAP-1). C) Three strategies for modifying emixustat metabolism were investigated in this work: i)C-3-deuteration to potentially slow deamination via a primary kinetic isotope effect, ii) inductive electron density withdrawal from the γ-aminoalcohol functionality to alter its basicity and reactivity via aryl C-2' fluorination, and iii)C-5"-difluorination of the cyclohexyl to deactivate the ring towards oxidative modification; C-6" is also a hydroxylation site.
Figure 1B:
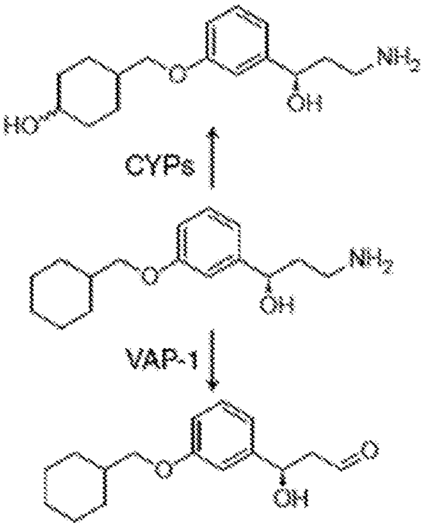

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.,", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this application may exist in stereoisomeric form, therefore, can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refer to the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative", refers to compounds that have a common core structure, and are substituted with various groups as described herein. For example, all of the compounds represented by formula I are primary amines and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" refer to modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" refers to inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" refers to stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term a "pharmaceutical composition" refers to a formulation containing the disclosed compounds in a form suitable for administration to a subject. The pharmaceutical composition can be in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including ocular, oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" refers to a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claims.

The phrase "pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present application is intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulftydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds described herein, and the like (e.g., Bundegaard, H. "Design of Prodrugs" p1-92, Elesevier, New York-Oxford (1985)).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2$^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, 3$^{rd}$ ed. 2003).

The term "amine protecting group" refers to a functional group that converts an amine, amide, or other nitrogen-containing moiety into a different chemical group that is substantially inert to the conditions of a particular chemical reaction. Amine protecting groups can be removed easily and selectively in good yield under conditions that do not affect other functional groups of the molecule. Examples of amine protecting groups include, but are not limited to, formyl, acetyl, benzyl, t-butyldimethylsilyl, t-butdyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other amine protecting groups can be identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as primates, mammals, and vertebrates.

The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" refer to molecules and other agents that are biologically, physiologically, or pharmacologically active substances that act locally or systemically in a patient or subject to treat a disease or condition, such as retinal degeneration or other forms of retinal disease whose etiology involves elevated levels of all trans-retinal in the ocular tissue of a subject. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" refer to the dose of a drug, which produces 50% of its maximum response or effect, or alternatively, the dose, which produces a pre-determined response in 50% of test subjects or preparations. The term "LD50" refers to the dose of a drug, which is lethal in 50% of test subjects. The term "therapeutic index" refers to the therapeutic index of a drug, defined as LD50/ED50.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment. A nonlimiting example of such an alkyl moiety that is a diradical is $—CH_2CH_2—$, i.e., a $C_2$ alkyl group that is covalently bonded via each terminal carbon atom to the remainder of the molecule.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, $—CF_3$, or —CN, or the like.

As used herein, "halo" or "halogen" refers to fluoro, chloro, bromo, and iodo. "Counterion" is used to represent a small, negatively charged species such as fluoride, chloride, bromide, iodide, hydroxide, acetate, and sulfate.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

In the specification, the singular forms also include the plural, unless the context clearly dictates otherwise. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

"Small molecule" refers to a molecule, which has a molecular weight of less than about 2000 amu, or less than about 1000 amu, and even less than about 500 amu.

All percentages and ratios used herein, unless otherwise indicated, are by weight.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity"). "Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

Embodiments described herein relate to compounds that include primary amines for use in the treatment of ocular disorders, such as ocular diseases and disorders related to aberrant all-trans-retinal accumulation in a subject's ocular tissue. It has been discovered that all-trans-retinal, a retinoid metabolite naturally produced during visual processing, is highly toxic when present at elevated levels. To lower its toxicity, therapeutic compounds that include primary amines have been identified in the Example below that can be delivered to and retained in the eye to modulate the visual (retinoid) cycle.

The compounds described herein have strategically incorporated deuterium and/or fluorine to modulate the compounds potency and metabolism. Regioselective incorporation of fluorine can impact pKa modulation; alter target selectivity through conformational variations or changes in specific hydrophobic interactions; and alter tissue-specific penetration (e.g., central nervous system (CNS)), through modification of lipophilicity. These effects of fluorination are in addition to the well-established strategy of replacing metabolically labile hydrogens with C—F bonds. Regioselective incorporation of deuterium can be used to attenuate amine oxidation and rapid metabolic elimination via engineering a localized primary isotope effect. Collectively, the compounds have improved potency, absorption, selectivity, and metabolism to mitigate the toxicity of all-trans-retinal in age-related blindness.

In some embodiments, the ocular disorder associated with aberrant all-trans-retinal accumulation in the ocular tissue of a subject can include, for example, retinal degeneration, macular degeneration, including age-related macular degeneration including the dry form and the wet form of age related macular degeneration, Stargardt's disease, Stargardt macular degeneration, fundus flavimaculatus, geographic atrophy, retinitis pigmentosa, ABCA4 mutation related retinal dystrophies, vitelliform (or Best) macular degeneration, adult onset form of vitelliform macular dystrophy, Sorsby's fundus dystrophy, Malattia leventinese (Doyne honeycomb or dominant radial drusen), diabetic retinopathy, diabetic maculopathy, diabetic macular edema, retinopathy that is or presents geographic atrophy and/or photoreceptor degeneration, retinopathy that is a lipofuscin-based retinal degeneration, aberrant modulation of lecithin-retinol acyltransferase in an eye, Leber's congenital amaurosis, retinal detachment, hemorrhagic retinopathy, hypertensive retinopathy, hereditary or non hereditary optic neuropathy, inflammatory retinal disease, retinal blood vessel occlusion, retinopathy of prematurity, ischemia reperfusion related retinal injury, proliferative vitreoretinopathy, retinal dystrophy, uveitis, retinal disorders associated with Alzheimer's disease, retinal disorders associated with multiple sclerosis, retinal disorders associated with Parkinson's disease, retinal disorders associated with viral infection (cytomegalovirus or herpes simplex virus), retinal disorders related to light overexposure or myopia, retinal disorders associated with AIDS, glaucoma, genetic retinal dystrophies, traumatic injuries to the optic nerve, such as by physical injury, excessive light exposure, or laser light, neuropathies due to a toxic agent or caused by adverse drug reactions or vitamin deficiency, progressive retinal atrophy or degeneration, retinal diseases or disorders resulting from mechanical injury, chemical or drug-induced injury, thermal injury, radiation injury, light injury, or laser injury, hereditary and non-hereditary retinal dystrophy, ophthalmic injuries from environmental factors, such as light-induced oxidative retinal damage, laser-induced retinal damage, "flash bomb injury," or "light dazzle", refractive errors including but not limited to myopia, and retinal diseases related to A2E accumulation including RDS/PHRP2-related macular degeneration, Batten disease (juvenile neuronal ceroid lipofuscinosis), and central serous chorioretinopathy.

Present at high micromolar levels, all-trans-retinal is uniquely concentrated in the eye and constitutes an ideal target for compounds described herein that do not interact with cellular machinery and processes. When administered to a subject, the primary amine containing compounds described herein transiently sequester all-trans-retinal in ocular tissue by forming a Schiff base and thus reduce peak concentrations of the toxic aldehyde. Because this reaction is readily reversible, there is no discernable diminution in the total amount of all-trans retinal needed for replenishment of the visual chromophore, 11-cis-retinal. In certain embodiments, the stability of the Schiff-bases formed from the retinal sequestering compounds should be such that the level of free all-trans-retinal in the ocular tissue of a subject is reduced to a level that is effective to mitigate retinal degeneration but not impair the normal retinoid cycle.

In some embodiments, the compounds in accordance with the application inhibit RPE65 enzymatic activity involved in retinoid metabolism in the eye of the subject. In certain embodiments, the compounds for use in a method described herein inhibit or at least partially inhibit RPE65 and but do not cause delayed dark adaptation (i.e., night blindness) in a subject.

In an embodiment of the application, the compounds can inhibit retinal degeneration upon administration to a subject can be selected using an in vitro assays that measure the ability of a compound to inhibit retinoid isomerase activity and sequester excessive all-trans-retinal in the ocular tissue and in vivo assays that measure, chromophore regeneration and ERG and the optical coherence tomography score of retinas of $Rdh8^{-/-}$ $Abca4^{-/-}$ mice exposed to intense light-induced retinal degeneration. In certain embodiments, the compounds that can inhibit retinal degeneration upon administration to a subject at least partially inhibit RPE65 activity in a subject's ocular tissue. In some embodiments, retinal sequestering compounds when administered to a $Rdh8^{-/-}$ $Abca4^{-/-}$ mouse increase the optical coherence tomography score of the mouse in comparison to untreated control animal. Additionally, in some embodiments, therapeutic efficacy of the compounds of the application can be determined using an in vitro assay that measures the ability of a compound to improve viability of RPE cells treated with retinal.

In some embodiments, the compound for use in a method described herein can include the formula (I):

(I)

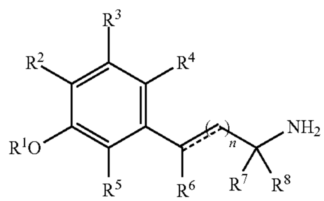

or be a pharmaceutically acceptable salt, tautomer, or solvate thereof;

wherein n is an integer from 0 to 6;

$R^1$ is a substituted or unsubstituted $C_1$-$C_{12}$ alkyl, $C_2$-$C_{12}$ alkenyl, $C_2$-$C_{12}$ alkynyl, $C_3$-$C_{12}$ aryl, heteroaryl, heterocyclyl, or $C_6$-$C_{12}$ alkaryl;

$R^2$, $R^4$, and $R^5$ are each independently H or F;

$R^3$ is H, F, or an alkyl or a fluoro alkyl group that includes at least three carbon atoms;

$R^6$ is H, $CH_3$, or OH;

$R^7$ and $R^8$ are H or D, wherein at least one of $R^7$ or $R^8$ is D if $R^2$, $R^4$, and $R^5$ are H; and the dashed line is an optional bond.

In some embodiments, at least one of $R^7$ or $R^8$ is D. For example, both of $R^7$ and $R^8$ are D.

In some embodiments, at least one of $R^2$ or $R^5$ is F. For example, $R^2$ can be F.

In other embodiments, $R^1$ is selected from the group consisting of:

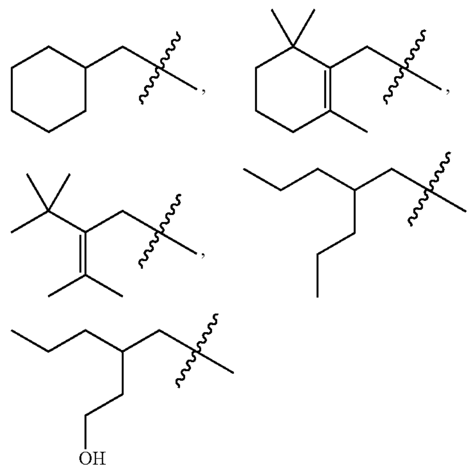

and fluoro derivatives thereof. For example, $R^1$ is selected from the group consisting of:

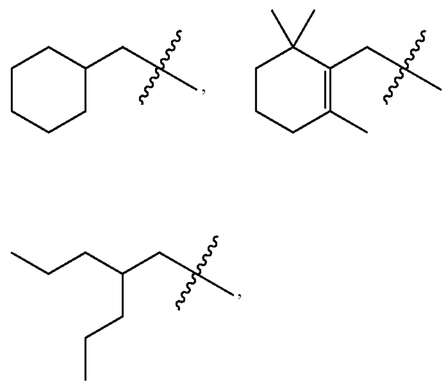

and fluoro derivatives thereof.

In some embodiments, $R^3$ is a branched or cyclic $C_3$-$C_{24}$ alkyl or fluoroalkyl. For example, $R^3$ can be selected from the group consisting of:

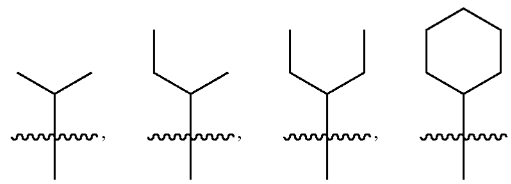

and fluoro derivatives thereof.

In other embodiments, the compound for use in a method described herein can include the formula (II):

(II)

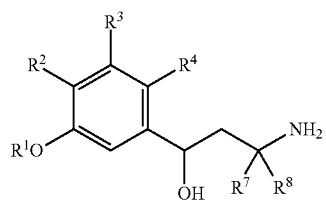

or be a pharmaceutically acceptable salt, tautomer, or solvate thereof;

wherein $R^1$ is a substituted or unsubstituted $C_1$-$C_{12}$ alkyl, $C_2$-$C_{12}$ alkenyl, $C_2$-$C_{12}$ alkynyl, $C_3$-$C_{12}$ aryl, heteroaryl, heterocyclyl, or $C_6$-$C_{12}$ alkaryl;

$R^2$ and $R^4$ are each independently H or F;

$R^3$ is H, F, or an alkyl or a fluoro alkyl group that includes at least three carbon atoms; and $R^7$ and $R^8$ are H or D, wherein at least one of $R^7$ or $R^8$ is D if $R^2$ and $R^4$ are H. In some embodiments, at least one of $R^7$ or $R^8$ is D. For example, both of $R^7$ and $R^8$ can be D.

In some embodiments, $R^2$ is F.

In other embodiments, $R^1$ is selected from the group consisting of:

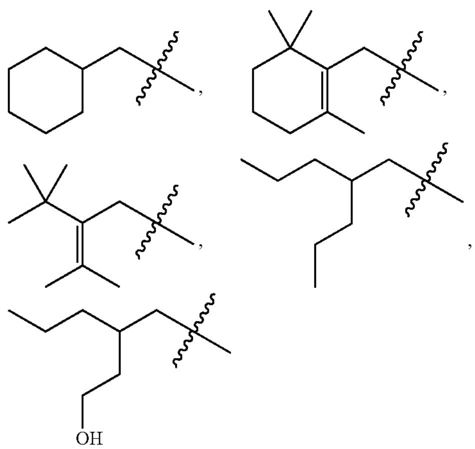

and fluoro derivatives thereof. For example, $R^1$ can be selected from the group consisting of:

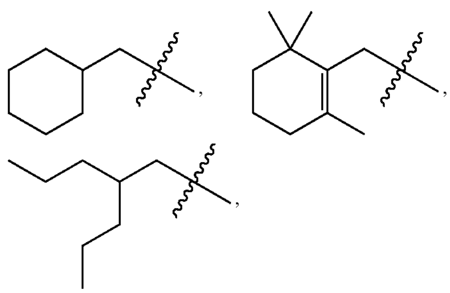

and fluoro derivatives thereof.

In some embodiments, $R^3$ is a branched or cyclic $C_3$-$C_{24}$ alkyl or fluoroalkyl. For example, $R^3$ can be selected from the group consisting of:

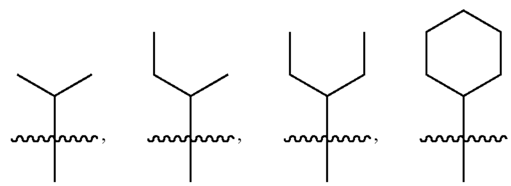

and fluoro derivatives thereof.

In other embodiments, the compound for use in a method described herein can include the formula (III):

(III)

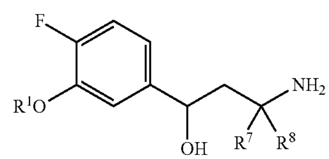

or be a pharmaceutically acceptable salt, tautomer, or solvate thereof;

wherein $R^1$ is a substituted or unsubstituted $C_1$-$C_{12}$ alkyl, $C_2$-$C_{12}$ alkenyl, $C_2$-$C_{12}$ alkynyl, $C_3$-$C_6$ aryl, heteroaryl, heterocyclyl, or $C_6$-$C_{12}$ alkaryl; and $R^7$ and $R^8$ are H or D.

In some embodiments, at least one of $R^7$ or $R^8$ is D. For example, both of $R^7$ and $R^8$ can be D.

In some embodiments, $R^1$ is selected from the group consisting of:

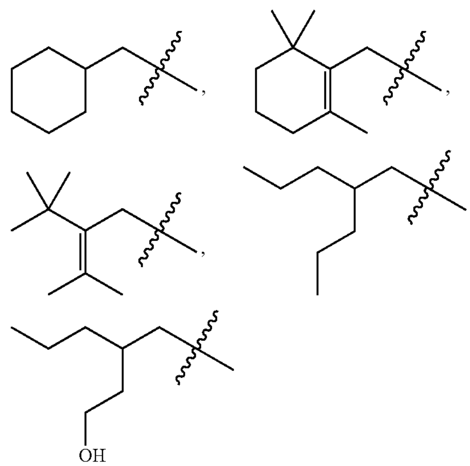

and fluoro derivatives thereof. For example, $R^1$ can be selected from the group consisting of:

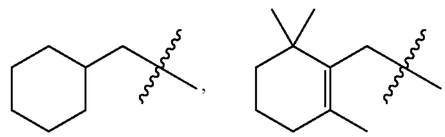

-continued

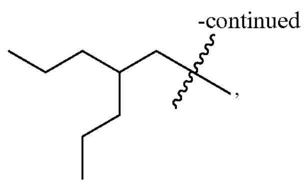

and fluoro derivatives thereof.

In other embodiments, the compound for use in a method described herein can include the formula (IV):

(IV)

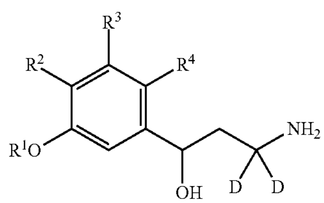

or be a pharmaceutically acceptable salt, tautomer, or solvate thereof;

wherein $R^1$ is a substituted or unsubstituted $C_1$-$C_{12}$ alkyl, $C_2$-$C_{12}$ alkenyl, $C_2$-$C_{12}$ alkynyl, $C_3$-$C_{12}$ aryl, heteroaryl, heterocyclyl, or $C_6$-$C_{12}$ alkaryl;

$R^2$ and $R^4$ are each independently H or F; and $R^3$ is H, F, or an alkyl or a fluoro alkyl group that includes at least three carbon atoms.

In some embodiments, $R^2$ can be F.

In other embodiments, $R^1$ is selected from the group consisting of:

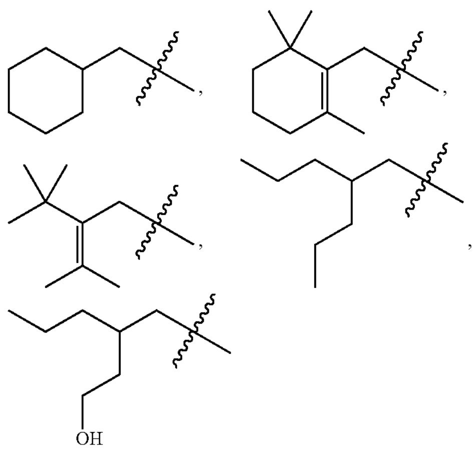

and fluoro derivatives thereof. For example, $R^1$ can be selected from the group consisting of:

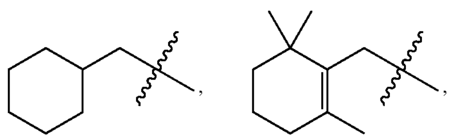

-continued

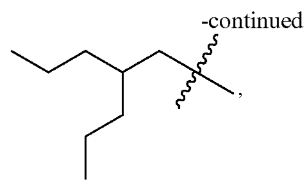

and fluoro derivatives thereof.

In some embodiments, $R^3$ is a branched or cyclic $C_3$-$C_{24}$ alkyl or fluoroalkyl. For example, $R^3$ can be selected from the group consisting of:

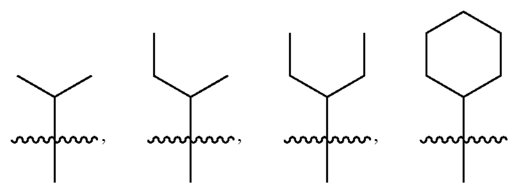

and fluoro derivatives thereof.

In other embodiments, the compound for use in a method described herein can include the formula (V):

(V)

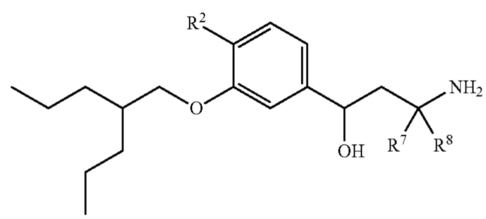

or be a pharmaceutically acceptable salt, tautomer, or solvate thereof;

wherein $R^2$ is H or F; and $R^7$ and $R^8$ are each independently H or D, and wherein at least one of $R^7$ or $R^8$ is D if $R^2$ is H.

In some embodiments, at least one of $R^7$ or $R^8$ is D. For example, both of $R^7$ and $R^8$ can be D.

In other embodiments, $R^2$ can be F.

In other embodiments, the compound can have formula (VI):

(VI)

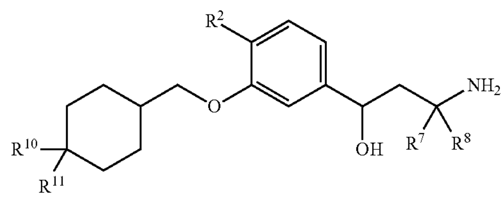

or be a pharmaceutically acceptable salt, tautomer, or solvate thereof;

wherein $R^2$ is H or F;

$R^7$ and $R^8$ are each independently H or D, and wherein at least one of $R^7$ or $R^8$ is D if $R^2$ is H; and $R^{10}$ and $R^{11}$ are each independently H or F.

In some embodiments, at least one of $R^7$ or $R^8$ is D. For example, both of $R^7$ and $R^8$ can be D.
In some embodiments, $R^2$ is F.
In other embodiments, the compound can be selected from:
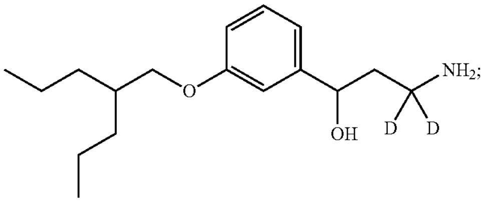
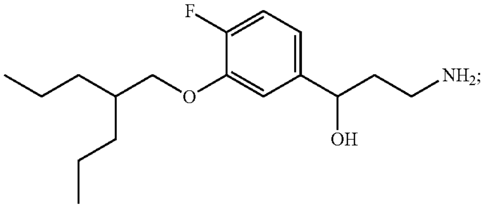
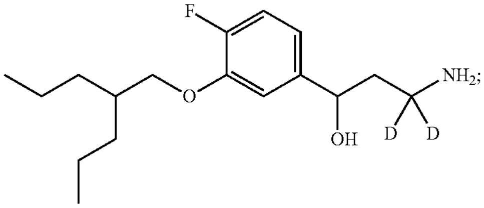
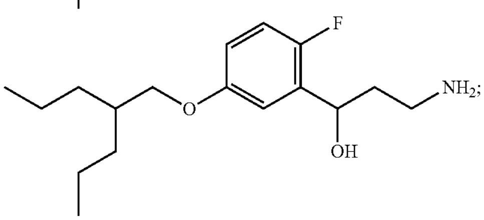
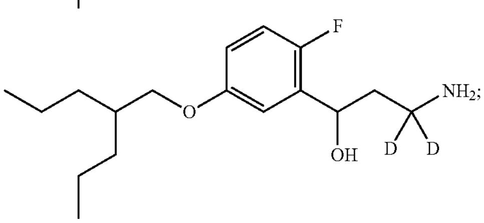
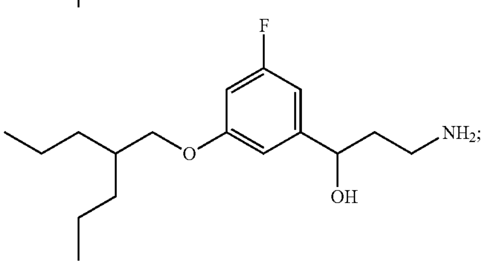
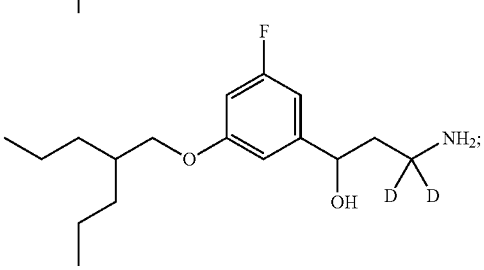
-continued
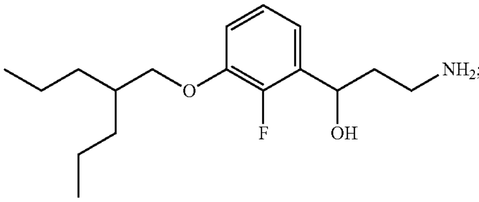
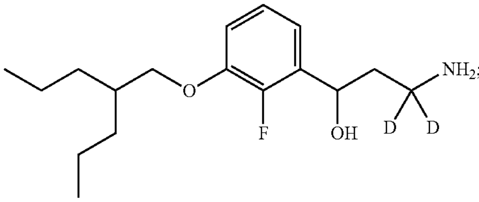
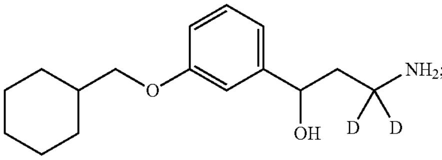
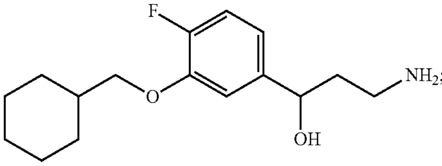
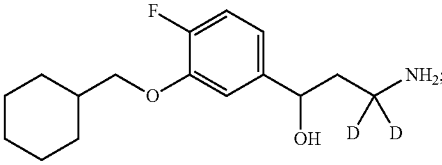
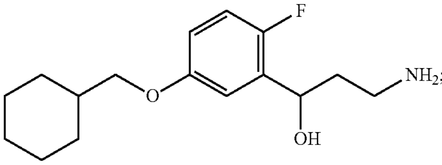
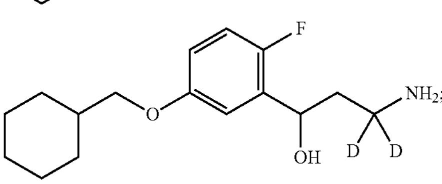
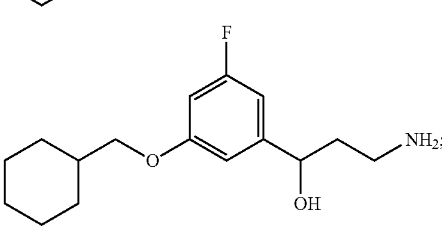
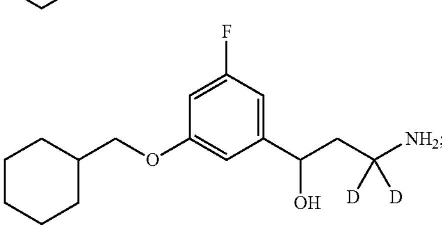

-continued
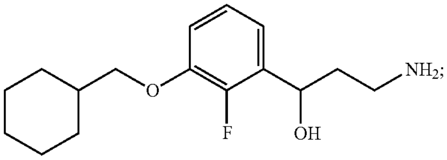
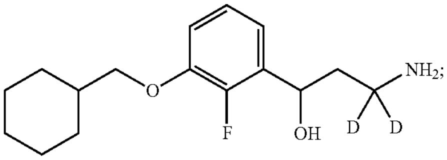
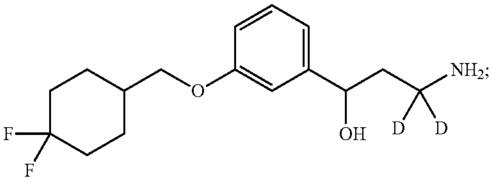
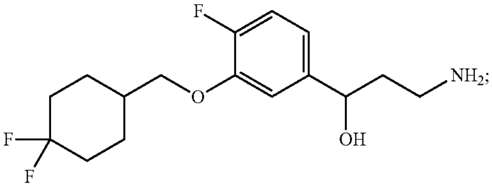
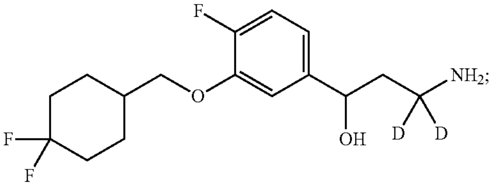
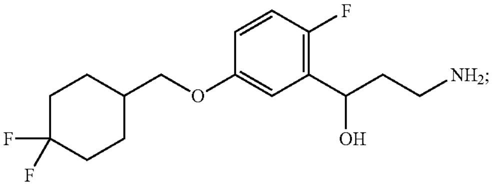
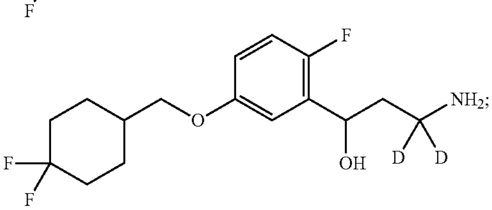
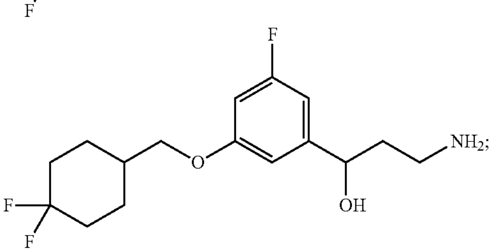
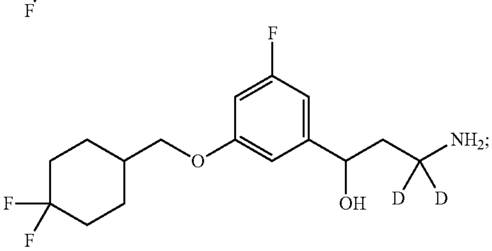
-continued
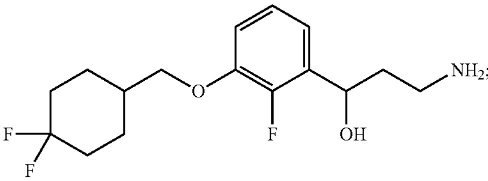
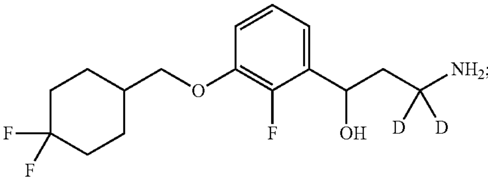
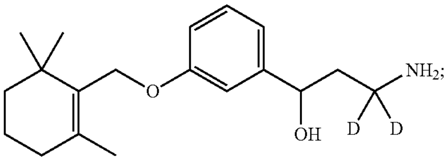
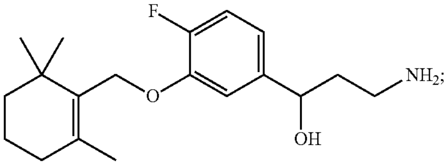
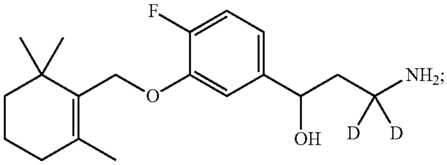
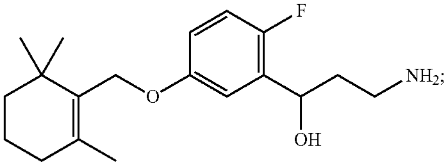
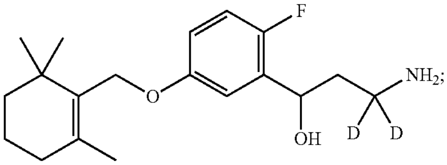
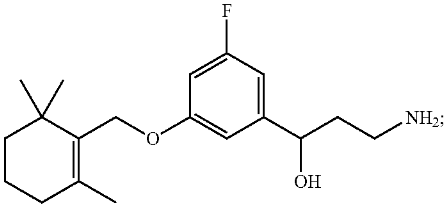
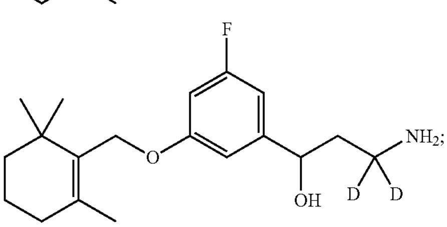

-continued

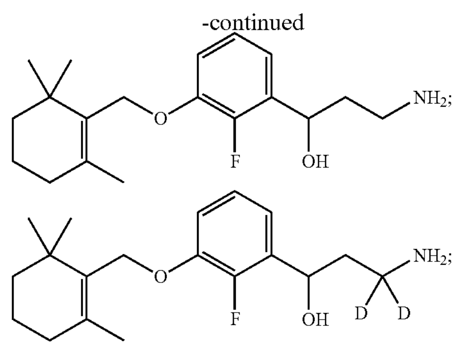

or a pharmaceutically acceptable salt, tautomer, or solvate thereof.

The compounds used in methods described herein can be administered to the subject to treat the ocular disorder (e.g., macular degeneration or Stargardt disease) using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Generally, the effective amount of the compound may be in the range of about 1 to 1,000 mg in the oral administration, about 0.1 to 500 mg in the intravenous administration, about 5 to 1,000 mg in the topical administration. Generally, the daily dosage for adults is in the range of about 0.1 to 5,000 mg, preferably about to 1,000 mg but cannot be determined uniformly because it depends on age, sex, body weight and the physical condition of the patients to be treated. The formulation may be administered once a day or several times a day with a divided dose Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day. In another embodiment, the compound can be administered after induction of macular degeneration has occurred.

The treatment methods can include administering to the subject a therapeutically effective amount of the compound. Determination of a therapeutically effective amount is within the capability of those skilled in the art. The exact formulation, route of administration, and dosage can be chosen by the individual physician in view of the subject's condition.

Formulation of pharmaceutical compounds for use in the modes of administration noted above (and others) are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, the compound can be provided in an ophthalmic preparation that can be administered to the subject's eye. The ophthalmic preparation can contain the compound in a pharmaceutically acceptable solution, suspension or ointment. Some variations in concentration will necessarily occur, depending on the particular compound employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The compound can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin can include, for example, ointments, creams, gels and pastes comprising the retinal sequestering compound in a pharmaceutical acceptable carrier. The formulation of the retinal sequestering compound for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with or at risk of macular degeneration, which are not readily accessible or suitable for ophthalmic (e.g., eye-drops) and/or topical administration, can be treated by a systemic approach, such as oral, enteral, or intravenous infusion. For example, the compound can be administered at a low dosage by continuous intravenous infusion.

In another example, in which a patient requires longer-term care, the compound can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the compound to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the retinal sequestering compound.

As discussed above, the compounds may be administered to a subject in order to treat or prevent macular degeneration and other forms of retinal disease whose etiology involves elevated levels of toxic all-trans-retinal in a subject. Other diseases, disorders, or conditions characterized by increased or excessive all-trans-retinal in ocular tissue may be similarly treated.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves increased all-trans-retinal in ocular tissue of a subject, and then the compound is administered. In another embodiment, a subject may be identified as being at risk for developing other forms of retinal disease whose etiology involves increased all-trans-retinal in ocular tissue, and then the disclosed compound is administered. In some embodiments, a compound is administered prophylactically. In some embodiments, a subject has been diagnosed as having the disease before retinal damage is apparent. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease whose etiology involves increased all-trans-retinal accumulation in ocular tissue, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD, which is treated with, e.g., photodynamic therapy.

In yet another embodiment, the compound described herein can be administered as part of a combinatorial therapy with additional therapeutic agents. The phrase "combinatorial therapy" or "combination therapy" embraces the administration of a compound, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

The invention is further illustrated by the following example, which is not intended to limit the scope of the claims.

Example

Figure 1C:
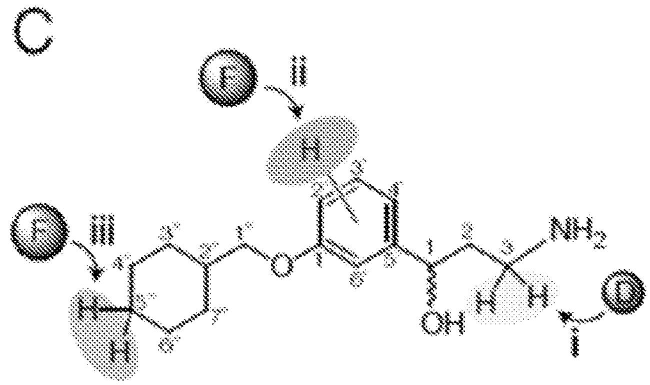

In this Example, we describe the synthesis of several derivatives of emixustat, involving strategic incorporation of deuterium and/or fluorine to investigate three areas of the emixustat structure that could modulate its potency and metabolism (FIG. 1C). Regioselective incorporation of fluorine can have a broad range of potential impacts on the properties of small molecules. These include pKa modulation; alteration of target selectivity through conformational variations or changes in specific hydrophobic interactions; and alteration of tissue-specific penetration (e.g., CNS), through modification of lipophilicity. These effects of fluorination are in addition to the well-established strategy of replacing metabolically labile hydrogens with C—F bonds. Regioselective incorporation of deuterium was utilized to investigate the role of amine oxidation in the rapid metabolic elimination of emixustat. We hypothesized that we could attenuate this metabolic process via engineering a localized primary isotope effect. Collectively, we envisioned a collection of rationally designed compounds that could improve the potency, absorption, selectivity, and metabolism of drug candidates to mitigate the toxicity of all-trans-retinal in age-related blindness.

Methods

RPE65 Crystallization and Structure Determination

Crystals of RPE65 in complex with 4-fluoro-emixustat (49), C-2'-fluoro-MB-004 (24), or C-5'' gem-difluoro-emixustat (57) were obtained using previously described procedures. Briefly, isolated bovine RPE membranes were incubated with 1 mM of each compound (delivered in DMF) for 15 min prior to solubilization with 24 mM hexaethylene glycol monooctyl ether ($C_8E_6$). After anion exchange chromatography, purified RPE65 was concentrated to 10-15 mg/mL and the test compounds were again to a concentration of 1 mM prior to crystallization. An RPE65 sample was also prepared in the absence of added inhibitors. Crystals were grown by the hanging-drop vapor-diffusion method by mixing 2 μL of a 10 mg/mL RPE65 sample with 2 μL of one of the following crystallization solutions: 100 mM 2-(cyclohexylamino)ethanesulfonic acid-NaOH, pH 9.5, containing 40% (v/v) polyethylene glycol 300 and 200 mM NaCl, which was used for the samples containing 49 or no added inhibitor, or 100 mM Tris-HCl, pH 8.5, containing 30% (v/v) polyethylene glycol 200 and 200 mM ammonium phosphate dibasic, which was used for the samples containing 24 or 57. In both cases, the drops were incubated over a well solution consisting of 100 mM 2-(cyclohexylamino)ethanesulfonic acid-NaOH, pH 9.5, containing 40% (v/v) polyethylene glycol 300 and 200 mM NaCl at 8° C. Crystals of approximately 100×100×300 μm in size were obtained after 1-2 weeks of incubation. Mature crystals were harvested directly into liquid nitrogen for X-ray data collection.

X-ray diffraction data were collected at the SSRL 12-2, the APS NE-CAT 24-ID-E, or the NSLS-II FMX beam-Lines. Data were processed using XDS and the initial model was obtained by direct refinement using published RPE65 coordinates in which ligands had been removed (PDB accession codes: 4RSE and 4RSC). The structures were refined by alternating reciprocal space refinement in REFMAC[4] and manual building and adjustments in Coot. Ligand coordinates and geometry dictionary files were generated using the Grade server (http://grade.globalphasing.org/cgi-bin/grade/server.cgi). The models were validated using Molprobity and the wwPDB validation server.

RPE65 Retinoid Isomerase Activity Assay

Primary amine listed in Table 2 in DMF (1 μL) was added into a suspension containing 300 μg of RPE microsomal proteins, 1% bovine serum albumin (BSA), 2 mM disodium pyrophosphate, and 25 μM human apo-cellular retinaldehyde-binding protein (CRALBP) in 10 mM BTP buffer (200 μL) to a final concentration from 0 to 2 μM. After incubation at room temperature for 5 min, the resulting mixture was mixed with half microliter of all-trans-retinol (5 mM) in DMF, and then incubated at 37° C. for 1 h. The reaction was quenched by adding 400 μL of methanol (Fisher Chemical, Fair Lawn, NJ), and the products were extracted with 400 μL of hexanes. Production of 11-cis-retinol was quantified by normal phase HPLC using a Zorbax Rx-SIL column (5 μm, 4.6×250 mm, Agilent, Santa Clara, CA) with 10% (v/v) ethyl acetate in hexanes as the eluent at a flow rate of 1.4 mL-min$^{-1}$. Retinoids were detected by monitoring their absorbance at 325 nm and quantified based on a standard curve representing the relationship between the amount of 11-cis-retinol and the area under the corresponding chromatographic peak.

Quantification of Representative Primary Amine Compound Levels in Serum and Eyes of Mice after Treatments Eight weeks old BL/6J mice were treated with 380 nmol visual cycle modulator 24, 49, 57, 58, 59 or emixustat in DMSO (50 μL) by intraperitoneal injection, and sacrificed at 3 h, 1 day, or 7 days later. Blood and eyeball samples were collected immediately. After clotting at room temperature for 30 min, the blood samples were centrifuged for 10 minutes at 17,000 g in a temperature-controlled benchtop centrifuge (Eppendorf AG). Each serum sample (100 μL) was carefully removed to avoid disturbing loose clots, precipitated with 400 p L of pre-cooled methanol, and centrifuged at 17,000 g for 15 min at 4° C. The supernatant was carefully transferred to a SpinX centrifuge tube filter with a 0.45 μm cellulose acetate membrane (Costar, Salt Lake City, UT), and centrifuged at 7,000 g for 2 min. Filtered samples were dried under vacuum, reconstituted in 100 μL 50% methanol/water, and centrifuged at 17,000 g for 15 min at 4° C. The resulting supernatants were ready for Liquid Chromatography/Mass Spectrometry analyses. The two eyeballs from each mouse were homogenized in acetonitrile (2×800 μL). The resulting mixture was centrifuged at 17,000 g for 15 min at 4° C. The supernatant was dried under vacuum, reconstituted in 100 μl 50% methanol/water, and centrifuged at 17,000 g for 15 min at 4° C. Twenty microliters of the supernatant extracted from serum or eye samples was injected into an Ultimate 3000 HPLC system coupled with LXQ mass spectrometer (ThermoFisher Scientific, Waltham, MA) with an electrospray ionization unit. The separation was performed on a Proshell EC-18 column (2.7 μm, 3.0×150 mm, Agilent, Santa Clara, CA) using a mobile phase consisting of 0.1% aqueous formic acid (A) and acetonitrile (B) at a flow rate of 600 μL-min$^{-1}$ and the mobile phase gradients and time course were as follows: 0-2 min, 95% A/5% B; 2-10 min, 95%-15% A/5%-85% B. The signals were detected in the selected reaction monitoring (SRM) mode at conditions described in Table 4 and quantified based on the standard curves representing the relationship between the amounts of primary amine standards and the areas under the corresponding chromatographic peaks.

VAP-1 Oxidation Assay

Mouse aorta homogenates were used as the source of vascular adhesion protein-1 (VAP-1) for this study. Aortas were removed from mice (4-6 week-old) that had been euthanized by $CO_2$ asphyxiation followed by cervical dislocation. The aorta was dissected and the blood was removed by rinsing the tissue with phosphate-buffered saline. Aorta samples were used immediately or stored at −80° C. until needed. Two aortas were minced using a stainless steel single edge blade and homogenized in a KONTES Potter-Elvehjem tissue grinder/homogenizer glass pestle in 1 mL of 10 mM HEPES-NaOH, pH 7.6. The homogenate was collected into a 1.5 mL Eppendorf tube. Five μl of a 20 mM ethanolic stock solution of emixustat or $d_2$-emixustat (58) were added to the aorta homogenate to give a final substrate concentration of 100 μM. The sample was mixed and then incubated at 28° C. with 300 RPM shaking in an Eppendorf Thermomixer. 200 μL samples were taken at 0, 1, and 2 h after initiation of the reaction. At each time point, the reactions were immediately quenched with 100 μL of 100% MeOH, vortexed for 3 sec, and stored at −20° C. After samples from all time points were collected and frozen, the samples were thawed and centrifuged at 15,000 RPM for 10 min. 250 μL of each supernatant was collected, placed into a borosilicate tube, and dried in a Speedvac rotoevaporator. Each dried sample was redissolved in 300 μL of a 1:1 MeOH/$H_2O$ solution, centrifuged to remove particulates, and then transferred to an HPLC vial. 50 μL of the sample was used for analysis on an Agilent 1260 Infinity series HPLC equipped with a Proshell EC-18 column and a diode array detector. The sample was separated using a mobile phase consisting of 0.1% (v/v) formic acid in $H_2O$ and acetonitrile at the following ratios and time intervals: 95:5 for 2 min, a gradient from 95:5 to 15:85 over 8 min, a gradient from 15:85 to 2:98 over 0.5 min, continue 2:98 for 4 min, and then a gradient from 2:98 to 95:5 over 0.5 min. The reaction substrate and product were assessed by monitoring absorbance at 275 nm. Emixustat and $d_2$-emixustat eluted at ~8.5 min, while the assay product (ACU-5201) eluted at ~13.25 min. A dilution series of known concentrations of authentic ACU-5201 in 1:1 $MeOH/H_2O$ was run to generate a standard curve and facilitate the conversion of product AUCs to absolute mass.

Details of Quantum Chemical Calculations

Model Construction

We adapted a minimal, dimeric model for $Tyr^{275}$-fluorinated emixustat derivatives 24 or 49 (denoted collectively as EmixF), see FIG. 5 in the main text. Positions of heavy atoms (C, O, N, F) were taken from the crystal structures reported in the manuscript. Free valencies were saturated with hydrogen atoms and the entire system was assumed to be neutral. Finally, the positions of hydrogen atoms were optimized at the density functional theory level (DFT) using oB97X-D3BJ functional and def2-TZVPP basis set (non-hydrogen atoms were kept frozen).

Interaction Energy Calculations

Interaction energy of the dimer was evaluated at the coupled cluster singles, doubles and perturbative triples level [CCSD(T)]. To reduce computational cost, the domain-based local pair natural orbital approximation was employed [DLPNO-CCSD(T)]. Truncation thresholds were tightened ("TightPNO") as suggested for weakly interacting systems. DLPNO-CCSD(T) calculations were performed with def2-TZVPP basis set but the complete basis set limit (CBS) was estimated with additional Hartree-Fock (HF) and MP2 calculations extrapolated to CBS using two-point extrapolation scheme with def2-TZVPP and def2-QZVPP basis sets. Final DLPNO-CCSD(T)/CBS single point energy was obtained as:

$$E(\text{DLPNO-CCSD}(T)/CBS) \approx E_{HF}^{CBS} + E(\text{corr})_{CC}^{def2\text{-}TZVPP} + (E(\text{corr})_{MP2}^{CBS} - E(\text{corr})_{MP2}^{def2\text{-}TZVPP})$$

where $E_{HF}^{CBS}$ is the HF reference energy at the CBS and $E(\text{corr})_{MP2}^{CBS}$ denotes associated MP2 correlation energy at the CBS. DLPNO-CCSD(T) calculations with def2-TZVPP yield correlation energy $E(\text{corr})_{CC}^{def2\text{-}TZVPP}$ that is used to improve analogous component obtained with the MP2 method ($E(\text{corr})_{MP2}^{def2\text{-}TZVPP}$)

Such energy evaluations were carried out for the dimers shown in FIG. 5 in the main manuscript as well as for the monomers at the dimer geometry ($Tyr^{275}$, 24, and 49). The interaction energy was calculated as the difference between dimer energy and sum of the monomers energies. No geometry relaxation effects were included as these are protein-dependent.

For comparison, interaction energy was also obtained at the DFT level with oB97X-D3BJ functional with def2-QZVPP basis set.

Interaction Analysis

DLPNO-CCSD(T) interaction energy was decomposed into various components using local energy decomposition (LED) scheme. Here, the interaction energy is split into four principal terms:

$$\Delta E_{int} = \Delta E_{HF\text{-}CCSD}(\text{electro}) + \Delta E_{CCSD}(\text{disp}) + \Delta E(T) + \Delta E(CBS)$$

where $\Delta E_{HF\text{-}CCSD}$(electro) and $\Delta E_{CCSD}$(disp) denote contributions from electrostatic and dispersion interactions, respectively. The subscript denotes level of theory associated with particular ingredients. ΔE(T) and ΔE(CBS) provide correction for triples excitations and complete basis set limit, respectively. First three terms are computed at DLPNO-CCSD(T)/def2-TZVPP level while ΔE(CBS) accounts for the difference between total interaction energy at finite def2-TZVPP and estimatd CBS limit.

As described in the original report on LED, $\Delta E_{CCSD}$(disp) contains excitations where each fragment possess one hole and one particle (simultaneous single excitation on both fragments). $\Delta E_{HF\text{-}CCSD}$(electro) is commonly further split into following contributions:

$$\Delta E_{HF\text{-}CCSD}(\text{electro}) = \Delta E_{HF}(\text{el-prep}) + \Delta E_{CCSD}(\text{el-prep}) + \Delta E_{HF}(\text{elstat}) + \Delta EH_F(\text{exch}) + \Delta E_{CCSD}(CT\ EmixF \rightarrow Tyr) + \Delta E_{CCSD}(CT\ Tyr \rightarrow \text{EmixF})$$

The terms marked as 'el-prep' describe the energetic cost of wave-function preparation from an electronic ground state of the monomers into a deformed monomer functions in the presence of the second monomer. 'elstat' and 'exch' terms provide information on interaction between such deformed wave-functions that come from electrostatics and quantum-chemical exchange, respectively. Last two terms are the contributions from charge-transfer excitations (CT) from EmixF to Tyr or vice-versa.

Additionally, we used two methods to gain further insights into the nature of the interaction between Tyr and EmixF: (i) Non-covalent Interaction (NCI) analysis and (ii) Extended Transition State Natural Orbitals for Chemical Valence (ETC-NOCV) method. These calculations were performed with oB97X-D3BJ functional and def2-QZVPP basis set.

Common Techniques

Quantum-chemical calculations were performed with ORCA 4.2.0 program package. Coulomb and exchange integrals were efficiently evaluated with RI and COSX approximations, respectively. Appropriate def2 auxiliary basis sets were selected to correspond with orbital basis sets. DFT integration grids were enlarged (GridS and GridX6 in ORCA nomenclature) and tight energy convergence were applied (verytightscj). NCI analysis was carried out with Multiwfn program.

General Synthetic Experimental Methods

All reactions were performed in oven-dried glassware, under dry argon or nitrogen atmosphere. Synthesis under microwave irradiation was performed with Biotage, Initiator$^{+}$ Robot Eight—microwave system (Charlotte, NC). Lithium aluminum deuteride (98 atom % $^{2}H(D)$) was purchased from Millipore Sigma Isotopes (Miamisburg, OH). All other reagents were used as supplied by Holand-Moran (Geron 15, Israel), Millipore Sigma (Burlington, MA), Alfa Aesar (Haverhill, MA), Acros Organics (Geel, Belgium), Merck (Kenilworth, NJ), Bio-Lab Ltd (Hercules, CA), and IU-CHEM LTD (Shanghai, China). Tetrahydrofuran was distilled from a purple solution of sodium benzophenone ketyl. All other solvents were used as purchased. The $^{1}H$, $^{13}C^{25}$, $^{19}F$ NMR, and 2D spectra were recorded at 25° C. on Bruker Avance NMR spectrometers operating at 300, 400, 500, 600, and 700 MHz for the $^{1}H$ channel and were in accordance with the assigned structures. $^{19}F$ NMR spectra were recorded without decoupling from protons. Chemical shifts reported in 6 units, part per million (ppm) with reference to the residual solvent peak $CDCl_3$ (δ7.26), $CD_3OD$ (δ 3.31), $C_6D_6$(δ7.16) for $^{1}H$ and (δ77.36), $CD_3OD$ (δ49.00), $C_6D_6$(δ128.06) for $^{13}C$ spectra, respectively or TMS (δ0.00). NMR data are presented in the following order: chemical shift, peak multiplicity (b=broad, s=singlet, d=doublet, t=triplet, q=quartet, m=multiplet, dd=doublet of doublet, ddd=doublet of doublet of doublet, ddt=doublet of doublet of triplet, dq=doublet of quartet, dm=doublet of multiplet, br=broad), coupling constant (in Hz). Mass spectra were recorded in positive ionization mode on an Agilent 6545 QTOF mass spectrometer (Agilent technologies, USA), equipped with an electrospray ionization (ESI) and atmospheric pressure chemical ionization (APCI) interfaces, coupled to an Agilent 1260 Ultra High-Pressure Liquid Chromatography UHPLC (Agilent Technologies, Santa Clara, CA, USA). The Agilent 1260 series system consists of a G4204A quaternary pump, G4226A ALS auto-sampler, and G1316C column compartment. UHPLC was carried out on ZORBAX RRHD Eclipse Plus C18, 95 Å, 2.1×50 mm, 1.8 μm column (Agilent Technologies, USA) column with $H_2O$ (0.1% formic acid)-acetonitrile gradient elution from 5% to 95% acetonitrile in the course of 10 min at a flow rate of 0.5 mL/min. Preparative and analytical HPLC (Young Lin Instruments, Anyang, Korea) were performed on LUNA C18(2) (10 μm, 250 mm×21.2 mm) column and chiral column, LUX Amylose-1 (5 μm, 250 mm×21.2 mm), for preparative purification, and (5 μm, 250×4.6 mm) column for analysis, all from Phenomenex, Inc. (Torrance, CA). Acetonitrile and double distilled water were used as an eluent in different ratios. Liquid chromatography was performed using a forced air-flow (flash chromatography) on silica gel (Merck, 230-400 mesh), using eluting solvents (reported as V:V ratio mixture). Analytical thin-layer chromatography (TLC) was performed on 0.25 mm glass-backed EMD Millipore 60 F254 plates. Visualization of the developed chromatogram was accomplished with UV light (254 nm) and stained with either ethanolic phosphomolybdic acid (PMA), ceric ammonium molybdate, permanganate ($KMnO_4$), iodine, or vanillin physical adsorption for visualization. The final biological tested compounds displayed ≥95% purity (confirmed using analytical HPLC). Compound 57 was obtained of 90% purity.

Synthetic Procedures and Compound Characterization

Synthesis of the 2-Propylpentyl Family of γ-Hydroxyamines

Scheme 1 General Procedure for Synthesis of 2-propylpentyloxy Acetophenones

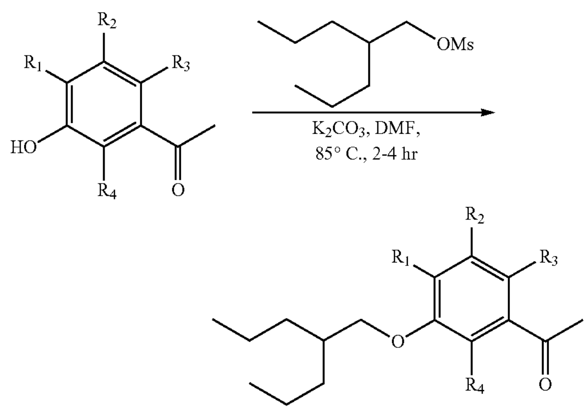

1: $R_2 = R_3 = R_4 = H$, $R_1 = F$
2: $R_1 = R_3 = R_4 = H$, $R_2 = F$
3: $R_1 = R_2 = R_4 = H$, $R_3 = F$
4: $R_1 = R_2 = R_3 = H$, $R_4 = F$

Potassium carbonate (9.73 mmol) was added to a solution of fluorinated 3-hydroxyacetophenone (6.48 mmol) in DMF (40 mL) and stirred at 0° C. under a nitrogen atmosphere for 15 min. 2-Propylpentyl mesylate (7.78 mmol) was added dropwise and the mixture was heated at 85° C. for 2-4 hr. The reaction mixture was cooled to 0° C. and quenched with a saturated aqueous solution of $NH_4Cl$ (50 mL) to pH 8. The aqueous layer was extracted with diethyl ether (5×50 mL). The organic layer was washed with $H_2O$ (20 mL) and brine (20 mL), dried over $Na_2SO_4$ and concentrated under reduced pressure. The residue was purified by flash chromatography on silica gel using hexane/EtOAc as an eluent to afford the desired acetophenones.

1

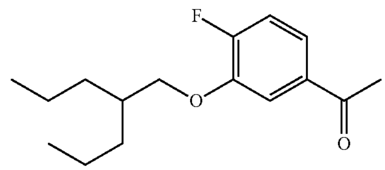

1-(4-Fluoro-3-((2-propylpentyl)oxy)phenyl)ethan-1-one (1):

The general synthesis was followed using 1-(4-fluoro-3-hydroxyphenyl)ethan-1-one (1.5 g, 9.73 mmol) to give 1 as a colorless oil (1.87 g, 72%). $^1$H NMR (400 MHz, $CDCl_3$): δ 7.59 (dd, J=2, 8.5 Hz, 1H) 7.5 (ddd, J=2, 4.5, 8.5 Hz, 1H), 7.12 (dd, J=8.5, 10.5 Hz, 1H), 3.95 (d, J=5.5 Hz, 2H), 2.58 (s, 3H), 1.95-1.79 (m, 1H), 1.57-1.22 (m, 8H), 0.92 (t, J=7 Hz, 6H). $^{13}$C NMR (100 MHz, $CDCl_3$): δ 196.67, 156 (d, J=255.5 Hz), 147.82 (d, J=11 Hz), 133.84 (d, J=3.5 Hz), 122.16 (d, J=8 Hz), 115.83 (d, J=19 Hz), 113.83 (d, J=3.5 Hz), 72.36, 37.49, 33.60, 26.44, 19.97, 14.40. $^{19}$F NMR (376 MHz, $CDCl_3$): δ-126.68 (ddd, J=4.5, 8, 10.5 Hz) ppm. HRMS (APCI): calculated for $C_{16}H_{23}FO_2$ $[M+H]^+$, 267.1754; found, 267.1755.

2

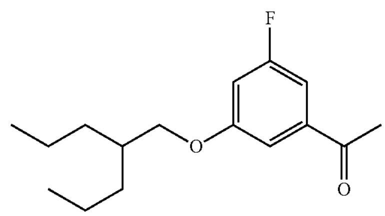

1-(3-Fluoro-5-((2-propylpentyl)oxy)phenyl)ethan-1-one (2)

The general synthesis was followed using 1-(3-fluoro-5-hydroxyphenyl)ethan-1-one (3.0 g, 19.46 mmol) to give 2 as a colorless oil (4.73 g, 91%). $^1$H NMR (400 MHz, $CDCl_3$): δ 7.32-7.24 (m, 1H) 7.2 (ddd, J=1.5, 2.5, 9 Hz, 1H), 6.81 (dt, J=2.5, 10.5 Hz, 1H), 3.86 (d, J=5.5 Hz, 2H), 2.57 (s, 3H), 1.92-1.75 (m, 1H), 1.54-1.3 (m, 8H), 0.91 (t, J=7 Hz, 6H). $^{13}$C NMR (100 MHz, $CDCl_3$) a, ppm, 196.74, 163.48 (d, J=247 Hz), 160.89 (d, J=11 Hz), 139.41 (d, J=8 Hz), 109.98 (d, J=2.5 Hz), 107.36 (d, J=23 Hz), 106.87 (d, J=25.5 Hz), 71.6, 37.45, 33.66, 26.71, 20, 14.41. $^{19}$F (376 MHz, $CDCl_3$): a, ppm, -111.26 (dd, J=9, 10.5 Hz). HRMS (APCI): calculated for $C_{16}H_{23}FO_2$ $[M+H]^+$, 267.1754; found, 267.1757.

3

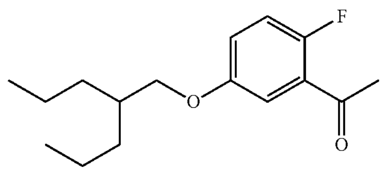

1-(2-Fluoro-5-((2-propyloentyl)oxy)phenyl)ethan-1-one (3):

The general synthesis was followed using 1-(2-fluoro-5-hydroxyphenyl)ethan-1-one (1.0 g, 6.48 mmol) to give 3 as a yellow oil (1.40 g, 81%). $^{1}$H NMR (300 MHz, $CDCl_3$): δ 7.41-7.29 (m, 1H) 7.12-6.98 (m, 2H), 3.83 (d, J=5.5 Hz, 2H), 2.64 (d, J=5 Hz, 3H), 1.90-1.72 (m, 1H), 1.51-1.24 (m, 8H), 0.91 (t, J=7 Hz, 6H). $^{13}$C NMR (75 MHz, $CDCl_3$): δ 195.80 (d, J=3.5 Hz), 156.76 (d, J=247.5 Hz), 155.53, 125.63 (d, J=14.5 Hz), 121.98 (d, J=14.5 Hz), 117.47 (d, J=26 Hz), 113.50 (d, J=2 Hz), 71.64, 37.5, 33.66, 31.41 (d, J=8 Hz) 19.98, 14.41. $^{19}$F NMR (376 MHz, $CDCl_3$): δ-120.23 (ddd, J=5, 10.5, 16 Hz). HRMS (APCI): calculated for $C_{16}H_{23}FO_2$ $[M+H]^+$, 267.1754; found, 267.1757.

4

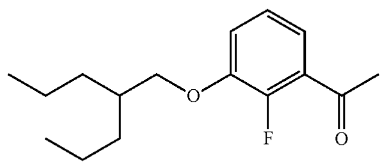

1-(2-Fluoro-3-((2-propylpentyl)oxy)phenyl)ethan-1-one (4)

The general synthesis was followed using 1-(2-fluoro-3-hydroxyphenyl)ethan-1-one (1.96 g, 12.75 mmol) to give 4 as a colorless oil (2.88 g, 68%). $^{1}$H NMR (400 MHz, $CDCl_3$): δ 7.45-7.30 (m, 1H) 7.0-7.2 (m, 2H), 3.91 (d, J=5.5 Hz, 2H), 2.65 (d, J=5 Hz, 3H), 1.79-1.99 (m, 1H), 1.28-1.59 (m, 8H), 0.93 (t, J=7 Hz, 6H). $^{13}$C NMR (100 MHz, $CDCl_3$): δ 196.24 (d, J=2 Hz), 152.92 (d, J=255 Hz), 1 48.27 (d, J=12 Hz), 126.73 (d, J=10.5 Hz), 123.92 (d, J=4 Hz), 120.94, 118.71 (d, J=2.5 Hz), 72.81, 37.69, 33.72, 31.61 (d, J=7.5 Hz) 20.09, 14.49. $^{19}$F NMR (376 MHz, $CDCl_3$): δ-132.15 (m). HRMS (APCI): calculated for $C_{16}H_{23}FO_2$ $[M+H]^+$, 267.1754; found, 267.1756.

Scheme 2 Mannich Reaction Methods

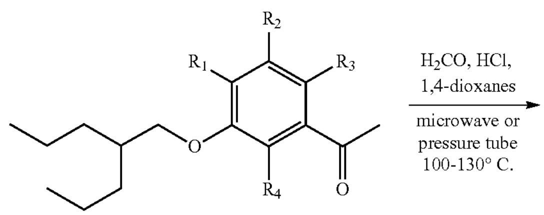

1: $R_2 = R_3 = R_4 = H, R_1 = F$
2: $R_1 = R_3 = R_4 = H, R_2 = F$
3: $R_1 = R_2 = R_4 = H, R_3 = F$
4: $R_1 = R_2 = R_3 = H, R_4 = F$

-continued

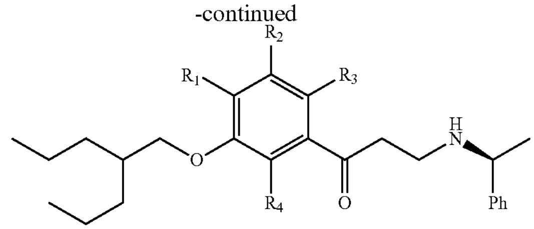

5: $R_2 = R_3 = R_4 = H, R_1 = F$
6: $R_1 = R_3 = R_4 = H, R_2 = F$
7: $R_1 = R_2 = R_4 = H, R_3 = F$
8: $R_1 = R_2 = R_3 = H, R_4 = F$

Method 1:

The mixture of acetophenone (2 mmol), paraformaldehyde (2 mmol), (S)-(−)-α-methylbenzylamine (2 mmol) and conc. HCl (32%, 0.23 mL,) in 1,4-dioxane (4 mL) was heated in four steps: 100° C. for 30 s, 110° C. for 30 s, 120° C. for 30 s, and 130° C. for 4 min in a microwave reaction vial. The crude was poured into a saturated aqueous solution of $NaHCO_3$ (10 mL), extracted with EtOAc (3×10 mL), washed with brine (10 mL), dried over $Na_2SO_4$, concentrated under reduced pressure, and purified by flash chromatography (MeOH/DCM) to afford β-amino carbonyl compound.

Method 2:

A mixture of fluorinated acetophenone (15 mmol), (S)-(−)-α-methylbenzylamine (18 mmol), 1,3,5-trioxane (18 mmol), and conc. HCl (32%, 1.71 mL) in 1,4-dioxane (20 mL) was heated in a sealed tube to 110° C. for 16 h. After being cooled to room temperature, the solvent was removed under reduced pressure. The crude was poured into a saturated aqueous solution of $NaHCO_3$ (30 mL), extracted with EtOAc (3×15 mL), washed with brine (15 mL), dried over $Na_2SO_4$, concentrated under reduced pressure, and purified by $SiO_2$ flash column chromatography using (MeOH/$CH_2Cl_2$) to give the desired Mannich products.

5

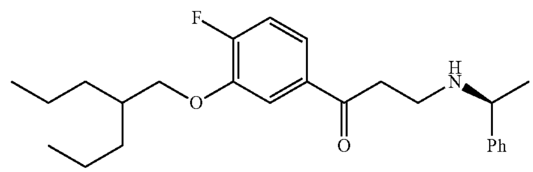

(S)-1-(4-Fluoro-3-((2-propylpentyl)oxy)phenyl)-3-((1-phenylethyl)amino)propan-1-one (5):

The general synthesis was followed using 1-(4-fluoro-3-((2-propylpentyl)oxy)phenyl)ethan-1-one (1) (1.06 g, 4.0 mmol) to give 5 as a yellowish oil (Method 1: 0.75 g, 47%). $^{1}$H NMR (400 MHz, $CDCl_3$): δ 7.56 (dd, J=2, 8 Hz, 1H), 7.45 (ddd, J=2.0, 4.5, 8.5 Hz, 1H), 7.38-7.16 (m, 5H), 7.09 (dd, J=8.5, 10.5 Hz, 1H), 3.93 (d, J=5.5 Hz, 2H), 3.81 (q, J=6.5 Hz, 1H), 3.11 (t, J=6 Hz, 2H), 2.95-2.85 (m, 1H), 2.84-2.70 (m, 1H) 1.91-1.84 (m, 1H), 1.54-1.22 (m, 11H), 0.92 (t, J=7 Hz, 6H). $^{13}$C NMR (100 MHz, $CDCl_3$): δ 198.34, 155.99 (d, J=257 Hz), 147.84 (d, J=11 Hz), 145.45, 133.84 (d, J=3.5 Hz), 128.48, 126.95, 126.59, 121.64 (d, 8 Hz), 115.87 (d, J=19.5 Hz), 113.82 (d, J=2.5 Hz), 72.39, 58.52, 42.60, 38.81, 37.48, 33.59, 24.43, 19.95, 14.39. $^{19}$F NMR (376 MHz, $CDCl_3$): δ-126.56 (m). HRMS (ESI): calculated for $C_{25}H_{34}FNO_2$ $[M+H]^+$, 400.2646; found, 400.2664.

6

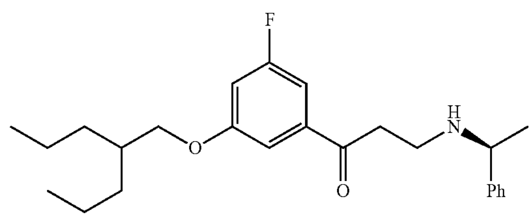

(S)-1-(3-Fluoro-5-((2-propylpentyl)oxy)phenyl)-3-((1-phenylethyl)amino)propan-1-one (6)

The general synthesis was followed using 1-(3-fluoro-5-((2-propylpentyl)oxy)phenyl)ethan-1-one (2) (6.33 g, 23.77 mmol) to give 6 as a colorless oil (Method 2: 3.20 g, 34%). $^1$H NMR (400 MHz, $CDCl_3$): δ 7.47-7.08 (m, 7H), 6.89-6.71 (dt, 1H, J=2, 10 Hz), 3.84 (d, J=2, 5.5 Hz, 2H), 3.80 (q, J=6.5 Hz, 1H), 3.08 (t, J=6 Hz, 2H), 2.95-2.84 (m, 1H), 2.84-2.71 (m, 1H) 1.87-1.75 (m, 1H), 1.46-1.29 (m, 11H), 0.92 (t, J=7 Hz, 6H). $^{13}$C NMR (100 MHz, $CDCl_3$): δ 198.46, 163.46 (d, J=245 Hz), 160.86 (d, J=11 Hz), 145.43, 139.18 (d, J=8 Hz), 128.48, 126.96, 126.59, 109.7 (d, J=1.5 Hz), 107 (d, J=23 Hz), 106.91 (d, J=25 Hz), 71.57, 58.49, 42.42, 39.17, 37.42, 33.64, 24.46, 19.98, 14.4. $^{19}$F NMR (376 MHz, $CDCl_3$): δ-111.13 (t, J=10 Hz). HRMS (ESI): calculated for $C_{25}H_{34}FNO_2$ $[M+H]^+$, 400.2646; found, 400.2647.

7

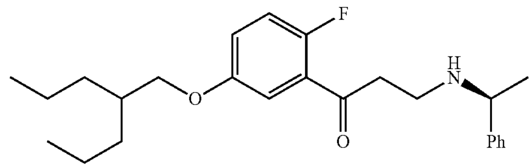

(S)-1-(2-Fluoro-5-((2-propylpentyl)oxy)phenyl)-3-((1-phenylethyl)amino)propan-1-one (7)

The general synthesis was followed using 1-(2-fluoro-5-((2-propylpentyl)oxy)phenyl)ethan-1-one (3) (0.53 g, 2 mmol) to give 7 as a yellowish oil (Method 1: 0.38 g, 47%). $^1$H NMR (300 MHz, $CDCl_3$): δ 7.59-7.14 (m, 6H), 7.13-6.85 (m, 2H), 4.05-3.58 (m, 3H), 3.45-2.94 (m, 2H), 2.94-2.84 (m, 1H), 2.84-2.62 (m, 1H), 1.87-1.7 (m, 1H), 1.5-1.26 (m, 1H), 0.91 (t, J=7 Hz, 6H). $^{13}$C NMR (75 MHz, $CDCl_3$): δ 197.92 (d, J=4.5 Hz), 156.50 (d, J=247.5 Hz), 155.56, 145.32, 128.46, 126.94, 126.61, 125.45 (d, J=14.5 Hz), 121.87 (d, 8.5 Hz), 117.51 (d, J=26.5 Hz), 113.54 (d, J=2.5 Hz), 71.66, 58.45, 43.80 (d, J=7.5 Hz), 42.37, 37.49, 33.66, 24.39, 19.98, 14.42. $^{19}$F NMR (376 MHz, $CDCl_3$): δ-119.95 (m). HRMS (ESI): calculated for $C_{16}H_{23}FO_2$ $[M+H]^+$, 400.2646; found 400.2647.

8

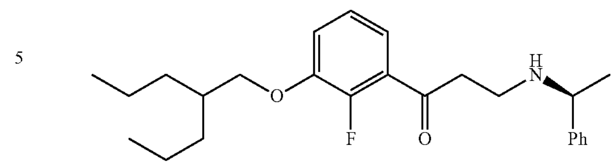

(S)-1-(2-Fluoro-3-((2-propylpentyl)oxy)phenyl)-3-((1-phenylethyl)amino)propan-1-one (8)

The general synthesis was followed using 1-(2-fluoro-3-((2-propylpentyl)oxy)phenyl)ethan-1-one (4) (4.0 g, 15.01 mmol) to give 8 as a clear oil (Method 2: 4.66 g, 78%). $^1$H NMR (300 MHz, $CDCl_3$): δ 7.36-7.21 (m, 6H), 7.09-7.04 (m, 2H), 3.88 (d, J=5.5 Hz, 2H), 3.8 (q, J=6.5 Hz, 1H), 3.27-3.05 (m, 2H), 3-2.65 (m, 2H), 1.87-1.7 (m, 1H) 1.50-1.25 (m, 11H), 0.92 (t, J=6.5 Hz, 6H). $^{13}$C NMR (75 MHz, $CDCl_3$): δ 198.06 (d, J=3 Hz), 152.45 (d, J=256 Hz), 148.04 (d, J=12 Hz), 145.46, 128.31, 126.73, 126.48, 126.39 (d, 10.5 Hz), 123.79 (d, J=4 Hz), 120.71, 118.45, 72.56, 58.29, 43.92 (d, J=7 Hz), 42.32, 37.46, 33.52, 24.43, 19.9, 14.34. $^{19}$F NMR (376 MHz, $CDCl_3$): δ-132.1 (m). HRMS (ESI): calculated for $C_{25}H_{34}FNO_2$ $[M+H]^+$, 400.2646; found, 400.2648.

Scheme 3 General Method for Aminoketone Reduction

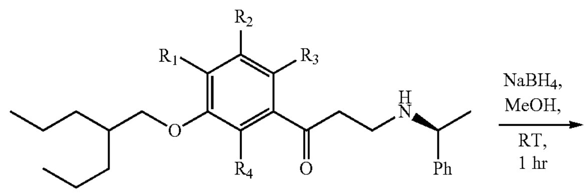

5: $R_2 = R_3 = R_4 = H, R_1 = F$
6: $R_1 = R_3 = R_4 = H, R_2 = F$
7: $R_1 = R_2 = R_4 = H, R_3 = F$
8: $R_1 = R_2 = R_3 = H, R_4 = F$

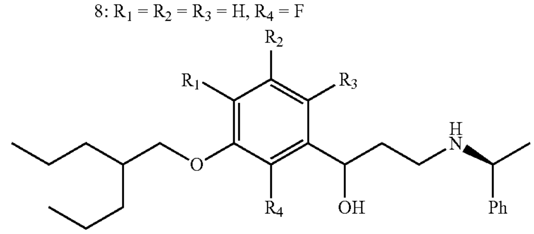

9: $R_2 = R_3 = R_4 = H, R_1 = F$
10: $R_1 = R_3 = R_4 = H, R_2 = F$
11: $R_1 = R_2 = R_4 = H, R_3 = F$
12: $R_1 = R_2 = R_3 = H, R_4 = F$

Sodium borohydride (3 mmol) was added in portions to a stirred solution of Mannich base (1 mmol) in MeOH (8 mL) at 0° C. and then warmed to room temperature. The reaction mixture was warmed spontaneously to room temperature and was stirred for 1 h before being quenched with a saturated aqueous solution of $NH_4Cl$ (10 mL). The white suspension was basified with saturated $NaHCO_3$, extracted with dichloromethane (5×25 mL), dried over $Na_2SO_4$ and concentrated under reduced pressure. The residue was purified by flash chromatography using $MeOH/CH_2Cl_2$ as an eluent to afford the desired aminoalcohol.

9

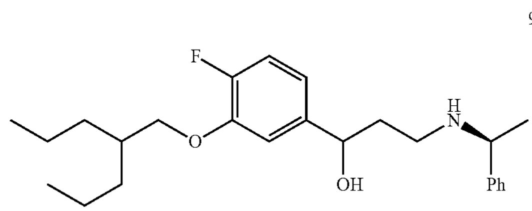

1-(4-Fluoro-3-((2-propylpentyl)oxy)phenyl)-3-(((S)-1-phenylethyl)amino)propan-1-ol (9):

The general synthesis was followed using (S)-1-(4-fluoro-3-((2-propylpentyl)oxy)phenyl)-3-((1-phenylethyl)amino) propan-1-one (5) (2.05 g, 5.15 mmol) to give a colorless oil (1.90 g, 92%) as a diastereomeric mixture $^1$H NMR (400 MHz, $CDCl_3$): δ 7.99-7.16 (m, 10H), 7.16-6.84 (m, 4H), 6.84-6.43 (m, 2H), 4.8 9 (dd, J=2.5, 8.5 Hz, 1H), 4.77 (dd, J=3, 8.5 Hz, 1H), 4-3.8 (m, 4H), 3.79-3.68 (m, 2H), 2.92-2.55 (m, 4H), 1.89-1.57 (m, 6H), 1.55-1.1 (m, 22H), 1.02-0.75 (m, 12H). $^{13}$C NMR (100 MHz, $CDCl_3$): δ 151.7 (d, J=244.5 Hz), 147.24 (d, J=10.5 Hz), 144.42, 144.29, 141.28, 141.25 (d, J=3.5 Hz), 128.7, 128.65, 127.32, 126.62, 126.47, 117.57, 117.50 (d, J=6.5 Hz), 115.53, 115.47 (d, J=18.5 Hz), 112.17, 75.31, 72.25, 72.33, 58.74, 58.53, 46.43, 46.35, 38.03, 37.97, 37.62, 33.64, 24.29, 23.49, 19.97, 14.43. $^{19}$F (376 MHz, $CDCl_3$): δ-137.85 (m). HRMS (ESI): calculated for $C_{25}H_{36}FNO_2$ $[M+Na]^+$, 424.2622; found, 424.2618.

All the chiral O-aminoketones 6-8 were similarly reduced with $NaBH_4$ to give the corresponding mixtures of diastereomeric γ-aminoalcohols 10-12 (57-90% yield in practically pure crude state). Each mixture of diastereomers was separated to single diastereomers by chiral HPLC.

Scheme 4 Synthesis and Separation of Diasteromeric Cyclic Carbamates 13 and 14

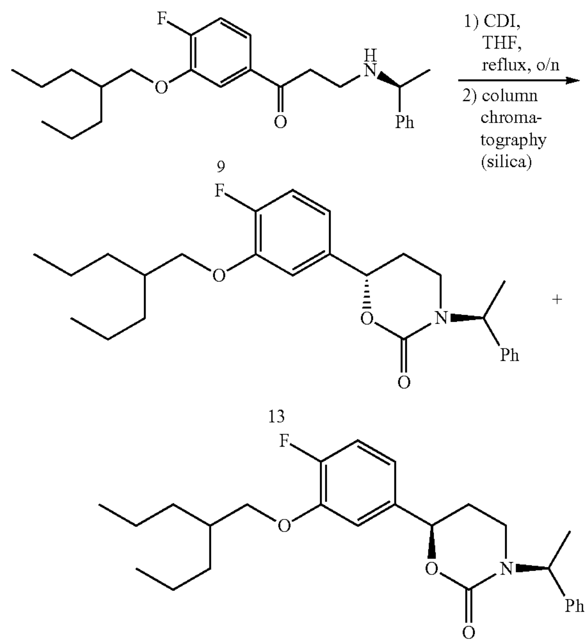

9

13

14

Carbonyldiimidazole (CDI) (218 mg, 1.34 mmol) was added to a stirred solution of 9 (270 mg, 0.67 mmol) in anhydrous THF (6 mL), and the reaction mixture was refluxed overnight under nitrogen. The solvent was then removed under reduced pressure, the remaining oil was dissolved in EtOAc (25 mL), washed with $H_2O$ (5×10 mL) and with brine (5 mL). The organic phase was dried over $Na_2SO_4$ and concentrated under reduced pressure. The diastereomeric cyclic carbamate were separated by flash chromatography using hexane/EtOAc to yield single diastereomers 13 (149 mg, 52%) and 14 (111 mg, 39%).

13

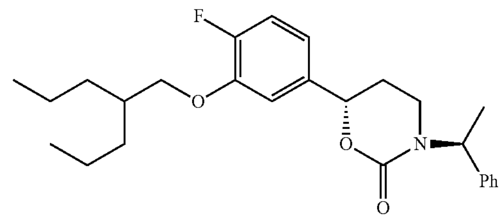

(S)-6-(4-Fluoro-3-((2-propylpentyl)oxy)phenyl)-3-((S)-1-phenylethyl)-1,3-oxazinan-2-one (13)

A colorless oil (0.149 g, 52%). $^1$H NMR (400 MHz, $CDCl_3$): δ 7.49-7.27 (m, 5H), 7.03 (dd, J=8.5, 10.5 Hz, 1H), 7-6.94 (m, 1H), 6.88-6.61 (m, 1H), 5.82 (q, J=7 Hz, 1H), 5.15 (dd, J=1.5, 10 Hz, 1H), 3.9 (d, J=5.5 Hz, 2H), 3.22-2.92 (m, 1H), 2.92-2.61 (m, 1H), 2.27-2.09 (m, 1H), 2.08-2 (m, 1H), 1.93-1.75 (m, 1H), 1.57 (d, J=7 Hz, 3H), 1.5-1.32 (m, 8H), 0.92 (t, J=7 Hz, 6H). $^{13}$C NMR (100 MHz, $CDCl_3$): δ 153.53, 152.49 (d, J=247 Hz), 147.72 (d, J=11 Hz), 139.46, 135.36 (d, J=3.5 Hz), 128.63, 127.74, 127.63, 117.69 (d, J=7 Hz), 115.97 (d, J=19 Hz), 112.22 (d, J=1.5 Hz), 77.4, 72.45, 53.67, 38.23, 37.61, 33.6, 29.77, 19.97, 15.10, 14.42. $^{19}$F NMR (376 MHz, $CDCl_3$): δ-135.2 (m). HRMS (ESI): calculated for $C_{26}H_{34}FNO_3$ $[M+K]^+$, 466.2154; found, 466.2158.

14

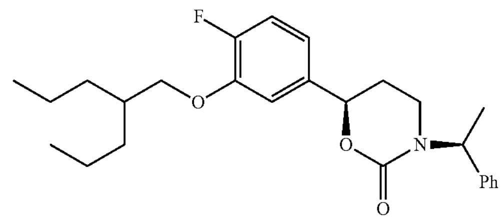

(R)-6-(4-fluoro-3-((2-propylpentyl)oxy)phenyl)-3-((S)-1-phenylethyl)-1,3-oxazinan-2-one (14)

A colorless oil (0.111 g, 39%). $^1$H NMR (400 MHz, $CDCl_3$): δ 7.46-7.18 (m, 5H), 7.17-6.92 (m, 2H), 6.92-6.65 (m, 1H), 5.87 (q, J=7 Hz, 1H), 5.15 (dd, J=1.5, 10 Hz, 1H), 3.9 (d, J=5.5 Hz, 2H), 3.52-3.13 (m, 1H), 3.11-2.66 (m, 1H), 2.32-2.05 (m, 1H), 1.97-1.78 (m, 2H), 1.60 (d, J=7 Hz, 3H), 1.52-1.31 (m, 8H), 0.92 (t, J=7 Hz, 6H). $^{13}$C NMR (100 MHz, $CDCl_3$): δ 153.63, 152.50 (d, J=247 Hz), 147.69 (d, J=11 Hz), 139.88, 135.35 (d, J=3.5 Hz), 128.57, 127.62, 127.21, 117.80 (d, J=7 Hz), 115.92 (d, J=19 Hz), 112.27 (d, J=1.5 Hz), 77.7, 72.43, 53.38, 38.22, 37.60, 33.60, 29.67, 19.97, 15.68, 14.42. $^{19}$F NMR (376 MHz, $CDCl_3$): δ-135.2 (m). HRMS (ESI): calculated for $C_{26}H_{34}FNO_3$ $[M+K]^+$, 466.2154; found, 466.2158.

Scheme 5 Hydrolysis of Cyclic Carbamates 13 and 14

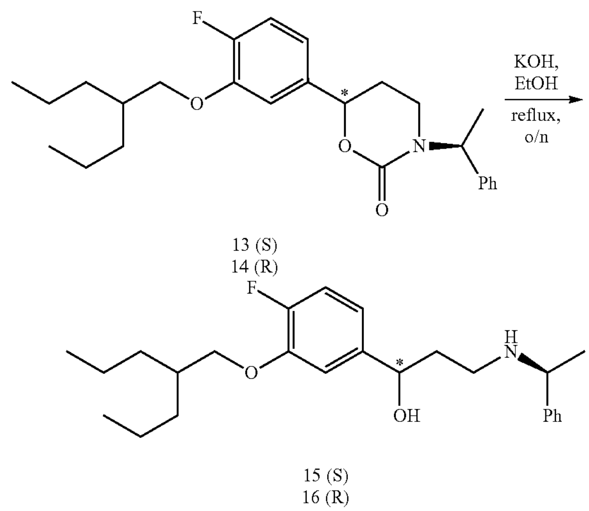

13 (S)
14 (R)

15 (S)
16 (R)

An aqueous solution of potassium hydroxide (8 M, 25 mL) was added to a stirred solution carbamate 13 (644 mg, 1.5 mmol) in EtOH (25 mL) and refluxed overnight. The reaction mixture was concentrated under reduced pressure to a half of the original volume, extracted with dichloromethane (5×10 mL), washed with water (2×10 mL) and with brine (10 mL). The organic phase was dried over $Na_2SO_4$ and concentrated under reduced pressure to give practically pure protected aminoalcohol 15 (560 mg, 93%) as a colorless oil.

15

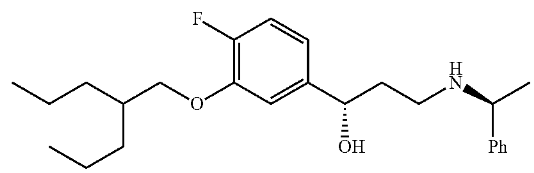

(S)-1-(4-fluoro-3-((2-propylpentyl)oxy)phenyl)-3-(((S)-1-phenylethyl)amino)propan-1-ol (15)

A colorless oil (560 mg, 93%). $^1$H NMR (400 MHz, $CDCl_3$): δ 7.57-7.16 (m, 5H), 7.11-6.97 (m, 1H), 6.93 (dd, J=8.5, 11 Hz, 1H), 6.83-6.59 (m, 1H), 4.86 (dd, J=2.5, 8.5 Hz, 1H), 3.87 (d, J=5.5 Hz, 2H), 3.71 (q, J=6.5 Hz, 1H), 3.1-2.4 (m, 2H), 1.97-1.7 (m, 2H), 1.69-1.56 (m, 1H), 1.52-1.24 (m, 11H), 0.91 (t, J=6.5 Hz, 6H). $^{13}$C NMR (100 MHz, $CDCl_3$): δ 151.66 (d, J=244.5 Hz), 147.21 (d, J=10.5 Hz), 144.5, 141.37, 128.61, 127.27, 126.45, 117.57, 115.44 (d, J=18.5 Hz), 112.19, 75.10, 72.28, 58.7, 46.26, 38.02, 37.61, 33.64, 23.5, 19.96, 14.42. $^{19}$F NMR (376 MHz, $CDCl_3$): δ-137.52 (m). HRMS (ESI): calculated for $C_{25}H_{36}FNO_2$ $[M+Na]^+$, 424.2622; found, 424.2617.

16

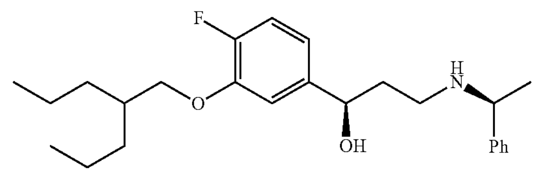

(R)-1-(4-Fluoro-3-((2-propylpentyl)oxy)phenyl)-3-(((S)-1-phenylethyl)amino)propan-1-ol (16)

As above, alkaline hydrolysis of cyclic carbamate 14 (690 mg, 1.61 mmol) afforded practically pure N-protected aminoalcohol 16 (648 mg, 71%) as a colorless oil. $^1$H NMR (400 MHz, $CDCl_3$): δ 7.43-7.16 (m, 5H), 7.08-7 (m, 1H), 6.96 (dd, J=8.5, 11 Hz, 1H), 6.8-6.71 (m, 1H), 4.74 (dd, J=3, 8.5 Hz, 1H), 3.90 (d, J=5.5 Hz, 2H), 3.72 (q, J=6.5 Hz, 1H), 2.97-2.68 (m, 1H), 2.68-2.4 (m, 1H), 1.89-1.79 (m, 1H), 1.77-1.66 (m, 2H), 1.51-1.29 (m, 11H), 0.91 (t, J=6.5 Hz, 6H). $^{13}$C NMR (100 MHz, $CDCl_3$): δ 151.68 (d, J=244.5 Hz), 147.23 (d, J=10.5 Hz), 144.42, 141.39 (d, J=3.5 Hz), 128.66, 127.25, 126.60, 117.53 (d, J=6.5 Hz), 115.49 (d, J=18.5 Hz), 112.19, 75.16, 72.29, 58.49, 46.36, 38.12, 37.61, 33.65, 24.28, 19.97, 14.44. [19]F (376 MHz, $CDCl_3$): δ-137.70 (m). HRMS (ESI): calculated for $C_{25}H_{36}FNO_2$ $[M+Na]^+$, 424.2622; found, 424.2620.

Chiral HPLC Separation of N-Methylbenzylamine-Protected Alcohols:

All mixtures of diastereomeric γ-aminoalcohols 10-12 were separated using a Lux 5 μm Amylose-1, AXIA Packed 250×21.2 mm chiral column using the conditions described below:

Condition 1: isocratic mixture of hexane/EtOAc (95:5)+0.1% diethylamine (DEA), flow rate of 13 mL/min.

Condition 2: an isocratic mixture of hexane/EtOAc (98:2)+0.4% DEA, flow rate of 13 mL/min.

Condition 3: an isocratic mixture of hexane/EtOAc (98:2)+0.1% DEA, flow rate of 13 mL/min.

17/18

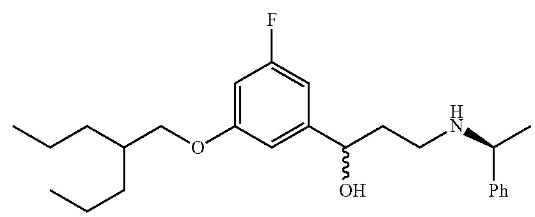

(S/R)-1-(3-Fluoro-5-((2-propylpentyl)oxy)phenyl)-3-(((S)-1-phenylethyl)amino)propan-1-ol (17/181)

According to the general method for reduction of aminoketones, (S)-1-(3-fluoro-5-((2-propylpentyl)oxy)phenyl)-3-((1-phenylethyl)amino)propan-1-one (6) (604 mg, 1.51 mmol) was converted to a mixture of diastereomeric N-protected γ-aminoalcohols 10. The mixture was separated to single diastereomers 17 (178.0 mg, 29%) and 18 (151.6 mg, 25%) by chiral HPLC (Conditions 1).

17: A colorless oil (Condition 1, 178.03 mg, 29%). $^1$H NMR (300 MHz, $CDCl_3$): δ 7.47-7.27 (m, 5H), 6.8-6.68 (m, 1H), 6.68-6.56 (m, 1H), 6.47 (dt, J=2.5, 10.5 Hz, 1H), 4.79 (dd, J=3, 8.5 Hz, 1H), 3.83-3.74 (m, 3H), 2.95-2.8 (m, 1H), 2.76-2.63 (m, 1H), 1.95-1.49 (m, 3H), 1.45-1.3 (m, 11H), 0.91 (t, J=7 Hz, 6H). $^{13}C$ NMR (75 MHz, $CDCl_3$) δ 163.58 (d, J=244 Hz), 160.63 (d, J=11.5 Hz), 148.14 (d, J=8.5 Hz), 143.77, 128.75, 127.45, 126.67, 107.35 (d, J=2 Hz), 104.45 (d, J=22 Hz), 100.52 (d, J=25 Hz), 75.05, 71.14, 58.49, 46.12, 37.48, 37.38, 33.7, 24.04, 19.99, 14.43. $^{19}F$ NMR (376 MHz, $CDCl_3$): δ-112.80 (t, J=10 Hz). HRMS (ESI): calculated for $C_{25}H_{36}FNO_2$ $[M+H]^+$, 402.2802; found, 402.2809.

18: A colorless oil (Condition 1, 151.63 mg, 25%). $^1H$ NMR (300 MHz, $CDCl_3$): δ 7.41-7.21 (m, 5H), 6.81-6.65 (m, 1H), 6.65-6.55 (m, 1H), 6.44 (dt, J=2.5, 10.5 Hz, 1H), 4.89 (dd, J=3, 8.5 Hz, 1H), 3.8-3.71 (m, 3H), 2.97-2.59 (m, 2H), 2.04-1.85 (m, 1H), 1.85-1.71 (m, 1H), 1.71-1.55 (m, 1H), 1.62-1.27 (m, 11H), 0.91 (t, J=7 Hz, 6H). $^{13}C$ NMR (75 MHz, $CDCl_3$) δ 163.54 (d, J=244 Hz), 160.59 (d, J=11.5 Hz), 148.26 (d, J=8.5 Hz), 144.09, 128.68, 127.41, 126.48, 107.43 (d, J=2 Hz), 104.51 (d, J=22 Hz), 100.37 (d, J=25 Hz), 75.08, 71.1, 58.69, 46.05, 37.5, 37.39, 33.7, 23.47, 20, 14.43. $^{19}F$ NMR (376 MHz, $CDCl_3$): δ-112.75 (t, J=10 Hz). HRMS (ESI): calculated for $C_{25}H_{36}FNO_2$ $[M+H]^+$, 402.2802; found, 402.2807.

19/20

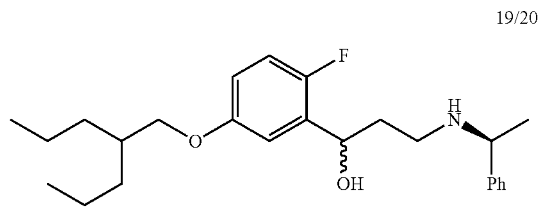 [SMILES: CCCC(CCC)COc1ccc(F)c(C(O)CCN[C@@H](C)c2ccccc2)c1]

(S/R)-1-(2-fluoro-5-((2-propylpentyl)oxy)phenyl)-3-(((S)-1-phenylethyl)amino)propan-1-ol (19/20)

According to the general method for reduction of aminoketones, (S)-1-(2-fluoro-5-((2-propylpentyl)oxy)phenyl)-3-((1-phenylethyl)amino)propan-1-one (7) (1.47 g, 3.68 mmol) was converted to a mixture of diastereomeric N-protected γ-aminoalcohols 11. The mixture was separated to single diastereomers 19 (335.3 mg, 23%) and 20 (324.9 mg, 22%) by chiral HPLC (Conditions 3).

19: A yellowish oil. $^1H$ NMR (400 MHz, $CDCl_3$): δ 7.77-7.60 (m, 1H), 7.16-6.99 (m, 5H), 6.87-6.76 (m, 1H), 6.71-6.55 (m, 1H), 5.32 (d, J=8.5 Hz, 1H), 3.73 (d, J=5 Hz, 2H), 3.34 (q, J=6.5 Hz, 1H), 2.47-2.33 (m, 2H), 1.92-1.77 (m, 1H), 1.77-1.66 (m, 1H), 1.66-1.51 (m, 1H), 1.45-1.22 (m, 8H), 1.06 (d, J=6.5 Hz, 3H), 0.87 (t, J=7 Hz, 6H). $^{13}C$ NMR (100 MHz, $CDCl_3$) δ 156.35, 155.23 (d, J=237 Hz), 144.85, 134.07 (d, J=15 Hz), 128.85, 127.4, 126.80, 115.63 (d, J=23.5 Hz), 114.01 (d, J=7.5 Hz), 113.36 (d, J=4 Hz), 71.39, 70.06, 58.45, 46.48, 38, 36.96, 34.11, 24.2, 20.34, 14.65. $^{19}F$ NMR (376 MHz, $CDCl_3$): δ-131.2 (m). HRMS (ESI): calculated for $C_{25}H_{36}FNO_2$ $[M+H]^+$, 402.2802; found, 402.2807.

20: A colorless oil. $^1H$ NMR (400 MHz, $CDCl_3$): δ 7.6 (dd, J=3, 6 Hz, 1H), 7.16-6.97 (m, 5H), 6.91-6.75 (m, 1H), 6.68-6.51 (m, 1H), 5.41 (dd, J=2, 8.5 Hz, 1H), 3.70 (d, J=5.5 Hz, 2H), 3.31 (q, J=6.5 Hz, 1H), 2.5-2.28 (m, 2H), 1.94-1.79 (m, 1H), 1.78-1.64 (m, 1H), 1.57-1.47 (m, 1H), 1.44-1.23 (m, 8H), 1.13-1.06 (d, J=6.5 Hz, 3H), 0.88 (t, J=7 Hz, 6H). $^{13}C$ NMR (100 MHz, $CDCl_3$) δ 156.32, 154.21 (d, J=235.5 Hz), 145.12, 134.13 (d, J=15 Hz), 128.74, 127.28, 126.67, 115.56 (d, J=23.5 Hz), 113.91 (d, J=7.5 Hz), 113.44 (d, J=4.5 Hz), 71.34, 69.81, 58.64, 46.46, 38.01, 37.14, 34.09, 23.54, 20.35, 14.64. $^{19}F$ NMR (376 MHz, $CDCl_3$): δ-131.2 (m). HRMS (ESI): calculated for $C_{25}H_{36}FNO_2$ $[M+H]^+$, 402.2802; found, 402.2811.

21/22

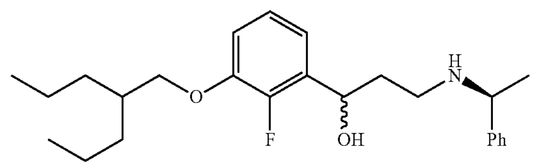

(S/R)-1-(2-fluoro-3-((2-propylpentyl)oxy)phenyl)-3-(((S)-1-phenylethyl)amino)propan-1-ol (21/22)

According to the general method for reduction of aminoketones, (S)-1-(2-fluoro-3-((2-propylpentyl)oxy)phenyl)-3-((1-phenylethyl)amino)propan-1-one (8) (0.78 g, 1.95 mmol) was converted to a mixture of diastereomeric N-protected γ-aminoalcohols 12. The mixture was separated to single diastereomers 21 (220.9 mg, 28%) and 22 (166.2 mg, 21%) by chiral HPLC (Conditions 2).

21: A yellowish oil: $^1H$ NMR (400 MHz, $C_6D_6$): δ 7.49-7.37 (m, 1H), 7.16-7 (m, 5H), 7-6.90 (m, 1H), 6.67 (td, J=1, 8 Hz, 1H), 5.45 (dd, J=2.5, 8 Hz, 1H), 3.67 (d, J=5.5 Hz, 2H), 3.27 (q, J=6.5 Hz, 1H), 2.50-2.20 (m, 2H), 1.88-1.77 (m, 1H), 1.77-1.69 (m, 1H), 1.62-1.50 (m, 1H), 1.46-1.22 (m, 8H), 1.09 (d, J=6.5 Hz, 3H), 0.87 (t, J=7 Hz, 6H). $^{13}C$ NMR (100 MHz, $C_6D_6$): δ 150.06 (d, J=244.5 Hz), 147.59 (d, J=11 Hz), 145.12, 134.37 (d, J=10.5 Hz), 128.72, 127.29, 126.86, 123.82 (d, J=4 Hz), 119.33 (d, J=3 Hz), 113.29, 72.29, 69.56 (d, J=2.5 Hz), 58.73, 46.14, 38, 36.95, 34.02, 23.56, 20.32, 14.62. $^{19}F$ NMR (376 MHz, $C_6D_6$): δ −142.12 (t, J=7.1 Hz). HRMS (ESI): calculated for $C_{25}H_{36}FNO_2$ $[M+H]^+$, 402.2802; found, 402.2807.

22: A yellowish oil: $^1H$ NMR (400 MHz, $C_6D_6$): δ 7.64-7.53 (m, 1H), 7.15-7.05 (m, 5H), 7.05-6.95 (m, 1H), 6.69 (td, J=1, 8 Hz, 1H), 5.34 (dd, J=2, 9 Hz, 1H), 3.68 (d, J=5.5 Hz, 2H), 3.33 (q, J=6.5 Hz, 1H), 2.45-2.3 (m, 2H), 1.83-1.68 (m, 2H), 1.68-1.53 (m, 1H), 1.49-1.2 (m, 8H), 1.07 (d, J=6.5 Hz, 3H), 0.87 (t, J=7 Hz, 6H). $^{13}C$ NMR (100 MHz, $C_6D_6$): δ 150.16 (d, J=244.5 Hz), 147.67 (d, J=10.5 Hz), 144.96, 134.39 (d, J=10.5 Hz), 128.81, 127.34, 126.81, 123.89 (d, J=4 Hz), 119.21 (d, J=3 Hz), 113.39, 72.33, 69.89, 58.51, 46.35, 37.98, 36.95, 34.01, 24.17, 20.31, 14.61. $^{19}F$ NMR (376 MHz, $C_6D_6$): δ-141.76 (t, J=6.9 Hz). HRMS (ESI): calculated for $C_{25}H_{36}FNO_2$ $[M+H]^+$, 402.2802; found, 402.2806.

Scheme 6 General Route for Deprotection of (S)-Methylbenzylaminoalcohols[2]

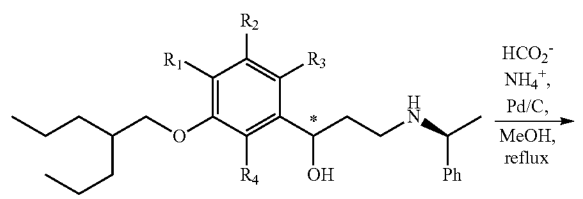

15: $R_2 = R_3 = R_4 = H, R_1 = F$ (S)
17: $R_1 = R_3 = R_4 = H, R_2 = F$ (S/R)
19: $R_1 = R_2 = R_4 = H, R_3 = F$ (S/R)
21: $R_1 = R_2 = R_3 = H, R_4 = F$ (S/R)

16: $R_2 = R_3 = R_4 = H, R_1 = F$ (R)
18: $R_1 = R_3 = R_4 = H, R_2 = F$ (S/R)
20: $R_1 = R_2 = R_4 = H, R_3 = F$ (S/R)
22: $R_1 = R_2 = R_3 = H, R_4 = F$ (S/R)

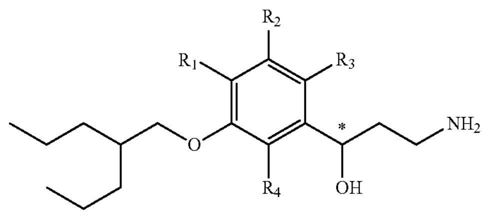

23: $R_2 = R_3 = R_4 = H, R_1 = F$ (S)
25: $R_1 = R_3 = R_4 = H, R_2 = F$ (S/R)
28: $R_1 = R_2 = R_4 = H, R_3 = F$ (S/R)
30: $R_1 = R_2 = R_3 = H, R_4 = F$ (S/R)

24: $R_2 = R_3 = R_4 = H, R_1 = F$ (R)
26: $R_1 = R_3 = R_4 = H, R_2 = F$ (S/R)
27: $R_1 = R_2 = R_4 = H, R_3 = F$ (S/R)
29: $R_1 = R_2 = R_3 = H, R_4 = F$ (S/R)

The N-protected aminoalcohol 15-22 (0.74 mmol) was suspended with 10% Pd/C (0.1 g) in dry MeOH (4 mL) under a nitrogen atmosphere. After 30 min, solid ammonium formate (1.29 mmol) was added. The resulting mixture was refluxed for 30 min—overnight and then cooled to 0° C., filtrated through a celite pad and washed with chloroform. The filtrate was concentrated under reduced pressure to afford the corresponding γ-hydroxyamines 23-30.

23

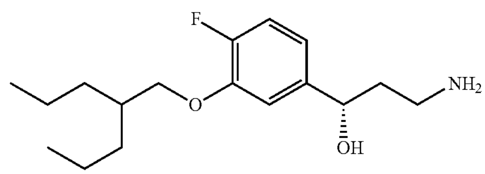

(S)-3-Amino-1-(4-fluoro-3-((2-propylpentyl)oxy) phenyl)propan-1-ol (23)

According to general procedure, N-benzylated compound 15 (280 mg, 0.70 mmol) was deprotected to give the title γ-aminoalcohol 23 (188 mg, 91%) as a colorless oil. $^1H$ NMR (300 MHz, $CDCl_3$): δ 7.23-6.85 (m, 2H), 6.8 (ddd, J=2, 4, 8 Hz, 1H), 4.82 (dd, J=3, 8.5 Hz, 1H), 3.89 (d, J=5.5 Hz, 2H), 3.64 (bs, 2H), 3.37-2.96 (m, 1H), 2.96-2.59 (m, 1H), 2.07-1.57 (m, 3H), 1.56-1.19 (m, 8H), 0.91 (t, J=7 Hz, 6H). $^{13}C$ NMR (75 MHz, $CDCl_3$): δ 151.75 (d, J=244.5 Hz), 147.29 (d, J=10.5 Hz), 141.43 (d, J=3.5 Hz), 117.59 (d, J=7 Hz), 115.56 (d, J=18.5 Hz), 112.25, 74.33, 72.34, 40.11, 39.82, 37.62, 33.62, 19.97, 14.44. $^{19}F$ NMR (376 MHz, $CDCl_3$): δ-137.5 (m). HRMS (ESI): calculated for $C_{17}H_{28}FNO_2$ $[M+H]^+$, 298.2176; found, 298.2172.

24

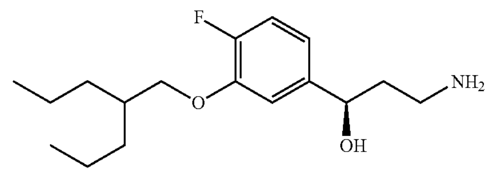

(R)-3-Amino-1-(4-fluoro-3-((2-propylpentyl)oxy) phenyl)propan-1-ol (24)

According to general procedure, N-benzylated compound 16 (458 mg, 1.14 mmol) was deprotected to give the title γ-aminoalcohol 24 (314.2 mg, 93%) as a colorless oil. $^1H$ NMR (400 MHz, $CDCl_3$): δ 7.06-6.94 (m, 2H), 6.9-6.7 (m, 1H), 4.82 (dd, J=3, 8.5 Hz, 1H), 3.89 (d, J=5.5 Hz, 2H), 3.5 (bs, 2H), 3.2-3.02 (m, 1H), 3-2.9 (m, 1H), 1.89-1.80 (m, 2H), 1.78-1.68 (m, 1H), 1.49-1.2 (m, 8H), 0.91 (t, J=7 Hz, 6H). $^{13}C$ NMR (100 MHz, $CDCl_3$): δ 151.81 (d, J=244.5 Hz), 147.32 (d, J=10.5 Hz), 141.29 (d, J=3.5 Hz), 117.60 (d, J=7 Hz), 115.61 (d, J=18.5 Hz), 112.33, 74.73, 72.41, 40.27, 39.44, 37.63, 33.64, 19.98, 14.43. $^{19}F$ NMR (376 MHz, $CDCl_3$): δ-137.5 (m). HRMS (ESI): calculated for $C_{17}H_{28}FNO_2$ $[M+H]^+$, 298.2176; found, 298.2173.

25/26

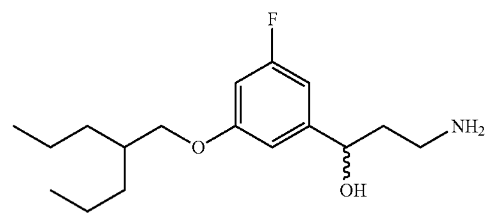

(S/R)-3-amino-1-(3-fluoro-5-((2-propylpentyl)oxy) phenyl)propan-1-ol (25/26)

According to general procedure, N-benzylated compound 17 (236 mg, 0.59 mmol) was deprotected giving the chiral γ-aminoalcohol 25 (170 mg, 97%) as a colorless oil.

$^1H$ NMR (600 MHz, $C_6D_6$): δ 7.10-7.02 (m, 1H), 6.99-6.85 (m, 1H), 6.68-6.54 (m, 1H), 5.14-4.61 (m, 1H), 3.56 (d, J=5.5 Hz, 2H), 2.5-2.35 (m, 1H), 2.34-2.14 (m, 1H), 1.7-1.62 (m, 1H), 1.49-1.19 (m, 10H), 0.87 (t, J=7 Hz, 6H). $^{13}C$ NMR (150 MHz, $C_6D_6$): δ 164.38 (d, J=244 Hz), 161.22 (d, J=11 Hz), 150.08 (d, J=8.5 Hz), 108.36 (d, J=2.5 Hz), 105 (d, J=22 Hz), 100.37 (d, J=25 Hz), 75.11, 70.97, 40.72, 39.71, 37.84, 34.03, 20.32, 14.64. $^{19}F$ NMR (376 MHz, $C_6D_6$): δ-112.89 (t, J=10 Hz). HRMS (ESI): calculated for $C_{17}H_{28}FNO_2$ $[M+H]^+$, 298.2176; found, 298.2179.

Deprotection of N-benzylated compound 18 (46 mg, 0.11 mmol) according to general procedure afforded the chiral γ-aminoalcohol 26 (14.2 mg, 42%) as a colorless oil.

$^{1}$H NMR (400 MHz, $CDCl_3$+$CD_3OD$): a 6.72-6.67 (m, 1H), 6.67-6.59 (m, 1H), 6.54-6.43 (m, 1H), 4.76 (dd, J=4, 8 Hz, 1H), 3.80 (d, J=5.5 Hz, 2H) 3.77 (bs, 2H), 3.07-2.70 (m, 2H), 1.86-1.73 (m, 3H), 1.5-1.24 (m, 8H), 0.91 (t, J=7 Hz, 6H). $^{13}$C NMR (100 MHz, $CDCl_3$+$CD_3OD$): a 162.71 (d, J=244 Hz), 160.79 (d, J=11 Hz), 148.25 (d, J=8.5 Hz), 107.78 (d, J=2.5 Hz), 104.55 (d, J=22 Hz), 100.65 (d, J=25 Hz), 73.19, 71.32, 40.02, 39.22, 37.57, 33.77, 20.06, 14.44. $^{19}$F (376 MHz, $CDCl_3$+$CD_3OD$): δ-112.74 (t, J=10 Hz). HRMS (ESI): calculated for $C_{17}H_{28}FNO_2$ $[M+H]^+$, 298.2176; found, 298.2186.

27/28

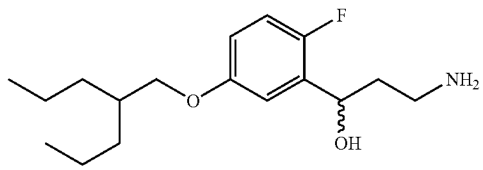

(S/R)-3-amino-1-(2-fluoro-5-((2-propylpentyl)oxy) phenyl)propan-1-ol (27/28)

According to general procedure, N-benzylated compound 20 (30 mg, 0.07 mmol) was deprotected giving the chiral γ-aminoalcohol 27 (13.4 mg, 61%) as a colorless oil.

$^{1}$H NMR (400 MHz, $C_6D_6$): δ 7.69 (dd, J=6 Hz, J=1, 3 Hz, 1H), 6.83 (t, J=9.5 Hz, 1H), 6.70-6.58 (m, 1H), 5.42 (dd, J=1, 8.5 Hz, 1H), 3.70 (d, J=5.5 Hz, 2H), 2.51-2.4 (m, 1H), 2.37-2.29 (m, 1H), 1.84-1.76 (m, 1H), 1.75-1.65 (m, 1H), 1.54-1.45 (m, 1H), 1.44-1.21 (m, 8H), 0.87 (t, J=7 Hz, 6H). $^{13}$C NMR (100 MHz, $C_6D_6$): δ 156.41, 154.23 (d, J=236 Hz), 134.33 (d, J=14.5 Hz), 115.61 (d, J=23.5 Hz), 114.02 (d, J=8 Hz), 113.41 (d, J=4.5 Hz), 71.35, 70.11, 41, 38.61, 38.02, 34.1, 20.36, 14.66. $^{19}$F NMR (376 MHz, $C_6D_6$): 6-131.25 (m). HRMS (ESI): calculated for $C_{17}H_{28}FNO_2$ $[M+H]^+$, 298.2176; found, 298.2178.

Following the general procedure, N-benzylated compound 19 (33 mg, 0.08 mmol) was deprotected giving the chiral γ-aminoalcohol 27 (15.2 mg, 61%) as a colorless oil. $^{1}$H NMR (700 MHz, $C_6D_6$): δ 7.71 (dd, J=3, 6 Hz, 1H), 6.83 (t, J=9.5 Hz, 1H), 6.71-6.56 (m, 1H), 5.43 (dd, J=1, 8.5 Hz, 1H), 3.70 (d, J=5.5 Hz, 2H), 2.52-2.37 (m, 1H), 2.37-2.29 (m, 1H), 1.85-1.75 (m, 1H), 1.75-1.63 (m, 1H), 1.51-1.43 (m, 1H), 1.43-1.20 (m, 8H), 0.86 (t, J=7 Hz, 6H). $^{13}$C NMR (176 MHz, $C_6D_6$): a 156.39, 154.22 (d, J=236 Hz), 134.33 (d, J=14.5 Hz), 115.61 (d, J=23.5 Hz), 114.01 (d, J=8 Hz), 113.38 (d, J=4.5 Hz), 71.31, 70.22, 41.07, 38.56, 38.01, 34.08, 20.35, 14.66. $^{19}$F NMR (376 MHz, $C_6D_6$): δ-131.25 (m). HRMS (ESI): calculated for $C_{17}H_{28}FNO_2$ $[M+H]^+$, 298.2176; found, 298.2177.

29/30

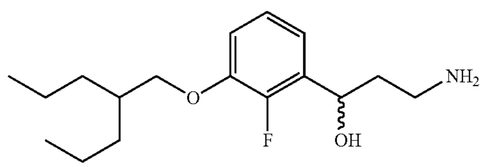

(S/R)-3-amino-1-(2-fluoro-3-((2-propylpentyl)oxy) phenyl)propan-1-ol (29/30)

According to general procedure, N-benzylated compound 22 (36 mg, 0.09 mmol) was deprotected to give the chiral γ-aminoalcohol 29 (14.1 mg, 52%) as a colorless oil. $^{1}$H NMR (700 MHz, $C_6D_6$): a 7.60 (t, J=8 Hz, 1H), 7.07 (t, J=8 Hz, 1H), 6.68 (t, J=1, 8 Hz, 1H), 5.44 (dd, J=2, 8.5 Hz, 1H), 3.68 (d, J=2, 5.5 Hz, 2H), 2.45-2.39 (m, 1H), 2.33-2.29 (m, 1H), 1.8-1.7 (m, 2H), 1.55-1.47 (m, 1H) 1.46-1.23 (m, 8H), 0.88 (t, J=7 Hz, 6H). $^{13}$C NMR (176 MHz, $C_6D_6$): δ 150.09 (d, J=244.5 Hz), 147.64 (d, J=11 Hz), 134.62 (d, J=10.5 Hz), 123.92 (d, J=4 Hz), 119.31 (d, J=3.5 Hz), 113.24, 72.24, 69.87 (d, J=2.5 Hz), 40.83, 38.56, 38, 34.02, 20.33, 14.64. $^{19}$F NMR (376 MHz, $C_6D_6$): 6-142.05 (t, J=7 Hz). HRMS (ESI): calculated for $C_{17}H_{28}FNO_2$ $[M+H]^+$, 298.2176; found, 298.2187.

Following the general procedure, N-benzylated compound 21 (35 mg, 0.09 mmol) was deprotected giving the chiral γ-aminoalcohol 30 (13.6 mg, 52%) as a colorless oil. $^{1}$H NMR (400 MHz, $C_6D_6$): δ 7.60 (t, J=1, 8 Hz, 1H), 7.01 (t, J=8 Hz, 1H), 6.69 (t, J=8 Hz, 1H), 5.44 (dd, J=2, 8.5 Hz, 1H), 3.68 (d, J=5.5 Hz, 2H), 2.45-2.38 (m, 1H), 2.34-2.27 (m, 1H), 1.82-1.69 (m, 2H), 1.54-1.48 (m, 1H) 1.46-1.21 (m, 8H), 0.88 (t, J=7 Hz, 6H). $^{13}$C NMR (100 MHz, $C_6D_6$): δ 150.12 (d, J=244.5 Hz), 147.65 (d, J=11 Hz), 134.65 (d, J=10.5 Hz), 123.92 (d, J=4 Hz), 119.32 (d, J=3.5 Hz), 113.26, 72.27, 69.87 (d, J=2.5 Hz), 40.85, 38.63, 38.01, 34.03, 20.33, 14.63. $^{19}$F (376 MHz, $C_6D_6$): δ-142.11 (t, J=7 Hz). HRMS (ESI): calculated for $C_{17}H_{28}FNO_2$ $[M+H]^+$, 298.2176; found, 298.2178.

Synthesis of Cyclohexyl and 2,6,6-trimethylcyclohexenyl Families of γ-hydroxyamines Scheme 7 Synthesis of Fluorinated Benzaldehydes

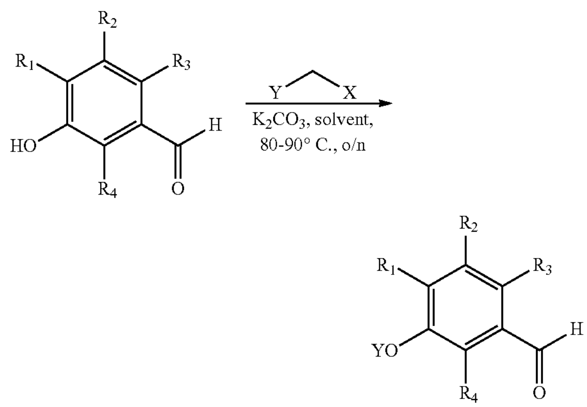

Y =

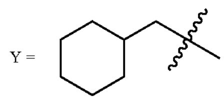

31: $R_2$ = $R_3$ = $R_4$ = H, $R_1$ = F
32: $R_1$ = $R_3$ = $R_4$ = H, $R_2$ = F
33: $R_1$ = $R_2$ = $R_4$ = H, $R_3$ = F
34: $R_1$ = $R_2$ = $R_3$ = H, $R_4$ = F

-continued

Y = 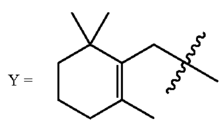

35: $R_2 = R_3 = R_4 = H, R_1 = F$
36: $R_1 = R_3 = R_4 = H, R_2 = F$
37: $R_1 = R_2 = R_4 = H, R_3 = F$
38: $R_1 = R_2 = R_3 = H, R_4 = F$

Y = 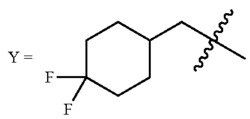

39: $R_1 = R_2 = R_3 = R_4 = H$

Synthesis A: Cyclohexyl Family

31

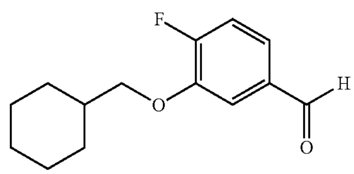

Synthesis of 3-(cyclohexylmethoxy)-4-fluorobenzaldehyde (31)

To a mixture of 4-fluoro-3-hydroxybenzaldehyde (5.0 g, 35.7 mmol, 1.0 eq) in NMP (35 mL) were added potassium carbonate (6.16 g, 44.6 mmol, 1.25 eq) and (bromomethyl) cyclohexane (6.95 g, 39.2 mmol, 1.1 eq). The resulting mixture was stirred at 75° C. for about 12 h. The reaction was quenched by pouring the reaction mixture into ice-water (200 mL). Then the product was extracted with ethyl acetate (3×50 mL). The combined organic layers were washed with sodium hydroxide solution (1 M, 2×50 mL), and brine (50 mL) separately. The resulting solution was dried over anhydrous magnesium sulfate, filtered, and concentrated under reduced pressure to give a yellow oil (6.7 g, 79%). This molecule was used in the subsequent step without further characterization. $^1$H NMR ($CDCl_3$, 400 MHz) δ 9.89 (s, 1H), 7.47 (dd, J=8.11, 1.97 Hz, 1H), 7.41 (ddd, J=8.11, 4.39, 1.97 Hz, 1H), 7.21 (dd, J=10.52, 8.33 Hz, 1H), 3.87 (d, J=6.14 Hz, 2H), 1.66-1.94 (m, 6H), 1.02-1.40 (m, 5H).

32

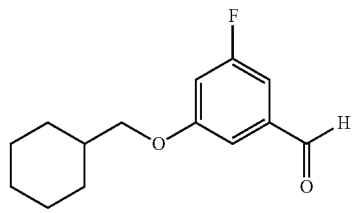

3-(cyclohexylmethoxy)-5-fluorobenzaldehyde (32)

General Synthesis A was followed using 5-fluoro-3-hydroxybenzaldehyde (5.0 g, 35.6 mmol) to give a yellow oil (5.4 g, 70%). This molecule was used in the subsequent step without further characterization.

33

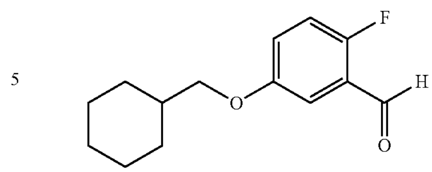

5-(cyclohexylmethoxy)-2-fluorobenzaldehyde (33)

General Synthesis A: 2-fluoro-5-hydroxybenzaldehyde (7.0 g, 49.9 mmol) afforded a yellow oil (6.4 g, 60%). This molecule was used in the subsequent step without further characterization. $^1$H NMR ($CDCl_3$, 400 MHz) δ 10.31 (s, 1H), 7.27-7.24 (m, 1H), 7.14-7.03 (m, 2H), 3.74 (d, J=6.4 Hz, 2H), 1.88-1.63 (m, 6H), 1.35-1.12 (m, 3H), 1.08-0.95 (n, 2H).

34

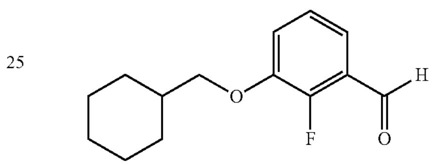

3-(cyclohexylmethoxy)-2-fluorobenzaldehyde (34)

General Synthesis A: 2-fluoro-3-hydroxybenzaldehyde (5.0 g, 35.7 mmol) yielded aldehyde 34 (6.41 g, 76%) as a white solid. This molecule was used in the subsequent step without further characterization. $^1$H NMR ($CDCl_3$, 400 MHz) δ 10.38 (s, 1H), 7.39 (ddd, J=7.55, 5.68, 1.98 Hz, 1H), 7.10-7.22 (m, 2H), 3.85 (d, J=6.17 Hz, 2H), 1.66-1.95 (m, 6H), 0.99-1.40 (m, 5H).

Synthesis B: 2,6,6-trimethylcyclohexenyl Family

35

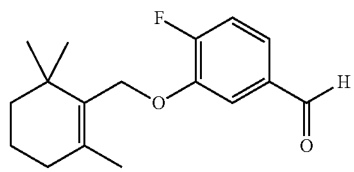

Synthesis of 4-fluoro-3-((2,6,6-trimethylcyclohex-1-en-1-yl)methoxy)benzaldehyde (35)

To a mixture of compound 4-fluoro-3-hydroxybenzaldehyde (5.68 g, 40.5 mmol, 1.1 eq) in NMP (50 mL) were added potassium carbonate (6.6 g, 47.7 mmol, 1.25 eq) and 2,6,6-trimethylcyclohexenylbromide (8 g, 36.8 mmol, 1.0 eq). The resulting mixture was degassed and purged with nitrogen for 3 times, then stirred at 75° C. for about 16 h under nitrogen. The reaction was quenched by pouring the reaction mixture into ammonium chloride solution (5%, 100 mL). Then the product was extracted with ethyl acetate (3×100 mL). The combined organic layers were washed with sodium hydroxide solution (1 M, 2×50 mL), and brine (100 mL) separately. The resulting solution was dried over anhydrous sodium sulfate, filtered, and concentrated under reduced pressure to give a yellow oil (10 g, 98%) which was without further purification and characterization.

36

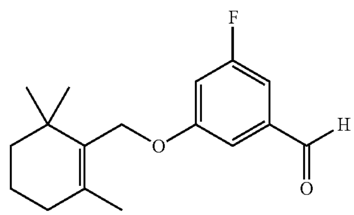

5-fluoro-3-((2,6,6-trimethylcyclohex-1-en-1-yl) methoxy)benzaldehyde (36)

Synthesis B was followed using 5-fluoro-3-hydroxybenzaldehyde (5 g, 35.6 mmol, 1.1 eq) resulting in isolation of a yellow oil (5.4 g, 70%). This molecule was used in the subsequent step without further characterization.

37

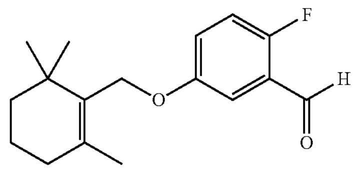

2-fluoro-5-((2,6,6-trimethylcyclohex-1-en-1-yl) methoxy)benzaldehyde (37)

Following synthesis B, 2-fluoro-5-hydroxybenzaldehyde (5.68 g, 40.5 mmol, 1 eq) gave a yellow oil (8.0 g, 71%). This molecule was used in the subsequent step without further characterization.

38

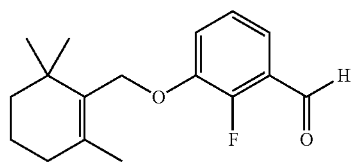

2-fluoro-3-((2,6,6-trimethylcyclohex-1-en-1-yl) methoxy)benzaldehyde (38)

Using 2-fluoro-3-hydroxybenzaldehyde (7.1 g, 50.7 mmol, 1.1 eq), synthesis B yielded a yellow oil (11 g, 85%). This molecule was used in the subsequent step without further characterization.

39

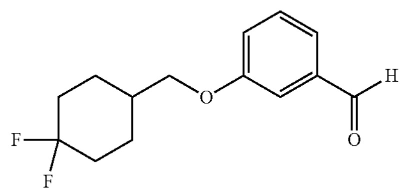

Synthesis C: Synthesis of 3-((4,4-difluorocyclohexyl)methoxy)benzaldehyde (39)

4,4'-difluorocyclohexylmethanol (1.0 g, 6.7 mmol), triethylamine (1.2 mL, 8.6 mmol) in dichloromethane (20 mL) was stirred for 30 min at 0° C. The mixture was then quenched with 2N HCl (30 mL) and extracted with dichloromethane (2×20 mL). The organic extracts were combined then washed with water (50 mL), brine (50 mL), and dried over sodium sulfate. Following filtration, organic solvents were removed under rotary evaporation to give a tan-white solid (1.53 g, 101%) which was used without purification. 1 g (4.3 mmol) of the synthesized mesylate was added to a suspension of 3-hydroxybenzaldehyde (450 mg, 3.7 mmol), potassium carbonate (1.1 g, 8.0 mmol) and DMF (20 mL) and allowed to stir overnight at 90° C. under argon. After allowing time to cool, the reaction mixture was quenched with 2N HCl (50 mL) and extracted with ethyl acetate (3×20 mL). The combined organic layers were washed with 2N NaOH (50 mL), water (50 mL), brine (50 mL), dried over anhydrous $Na_2SO_4$, filtered, and concentrated under reduced pressure. The crude oil was purified by flash column chromatography (silica gel, 20% ethyl acetate in hexanes, $R_f$=0.43 in 4:1 hexanes/ethyl acetate) to give a yellow syrup (630 mg, 67%). $^1$H NMR (500 MHz, $CDCl_3$) δ 9.98 (s, 1H), 7.49-7.42 (m, 2H), 7.37 (s, 1H), 7.17 (dt, J=6.4, 2.6 Hz, 1H), 3.88 (d, J=6.3 Hz, 2H), 2.23-2.11 (m, 2H), 2.01-1.87 (m, 3H), 1.78 (dtt, J=31.8, 13.6, 4.2 Hz, 2H), 1.51-1.39 (m, 2H). $^{13}$C NMR (126 MHz, $CDCl_3$) δ 218.31, 192.15, 159.51, 137.83, 130.11, 123.78, 121.97, 112.43, 72.04 (d, J=3.0 Hz), 35.84, 33.11 (dd, J=25.5, 22.8 Hz), 25.78 (d, J=9.9 Hz). $^{19}$F NMR (471 MHz, $CDCl_3$) δ-91.52 (d, J=235.8 Hz), -102.12 (d, J=236.6 Hz). HRMS (EI): (m/z) calculated for $C_{14}H_{16}F_2O_2$ $[M]^+$ 254.1118; found 254.1112.

Scheme 8 Synthetic Routes For α-Cyano Alcohol Synthesis

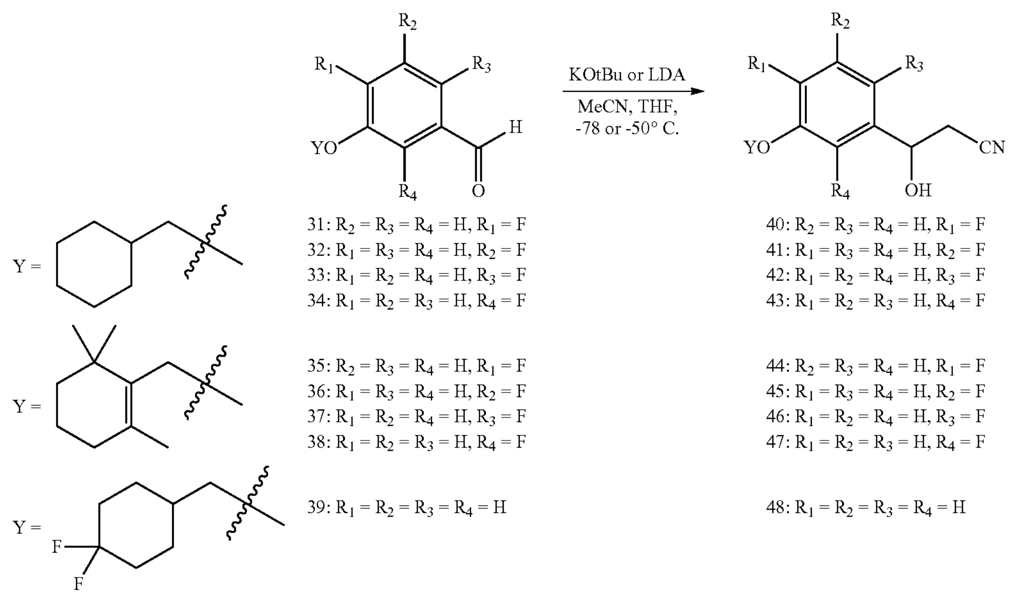

31: $R_2 = R_3 = R_4 = H, R_1 = F$
32: $R_1 = R_3 = R_4 = H, R_2 = F$
33: $R_1 = R_2 = R_4 = H, R_3 = F$
34: $R_1 = R_2 = R_3 = H, R_4 = F$
35: $R_2 = R_3 = R_4 = H, R_1 = F$
36: $R_1 = R_3 = R_4 = H, R_2 = F$
37: $R_1 = R_2 = R_4 = H, R_3 = F$
38: $R_1 = R_2 = R_3 = H, R_4 = F$
39: $R_1 = R_2 = R_3 = R_4 = H$

40: $R_2 = R_3 = R_4 = H, R_1 = F$
41: $R_1 = R_3 = R_4 = H, R_2 = F$
42: $R_1 = R_2 = R_4 = H, R_3 = F$
43: $R_1 = R_2 = R_3 = H, R_4 = F$
44: $R_2 = R_3 = R_4 = H, R_1 = F$
45: $R_1 = R_3 = R_4 = H, R_2 = F$
46: $R_1 = R_2 = R_4 = H, R_3 = F$
47: $R_1 = R_2 = R_3 = H, R_4 = F$
48: $R_1 = R_2 = R_3 = R_4 = H$

40

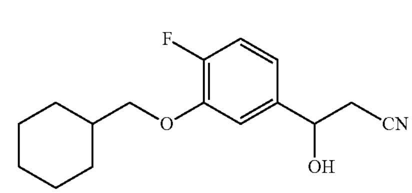

Route 1: Synthesis of 3-(3-(cyclohexylmethoxy)-4-fluorophenyl)-3-hydroxyacetonitrile (40)

To a solution of acetonitrile (3.82 g, 93.1 mmol, 2 eq) in THF (20 mL) was added potassium tert-butoxide (10.4 g, 93.1 mmol, 2 eq) in THF (30 mL) at −50° C. under nitrogen. The mixture was stirred at −50° C. for 2 h. Then compound 31 (11 g, 46.5 mmol, 1 eq) in THF (20 mL) was added at −50° C. The resulting mixture was stirred at −50° C. for another 1.5 h. The reaction was quenched with ammonium chloride solution (5%, 200 mL), and extracted with ethyl acetate (3×150 mL). The combined organic layers were washed with brine (300 mL), dried over anhydrous sodium sulfate, filtered and concentrated under reduced pressure. The residue was purified by silica gel column chromatography with petroleum ether/ethyl acetate (10:1) as eluent to give a yellow solid (8.3 g, 64%). This molecule was used in the subsequent step without further characterization. $^1H$ NMR ($CDCl_3$, 400 MHz) δ 7.00-7.10 (m, 2H), 6.87 (ddd, J=8.27, 4.19, 2.09 Hz, 1H), 4.99 (t, J=6.06 Hz, 1H), 3.83 (d, J=6.17 Hz, 2H), 2.74 (d, J=6.17 Hz, 2H), 1.67-1.93 (m, 6H), 1.27-1.37 (m, 2H), 1.14-1.23 (m, 1H), 1.00-1.12 (m, 2H).

41

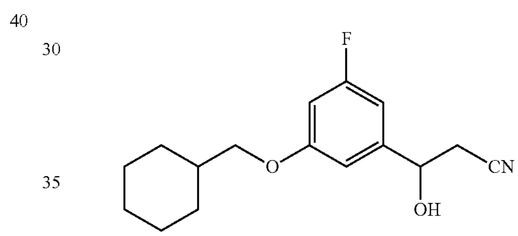

3-(3-(cyclohexylmethoxy)-5-fluorophenyl)-3-hydroxyacetonitrile (41)

Benzaldehyde 32 (4.5 g, 19 mmol, 1 eq) using Route 1, crude product was purified by silica gel column chromatography with petroleum ether/ethyl acetate (2:1) as eluent yielding a yellow oil (3 g, 57%). This molecule was used in the subsequent step without further characterization.

42

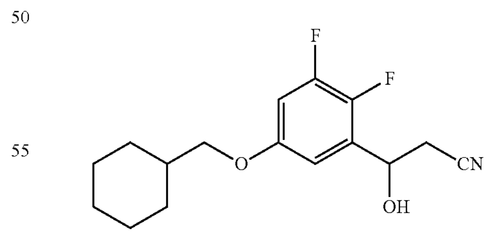

3-(5-(cyclohexylmethoxy)-2-fluorophenyl)-3-hydroxyacetonitrile (42)

Using compound 33 (10 g, 42.3 mmol, 1 eq) and following route 1, residue was purified by silica gel column chromatography with petroleum ether/ethyl acetate (10:1) yielded a yellow oil (6.8 g, 58%). This molecule was used in the subsequent step without further characterization. $^1H$ NMR ($CDCl_3$, 400 MHz) δ 7.07 (dd, J=3.2, 5.9 Hz, 1H), 7.00-6.94 (m, 1H), 6.81 (ddd, J=3.2, 4.1, 9.0 Hz, 1H), 5.32 (br s, 1H), 3.73 (d, J=6.4 Hz, 2H), 2.90-2.82 (m, 1H), 2.81-2.72 (m, 1H), 1.86 (br d, J=13.0 Hz, 2H), 1.81-1.69 (m, 4H), 1.37-1.14 (m, 3H), 1.12-0.99 (m, 2H).

43

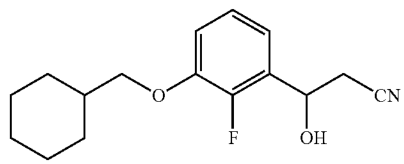

3-(3-(cyclohexylmethoxy)-2-fluorophenyl)-3-hydroxyacetonitrile (43)

Utilizing route 1 with compound 34 (6.2 g, 26.2 mmol, 1 eq), crude residue was purified by silica gel column chromatography with petroleum ether/ethyl acetate (1:1) as eluent to give compound 43 (6.1 g, 84%) as a yellow oil. This molecule was used in the subsequent step without further characterization. $^1H$ NMR ($CDCl_3$, 400 MHz) δ 7.06-7.15 (m, 2H), 6.89-6.99 (m, 1H), 5.35 (dd, J=7.06, 4.63 Hz, 1H), 3.81 (d, J=6.17 Hz, 2H), 2.72-2.92 (m, 2H), 1.66-1.94 (m, 6H), 1.00-1.40 (m, 6H).

44

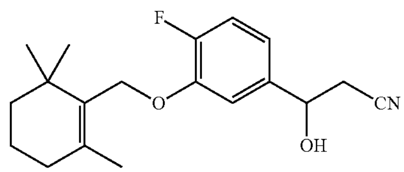

Route 2: 3-(4-fluoro-3-((2,6,6-trimethylcyclohex-1-en-1-yl)methoxy)phenyl)-3-hydroxypropane nitrile (44)

To a solution of acetonitrile (2.94 g, 71.7 mmol, 2.2 eq) in THF (50 mL) was added n-butyllithium (2.5 M, 31.2 mL, 2.4 eq) in THF (9 mL) at −78° C. under nitrogen. The mixture was stirred at −78° C. for 2 h. Then fluorinated benzaldehyde 35 (9 g, 32.6 mmol, 1 eq) in THF (20 mL) was added. The resulting mixture was stirred at −78° C. for another 1 h. The reaction was quenched by adding 5% ammonium chloride solution (100 mL). The mixture was extracted with ethyl acetate (3×50 mL). The combined organic layers were washed with brine (100 mL), dried over anhydrous sodium sulfate, filtered and concentrated under reduced pressure. The residue was purified by silica gel column chromatography with petroleum ether/ethyl acetate (10:1) as eluent to give nitrile 44 (6.5 g, 62.8% yield) as yellow oil. This molecule was used in the subsequent step without further characterization.

45

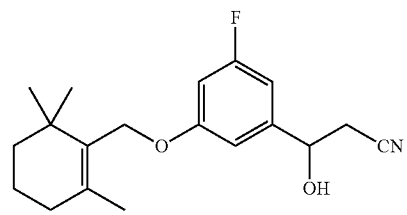

3-(3-fluoro-5-((2,6,6-trimethylcyclohex-1-en-1-yl)methoxy)phenyl)-3-hydroxypropanenitrile (45)

Following Route 2 using compound 36 (10 g, 36.2 mmol, 1 eq), crude material was purified by silica gel column chromatography with petroleum ether/ethyl acetate (10:1) to give a yellow oil (9.12 g, 79%). This molecule was used in the subsequent step without further characterization.

46

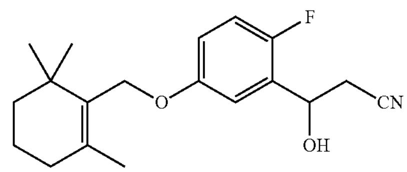

3-(2-fluoro-5-((2,6,6-trimethylcyclohex-1-en-1-yl)methoxy)phenyl)-3-hydroxypropanenitrile (46)

As outlined in Route 2, benzaldehyde 37 (8 g, 28.9 mmol, 1 eq) gave crude material which was purified by silica gel column chromatography using petroleum ether/ethyl acetate (10:1) as eluent to afford a yellow oil (3.5 g, 38%). This molecule was used in the subsequent step without further characterization.

47

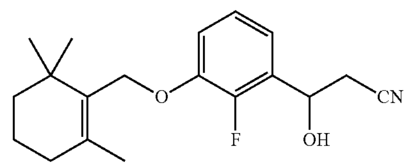

3-(2-fluoro-2-((2,6,6-trimethylcyclohex-1-en-1-yl)methoxy)phenyl)-3-hydroxypropanenitrile (47)

The sequence analogous to Route 2 was performed with aldehyde 38 (10 g, 36.2 mmol, 1 eq) resulting a residue that was purified by silica gel column chromatography with petroleum ether/ethyl acetate (1:1) to give a brown oil (7 g, 61%). This molecule was used in the subsequent step without further characterization. $^1H$ NMR ($CDCl_3$, 400 MHz) δ 7.15-7.12 (m, 2H), 7.08-7.02 (m, 1H), 5.39-5.32 (m, 1H), 4.53-4.46 (m, 2H), 2.91-2.84 (m, 1H), 2.82-2.74 (m, 2H), 2.08-2.05 (m, 2H), 1.74 (s, 3H), 1.69-1.62 (m, 2H), 1.53-1.48 (m, 2H), 1.06 (s, 6H).

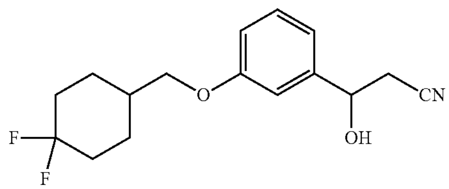

48

6.96 (s, 2H), 6.87 (dd, J=7.5, 1.6 Hz, 1H), 5.06-5.00 (m, 1H), 3.83 (d, J=6.3 Hz, 2H), 2.77 (d, J=6.3 Hz, 2H), 2.29 (d, J=3.5 Hz, 1H), 2.23-2.09 (m, 2H), 2.01-1.85 (m, 3H), 1.77 (ddd, J=33.0, 15.5, 11.6 Hz, 2H), 1.44 (d, J=37.0 Hz, 2H). $^{13}C$ NMR (126 MHz, $CDCl_3$) δ 159.56, 142.78, 130.27, 117.91, 117.27, 114.94, 111.69, 72.00 (d, J=2.7 Hz), 70.27, 36.05, 33.26 (dd, J=25.5, 22.9 Hz), 28.07, 25.96 (d, J=9.8 Hz). $^{19}F$ NMR (471 MHz, $CDCl_3$) δ-91.46 (d, J=235.8 Hz), -102.11 (d, J=236.6 Hz). HRMS (EI): (m/z) calculated for $C_{16}H_{19}F_2NO_2$ $[M]^+$295.1384; found 295.1374.

Scheme 9 General Procedure for Nitrile Reduction

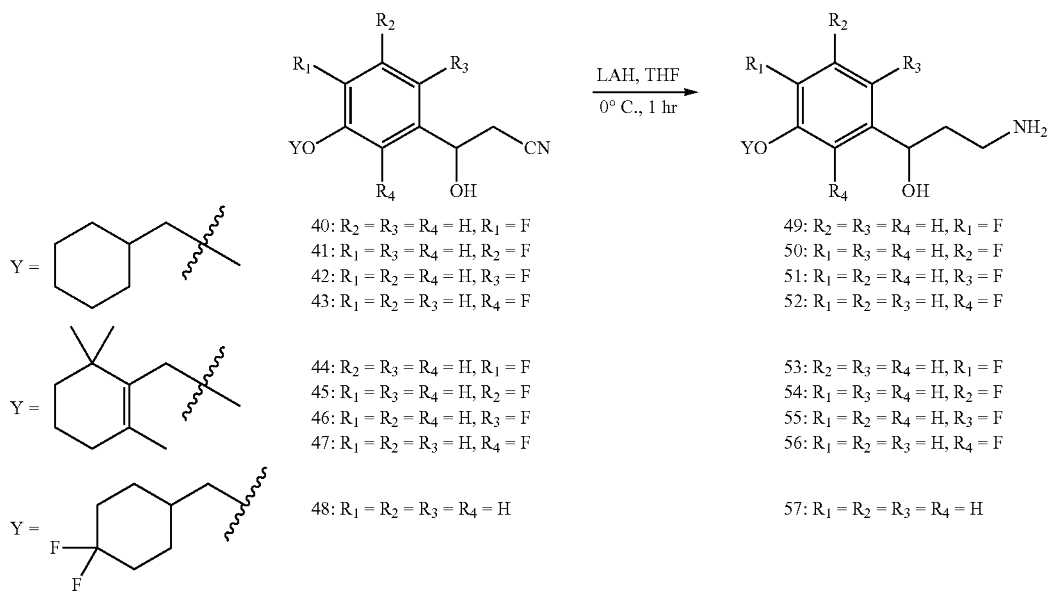

Synthesis of 3-(3-((4,4-difluorocyclohexyl) methoxy)phenyl)-3-hydroxypropanenitrile (48)

LDA was generated in situ by the addition of nBuLi (2.5 M in hexanes, 1.8 mL, 4.5 mmol) dropwise to a stirred solution of diisopropylamine (0.6 mL, 4.3 mmol) in THF (15 mL). After stirring for 0.5 hr at −78° C. for 0.5 hr, acetonitrile (250 u L, 4.8 mmol) was added and the reaction mixture stirred for an additional 0.5 hr. The solution of compound 39 (600 mg, 5.0 mmol) in THF (5 mL) was added to the round bottom flask in a dropwise manner then the resulting reaction mixture then was allowed to stir at −78° C. for 3 hr. The reaction mixture was allowed to warm to rt, quenched with sat. ammonium chloride (50 mL), and extracted with ethyl acetate (3×30 mL). The combined organic extracts were then washed with water (100 mL), brine (100 mL), dried over magnesium sulfate, filtered, and concentrated in vacuo. The crude oil was purified by flash column chromatography (silica, 20-50% ethyl acetate in hexanes, $R_f$=0.16 in 4:1 hexanes/ethyl acetate) to afford a colorless syrup (505 mg, 72%). $^1H$ NMR (500 MHz, $CDCl_3$) δ 7.30 (t, J=8.2 Hz, 1H),

49

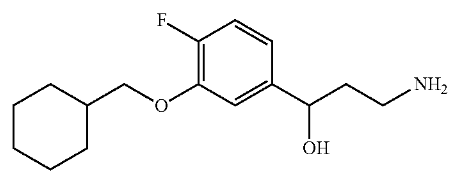

General Procedure: Synthesis of 3-amino-1-(3-(cyclohexylmethoxy)-4-fluorophenyl)propan-1-ol (49, 4-fluoro-emixustat)

To a solution of compound 40 (8 g, 28.8 mmol, 1 eq) in dry THF (55 mL) was added lithium aluminum hydride (2.46 g, 64.9 mmol, 2.25 eq) in portions under nitrogen at 0° C., and then the reaction mixture was stirred at 0° C. for another 0.5 h. The reaction was quenched with adding water (2.46 mL), sodium hydroxide solution (10%, 2.46 mL) and water (7.38 mL) sequentially. The resulting mixture was filtered and concentrated under vacuum. The residue was purified by silica gel chromatography with dichloromethane/methanol (10/1) as eluent to give the γ-49 (1.5 g, 18%) as a yellow gum. $^1H$ NMR (600 MHz, $CDCl_3$): δ 7.08-6.88 (m, 2H), 6.85-6.72 (m, 1H), 4.82 (d, J=6.97 Hz, 1H), 4.50 (bs, 3H), 3.77 (d, J=6.43 Hz, 2H), 3.18-3.00 (m, 1H), 3.00-2.83

(m, 1H), 1.94-1.82 (m, 3H), 1.82-1.76 (m, 2H), 1.76-1.70 (m, 2H), 1.70-1.65 (m, 1H), 1.33-1.22 (m, 2H), 1.22-1.13 (m, 1H), 1.07-0.94 (ddd, J=2.4, 12.21, 24.11 Hz, 2H). $^{13}C$ NMR (150 MHz, $CDCl_3$) δ 151.86 (d, J=244.81 Hz), 147.38 (d, J=10.69 Hz), 141.10 (d, J=3.16 Hz), 117.62 (d, J=6.83 Hz), 115.76 (d, J=18.41 Hz), 112.33 (d, J=1.09 Hz), 74.91, 74.02, 39.69, 38.62, 37.83, 29.90, 26.59, 25.87. $^{19}F$ (565 MHz, $CDCl_3$): δ-136.8-(−)136.95 (m). HRMS (ESI): calculated for $C_{16}H_{24}FNO_2$ $[M+H]^+$, 282.1869; found, 282.1862.

50

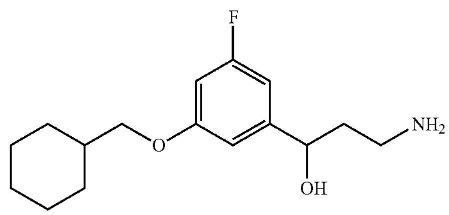

3-amino-1-(3-(cyclohexylmethoxy)-5-fluorophenyl) propan-1-ol (50, 5-fluoro-emixustat)

General procedure followed with nitrile 41 (5 g, 35.6 mmol, 1.1 eq) yielding a yellow gum (1.60 g, 51%). $^1H$ NMR (600 MHz, $CDCl_3$): δ 6.73-6.68 (m, 1H), 6.65 (d, J=9.31 Hz, 1H), 6.46 (dt, J=2.24, 10.72 Hz, 1H), 4.87 (dd, J=2.66, 8.48 Hz, 1H), 3.71 (d, J=6.41 Hz, 2H), 3.29 (bs, 3H), 3.1-3.03 (m, 1H), 3-2.89 (m, 1H), 1.88-1.80 (m, 3H), 1.79-1.73 (m, 3H), 1.73-1.64 (m, 2H), 1.32-1.24 (m, 2H), 1.23-1.15 (m, 1H), 1.03 (ddd, J=3.23, 12.36, 24.36 Hz, 2H). $^{13}C$ NMR (150 MHz, $CDCl_3$) δ 163.69 (d, J=244.31 Hz), 160.67 (d, J=11.26 Hz), 148.47 (d, J=8.61 Hz), 117.60 (d, J=1.96 Hz), 104.63 (d, J=22.29 Hz), 100.60 (d, J=25.04 Hz), 74.86, 73.85, 40.30, 39.24, 37.75, 29.96, 26.60, 25.89. $^{19}F$ (565 MHz, $CDCl_3$): δ-112.20 (t, J=10.11 Hz). HRMS (ESI): calculated for $C_{16}H_{24}FNO_2$ $[M+H]^+$, 282.1869; found, 282.1874.

51

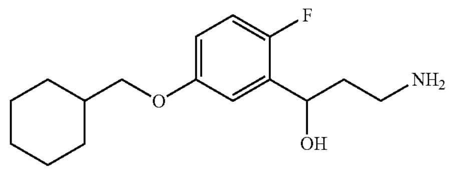

3-amino-1-(5-(cyclohexylmethoxy)-2-fluorophenyl) propan-1-ol (51, 6-fluoro-emixustat)

General procedure followed with compound 42 (3.5 g, 12.6 mmol, 1 eq) giving a yellow gum (800 mg, 22.7%) $^1H$ NMR (600 MHz, $CDCl_3$): δ 7.11 (dd, J=3.18, 6 Hz, 1H), 6.87 (dd, J=9.04, 9.71 Hz, 1H), 6.69 (dt, J=3.67, 9.04 Hz, 1H), 5.20 (dd, J=3.01, 8.41 Hz, 1H), 3.75-3.69 (m, 2H), 3.47-2.98 (m, 4H), 2.98-2.94 (m, 1H), 1.94-1.88 (m, 1H), 1.87-1.82 (m, 2H), 1.8-1.72 (m, 4H), 1.70-1.66 (m, 1H), 1.32-1.24 (m, 2H), 1.23-1.15 (m, 1H), 1.03 (ddd, J=3.33, 12.32, 24.29 Hz, 2H). $^{13}C$ NMR (150 MHz, $CDCl_3$) δ 155.73 (d, J=1.75 Hz), 153.68 (d, J=237.45 Hz), 132.85 (d, J=14.90 Hz), 115.50 (d, J=23.55 Hz), 113.95 (d, J=8.01 Hz), 112.74 (d, J=4.50 Hz), 74.20, 69.52 (d, J=1.69 Hz), 40.53, 38.18, 37.91, 30.03, 30.00, 26.64, 25.92. $^{19}F$ (565 MHz, $CDCl_3$): δ-130.78-(−)130.88 (m). HRMS (ESI): calculated for $C_{16}H_{24}FNO_2$ $[M+H]^+$, 282.1869; found, 282.1864.

52

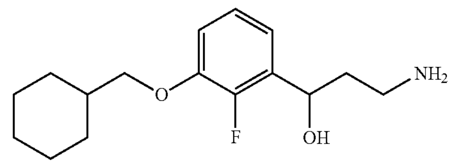

3-amino-1-(3-(cyclohexylmethoxy)-2-fluorophenyl) propan-1-ol (52, 2-fluoro-emixustat)

The general procedure was followed using nitrile 43 (3 g, 10.8 mmol, 1 eq) resulting in isolation of a yellow gum (2.1 g, 66%). $^1H$ NMR (600 MHz, $CDCl_3$): δ 7.1 (t, J=6.72 Hz, 1H), 7 (t, J=8.06 Hz, 1H), 6.82 (t, J=8.06 Hz, 1H), 5.25 (d, J=8.36 Hz, 1H), 4.25 (bs, 3H), 3.77 (d, J=6.39 Hz, 2H), 3.15-3.06 (m, 1H), 3.06-2.96 (m, 1H), 2-1.95 (m, 1H), 1.89-1.84 (m, 3H), 1.83-1.79 (m, 1H), 1.76-1.72 (m, 2H), 1.7-1.66 (m, 1H), 1.32-1.24 (m, 2H), 1.22-1.14 (m, 1H), 1.07-1 (ddd, J=3.32, 12.42, 24.26 Hz, 2H). $^{13}C$ NMR (150 MHz, $CDCl_3$) δ 149.42 (d, J=244.70 Hz), 147.12 (d, J=10.74 Hz), 132.69 (d, J=10.77 Hz), 123.89 (d, J=4.38 Hz), 118.49 (d, J=3.29 Hz), 113.41, 74.95, 68.72, 39.86, 37.78, 37.11, 29.1, 26.61, 25.87. $^{19}F$ (565 MHz, $CDCl_3$): δ-141.76-(−)141.84 (m). HRMS (ESI): calculated for $C_{16}H_{24}FNO_2$ $[M+H]^+$, 282.1869; found, 282.1869.

53

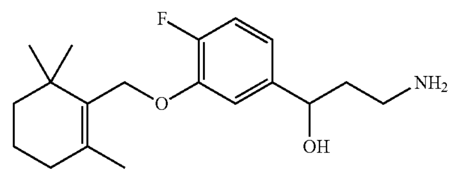

3-amino-1-(4-fluoro-3-((2,6,6-trimethylcyclohex-1-en-1-yl)methoxy)phenyl)propan-1-ol (53, 4-Fluoro-MB001)

Steps were carried out according to the general procedure using compound 44 (6 g, 18.9 mmol, 1 eq) to give title compound 53 (1.40 g, 22%) as a yellow gum. $^1H$ NMR (600 MHz, $CDCl_3$): δ 7.12 (dd, J=1.54, 8.09 Hz, 1H), 6.99 (dd, J=8.35, 11.05 Hz, 1H), 6.87-6.81 (m, 1H), 4.90 (dd, J=2.28, 8.83 Hz, 1H), 4.5 (s, 2H), 3.62 (bs, 3H), 3.15-3.06 (m, 1H), 3.01-2.91 (m, 1H), 2.03 (t, J=6.24 Hz, 2H), 1.89-1.82 (m, 1H), 1.78-1.74 (m, 1H), 1.72 (s, 3H), 1.66-1.61 (m, 2H), 1.53-1.45 (m, 2H), 1.05 (s, 6H). $^{13}C$ NMR (150 MHz, $CDCl_3$) δ 152.18 (d, J=244.65 Hz), 147.33 (d, J=11.10 Hz), 141.41 (d, J=3.36 Hz), 136.22, 132.98, 118.07 (d, J=6.77 Hz), 115.76 (d, J=18.67 Hz), 113.26 (d, J=1.93 Hz), 74.94, 66.40, 40.46, 39.44, 39.37, 34.13, 33.02, 28.52, 19.94, 19.38. $^{19}F$ (565 MHz, $CDCl_3$): δ-135.72-(−)135.82 (m). HRMS (ESI): calculated for $C_{19}H_{28}FNO_2$ $[M+H]^+$, 322.2182; found, 322.2176.

54

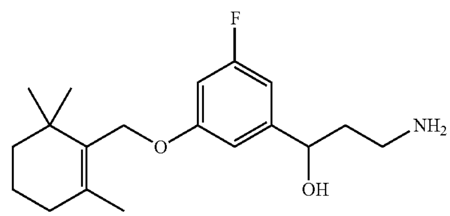

3-amino-1-(3-fluoro-5-((2,6,6-trimethylcyclohex-1-en-1-yl)methoxy)phenyl)propan-1-ol (54, 5-fluoro-MB001)

Utilizing the general procedure with compound 45 (6 g, 18.9 mmol, 1 eq) led to successful isolation of a yellow gum (1.50 g, 18%). $^{1}$H NMR (600 MHz, $CDCl_3$): δ 6.82-6.72 (m, 1H), 6.70-6.62 (m, 1H), 6.57-6.50 (m, 1H), 4.88 (dd, J=2.57, 8.47 Hz, 1H), 4.59 (bs, 3H), 4.39 (s, 2H), 3.18-3.06 (m, 1H), 3.06-2.84 (m, 1H), 2.07-2 (m, 2H), 1.97-1.86 (m, 1H), 1.83-1.75 (m, 1H), 1.67 (s, 3H), 1.66-1.56 (m, 2H), 1.53-1.42 (m, 2H), 1.02 (s, 6H). $^{13}$C NMR (150 MHz, $CDCl_3$) δ 163.69 (d, J=242.91 Hz), 160.77 (d, J=10.65 Hz), 148.08 (d, J=8.42 Hz), 136.11, 132.89, 107.80 (d, J=1.49 Hz), 104.71 (d, J=22.70 Hz), 100.96 (d, J=24.80 Hz), 74.10, 64.93, 39.65, 39.35, 38.22, 34.18, 32.97, 28.50, 19.90, 19.36. $^{19}$F (565 MHz, $CDCl_3$): δ-111.89 (t, J=9.97 Hz). HRMS (ESI): calculated for $C_{19}H_{28}FNO_2$ $[M+H]^+$, 322.2182; found, 322.2173.

55

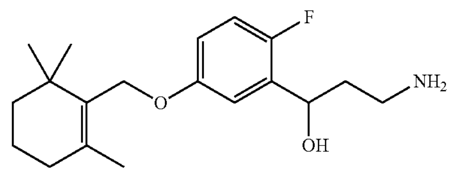

3-amino-1-(2-fluoro-5-((2,6,6-trimethylcyclohex-1-en-1-yl)methoxy)phenyl)propan-1-ol (55, 6-Fluoro-MB001)

The general procedure was carried out with 46 (3.0 g, 9.45 mmol, 1 eq) giving amine 55 (1.1 g, 34%) as a yellow gum. $^{1}$H NMR (600 MHz, $CDCl_3$): δ 7.18 (dd, J=3.09, 5.88 Hz, 1H), 6.88 (t, J=9.46 Hz, 1H), 6.79-6.75 (m, 1H), 5.22 (dd, J=2.04, 8.37 Hz, 1H), 4.42 (d, J=9.79 Hz, 1H), 4.38 (d, J=9.79 Hz, 1H), 4.14 (bs, 3H), 3.16-3.06 (m, 1H), 3.06-2.95 (m, 1H), 2.03 (t, J=5.90 Hz, 2H), 1.99-1.93 (m, 1H), 1.82-1.76 (m, 1H), 1.69 (s, 3H), 1.66-1.61 (m, 2H), 1.53-1.45 (m, 2H), 1.03 (s, 6H). $^{13}$C NMR (150 MHz, $CDCl_3$) δ 155.81 (d, J=1.48 Hz), 153.77 (d, J=237.48 Hz), 135.78, 133.28, 132.61 (d, J=14.85 Hz), 115.57 (d, J=23.74 Hz), 114.48 (d, J=7.96 Hz), 112.86 (d, J=4.42 Hz), 69.15, 65.28, 40.13, 39.39, 37.47, 34.21, 32.97, 28.55, 28.53, 19.93, 19.4. $^{19}$F (565 MHz, $CDCl_3$): δ-130.41-(−)130.48 (m). HRMS (ESI): calculated for $C_{19}H_{28}FNO_2$ $[M+H]^+$, 322.2182; found, 322.2179.

56

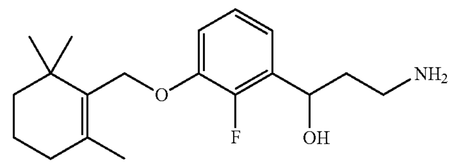

3-amino-1-(2-fluoro-3-((2,6,6-trimethylcyclohex-1-en-1-yl)methoxy)phenyl)propan-1-ol (56, 2-fluoro-MB001)

The actions of the general procedure were carried out with nitrile 47 (6.5 g, 20.5 mmol, 1 eq) to give a brown gum (1.06 g, 16%). $^{1}$H NMR (600 MHz, $CDCl_3$): δ 7.14 (t, J=6.82 Hz, 1H), 7.04 (t, J=8.07 Hz, 1H), 6.94 (t, J=8.07 Hz, 1H), 5.24 (d, J=7.23 Hz, 1H), 4.48 (d, J=9.85 Hz, 1H), 4.45 (d, J=9.85 Hz, 1H), 4.24 (bs, 3H), 3.12-3.03 (m, 1H), 3.03-2.92 (m, 1H), 2.03 (t, J=6.08 Hz, 2H), 1.99-1.92 (m, 1H), 1.86-1.78 (m, 1H), 1.72 (s, 3H), 1.66-1.60 (m, 2H), 1.52-1.46 (m, 2H), 1.05 (s, 6H). $^{13}$C NMR (150 MHz, $CDCl_3$) δ 149.89 (d, J=244.39 Hz), 147.12 (d, J=11.27 Hz), 136.16, 133.00, 132.94 (d, J=11.11 Hz), 123.89 (d, J=4.21 Hz), 118.91 (d, J=3.27 Hz), 114.54, 68.77, 66.56, 39.9, 39.39, 37.41, 34.12, 33.02, 28.53, 19.93, 19.37. $^{19}$F (565 MHz, $CDCl_3$): δ-140.35-(−)140.46 (m). HRMS (ESI): calculated for $C_{19}H_{28}FNO_2$ $[M+H]^+$, 322.2182; found, 322.2173.

57

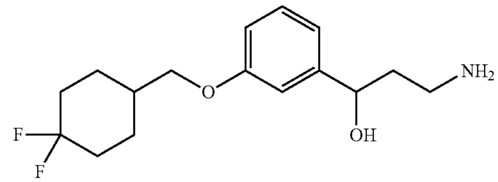

3-amino-1-(3-((4,4-difluorocyclohexyl)methoxy)phenyl) propan-1-ol (57)

Using compound 47 (3.0 g, 10.1 mmol, 1 eq) and following the general procedure gave amine 57 (580 mg, 17% yield) as a yellow gum. $^{1}$H NMR (600 MHz, $CDCl_3$): δ 7.19 (t, J=7.91 Hz, 1H), 6.92-6.89 (m, 1H), 6.89-6.86 (m, 1H), 6.74 (dd, J=2.01, 8.24 Hz, 1H), 5.80 (bs, 4H), 4.84 (dd, J=2.61, 9.01 Hz, 1H), 3.76 (d, J=6.39 Hz, 2H), 3.12-3.04 (m, 1H), 3.01-2.94 (m, 1H), 2.15-2.07 (m, 2H), 1.97-1.86 (m, 4H), 1.84-1.81 (m, 1H), 1.81-1.64 (m, 2H), 1.43-1.35 (m, 2H). $^{13}$C NMR (150 MHz, $CDCl_3$) δ 159.23, 146.34, 129.54, 123.64 (t, J=240.03 Hz), 118.05, 113.21, 111.88, 73.24, 71.83, 38.81, 37.49, 36.02, 33.27 (dd, J=23.27, 24.79 Hz), 25.95, 25.89. $^{19}$F (565 MHz, $CDCl_3$): δ-91.39 (d, J=235.82 Hz), -101.99 (d, J=235.82 Hz). HRMS (ESI): calculated for $C_{16}H_{23}F_2NO_2$ $[M+H]^+$, 300.1775; found, 300.1761.

Scheme 10 Deuteration of α-Cyano Alcohols

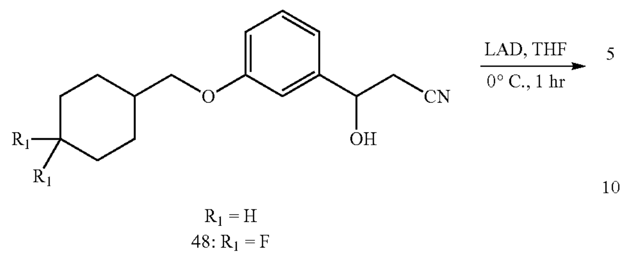

$R_1 = H$
48: $R_1 = F$

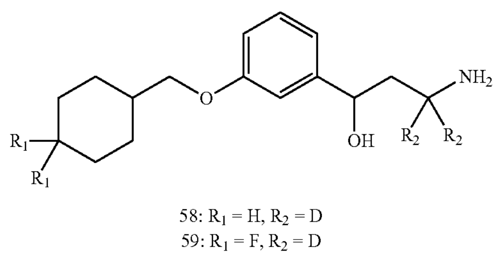

58: $R_1 = H$, $R_2 = D$
59: $R_1 = F$, $R_2 = D$

58

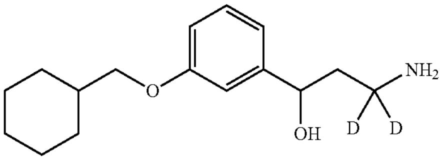

Synthesis of 3-amino-1-(3-(cyclohexylmethoxy) phenyl)propan-3,3-$d_2$-1-ol (58)

3-(3-(cyclohexylmethoxy) phenyl)-3-hydroxypropanenitrile (200 mg, 0.77 mmol) in THF (2 mL) was added dropwise to an ice-cold suspension of lithium aluminium deuteride (100 mg, 2.38 mmol) in THF (3 mL). The mixture stirred for 1 hr at 0° C., then was carefully quenched on ice with consecutive additions of water (200 μL), 15% NaOH (200 μL), and water (600 μL). After 30 min of stirring at rt, the reaction mixture was filtered through cotton, diluted in water (30 mL), and extracted with dichloromethane (3×10 mL). The organic layers were combined and dried over sodium sulfate. Following concentration in-vacuo, the crude product was purified by flash column chromatography (silica, 70:30:0-90:10:4-70:30:4 DCM/MeOH/$NH_4OH$, $R_f$=0.56 in 70:30:4 DCM/MeOH/$NH_4OH$) giving a yellow oil (69 mg, 34%). $^1H$ NMR (500 MHz, $CDCl_3$) δ 7.23 (t, J=7.9 Hz, 1H), 6.96 (s, 1H), 6.91 (d, J=7.6 Hz, 1H), 6.77 (dd, J=8.4, 2.6 Hz, 1H), 4.94 (dd, J=8.6, 3.2 Hz, 1H), 3.76 (d, J=6.4 Hz, 2H), 2.45 (s, 3H), 1.91-1.82 (m, 3H), 1.79-1.65 (m, 5H), 1.35-1.14 (m, 3H), 1.05 (qd, J=12.2, 3.4 Hz, 2H). $^{13}C$ NMR (126 MHz, $CDCl_3$) δ 159.62, 146.93, 129.33, 117.85, 113.28, 111.83, 75.62, 73.58, 39.52, 37.92, 30.10, 26.69, 25.97. HRMS (ESI+): (m/z) calculated for $C_{16}H_{24}D_2NO_2$ $[M+H]^+$ 266.2084; found 266.2083.

59

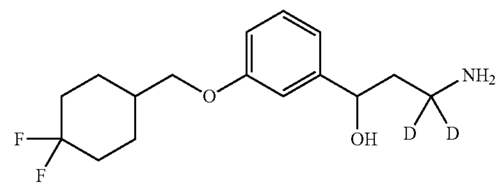

Synthesis of 3-amino-1-(3-((4,4-difluorocyclohexyl) methoxy)phenyl)propan-3,3-$d_2$-1-ol (59)

Nitrile 48 (200 mg, 0.77 mmol) in THF (2 mL) was added dropwise to an ice-cold suspension of lithium aluminium deuteride (100 mg, 2.38 mmol) in THF (3 mL). The mixture stirred for 1 hr at 0° C., then was carefully quenched on ice with consecutive additions of water (200 μL), 15% NaOH (200 μL), and water (600 μL). After 30 min of stirring at rt, the reaction mixture was filtered through celite, diluted in water (30 mL), and extracted with dichloromethane (3×10 mL). The organic layers were combined and dried over sodium sulfate. Following concentration in-vacuo, the crude product was purified by flash column chromatography (silica, 90:10:0-70:30:0-90:10:4-70:30:4 DCM/MeOH/$NH_4OH$, $R_f$=0.23 in 90:10:4 DCM/MeOH/$NH_4OH$) giving a colorless syrup (140 mg, 45%). $^1H$ NMR (500 MHz, $CDCl_3$) δ 7.23 (d, J=7.8 Hz, 1H), 6.97 (s, 1H), 6.93 (d, J=7.6 Hz, 1H), 6.77 (dd, J=8.1, 2.5 Hz, 1H), 4.95 (dd, J=8.7, 3.0 Hz, 1H), 3.83 (dd, J=6.5, 2.1 Hz, 2H), 2.18-2.10 (m, 3H), 2.00-1.93 (m, 4H), 1.92-1.84 (m, 4H), 1.81-1.66 (m, 5H), 1.47-1.38 (m, 2H). $^{13}C$ NMR (126 MHz, $CDCl_3$) δ 159.22, 147.14, 129.40, 118.23, 113.21, 111.71, 75.69, 71.85 (d, J=2.8 Hz), 39.52, 36.12, 33.29 (dd, J=25.5, 22.8 Hz), 25.99 (d, J=9.7 Hz). $^{19}F$ NMR (471 MHz, $CDCl_3$) δ-91.40 (d, J=236.4 Hz), -102.00 (d, J=236.2 Hz). HRMS (ES): (m/z) calculated for $C_{16}H_{21}D_2F_2NO_2$ $[M]^+$301.1820; found 301.1822.

Scheme 11 Synthesis of ACU-5201

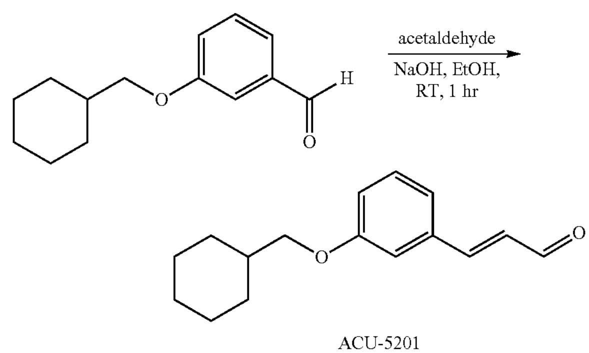

ACU-5201

Acetaldehyde (0.2 mL, 3.6 mmol) was added dropwise to an ice-cold solution of 3-(cyclohexylmethoxy)benzaldehyde (260 mg, 1.2 mmol) in 15% NaOH/EtOH (5:4 v/v, 9 mL). After 30 min the contents were poured over ice and extracted with DCM (3×20 mL). The combined organic layers were dried over sodium sulfate, filtered, and concentrated under reduced pressure. Crude material was then purified by flash column chromatography (silica, 0-10% EtOAc in hexanes, $R_f$=0.38 in 9:1 hexanes/EtOAc) to afford a yellow solid (42 mg, 14%). $^1$H NMR (500 MHz, $CDCl_3$) δ 9.70 (d, J=7.7 Hz, 1H), 7.44 (d, J=16.0 Hz, 1H), 7.33 (t, J=7.9 Hz, 1H), 7.17-7.11 (m, 1H), 7.07 (s, 1H), 7.01-6.95 (m, 1H), 6.70 (dd, J=15.9, 7.7 Hz, 1H), 3.78 (d, J=6.4 Hz, 2H), 1.91-1.85 (m, 2H), 1.81-1.67 (m, 4H), 1.36-1.16 (m, 5H), 1.12-1.01 (m, 2H). $^{13}$C NMR (126 MHz, $CDCl_3$) δ 193.89, 159.93, 153.02, 135.43, 130.21, 128.92, 121.15, 117.85, 113.99, 73.81, 37.81, 30.02, 26.62, 25.92. HRMS (EI): (m/z) calculated for $C_{16}H_{20}O_2[M]^+$244.1463; found 244.1465.

Results

Synthesis

Here, we report three families of molecules where we employed a common strategy, constructing a variety of alkoxy substituents of a central aryl core initially, and then adding a γ-hydroxyalkylamine moiety. We considered two general approaches that are differentiated primarily by the directionality of molecule construction with respect to the aryl core. The strategic difference between the approaches was in the order of construction of the alkoxy-substituents with respect to the γ-hydroxyalkylamine functionality. These strategies allowed for the incorporation of fluorine into both the alkoxy- and aryl-substituents and made possible the incorporation of deuterium in the final step of the isotopic synthesis. The alkyl substituents were installed onto either hydroxyacetophenone or hydroxybenzaldehyde backbone (Schemes 1 and 7). The resulted alkylated carbonyl compounds were converted to α-cyano alcohols (cyanohydrines) and subsequently to γ-hydroxyalkylamines (Schemes 8-10). Using the alkoxy-substituted acetophenone derivatives, we developed a novel methodology to install the chiral γ-aminoalcohol fragments using a three-component Mannich reaction with chiral amine accompanied by a chiral resolution step to obtain optically pure emixustat derivatives critical for RPE65 recognition (Schemes 2-6). The Mannich reaction was performed using the optimized conditions with all acetophenones, 1-4, (S)-(−)-α-methylbenzylamine, and paraformaldehyde (or 1,3,5-trioxane) in 1,4-dioxane, and the resulting molecules were reduced with sodium borohydride to produce a mixture of diastereomeric γ-aminoalcohols (Schemes 2-3). Conversion of diastereomeric aminoalcohols to cyclic carbamates with 1,1'-carbonyldiimidazole allowed for facile chromatographic separation of diastereomers. The single diastereomers of cyclic carbamates were hydrolyzed followed by debenzylation through Pd/C-catalyzed transfer hydrogenolysis; and the desired γ-hydroxyalkylamine products could be obtained as pure enantiomers (Schemes 4-6). In this study, most emixustat derivatives were synthesized as mixtures of their (S) and (R) enantiomers. Only the most biologically active molecules were examined for specific light rotation ($[u]_D$) and compared to (R)-emixustat. It was assumed that the R enantiomer of the fluorinated compounds would exhibit a positive rotation angle similar to (R)-emixustat.

Inhibitory Properties and Pharmacokinetics of the Tested Compounds

A total of nineteen novel emixustat derivatives were synthesized, and their inhibitory effects on RPE65 in vitro were characterized by the decrease of 11-cis-retinol production by bovine RPE microsomes (FIGS. 2, A and B). All of the synthesized primary amines showed intense inhibition of RPE65 activity at submicromolar concentrations. Compared to emixustat and MB-001, a single fluorination at C2' of the phenyl ring significantly increases the inhibitory potency. Pronounced enhancement is seen with compound 24 ($IC_{50}$=50±9 nM) and is the most potent RPE65 inhibitor that we have identified to date, with an inhibitory potency 3 times greater than the racemic emixustat ($IC_{50}$=172±29 nM), and twice that of (R)-MB-004 ($IC_{50}$=106±16 nM) which is the parent molecule of compound 24 lacking the 2'-fluorine substitution. The gem-difluorination of the cyclohexyl ring in 57 also enhanced the inhibition of 11-cis-retinol production. The inhibition curve of 57 was found to exhibit a double sigmoidal feature indicative of two distinct modes of inhibitor binding to RPE65.

Figure 3A:
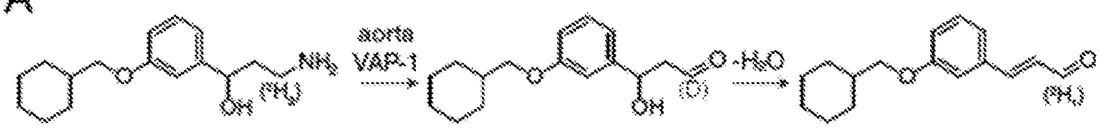
FIGS. 3(A-D) illustrate impact of emixustat deuteration on VAP-1 metabolic susceptibility. A) Scheme showing the oxidation of emixustat or 58 ($^2$H-emixustat) by VAP-1 present in the aorta homogenates used for the assay. The middle product is presumably formed but not detected owing to rapid dehydration to form ACU-5201. B) HPLC chromatographs showing the formation of ACU-5201 over time, after incubation of emixustat or 58 with mouse aorta homogenates containing VAP-1. The HPLC traces are split at 10 min with two different scales used to aid in visualization. Emixustat and 58 elute at ~8.5 min (left, arrow) while ACU-5201 elutes at ~13.3 min (right, arrow). The identities of the product peaks were verified by comparison of their retention times and UV/V is absorbance spectra (C) to that of authentic ACU-5201 standard. D) Quantification of product formation showed that the deuteration at the 3-position reduced product formation nearly three-fold at both 1 h and 2 h time points. Mean values ±SDs and individual data points are shown in the graph.
Figure 3B:
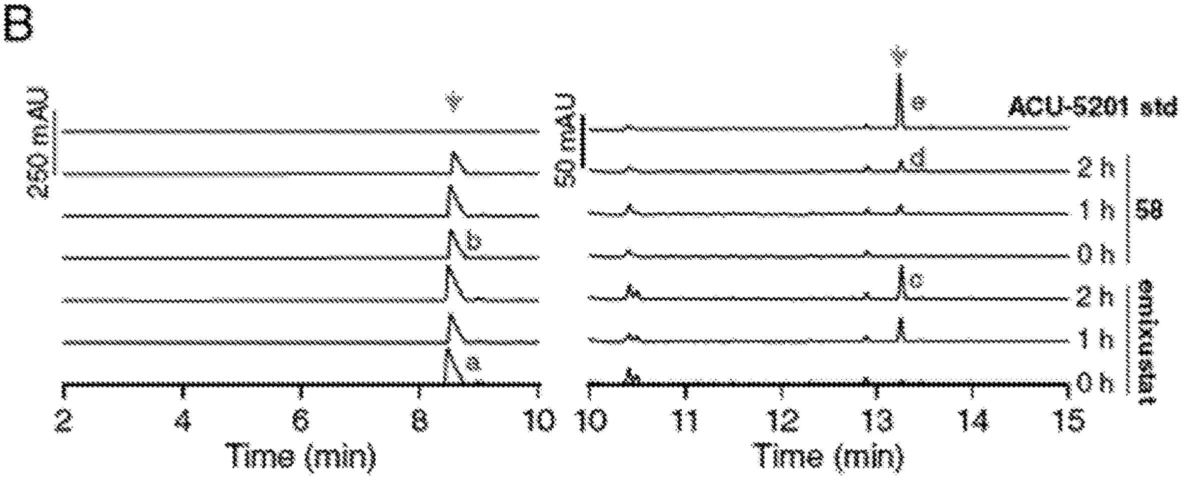
Figure 3C:
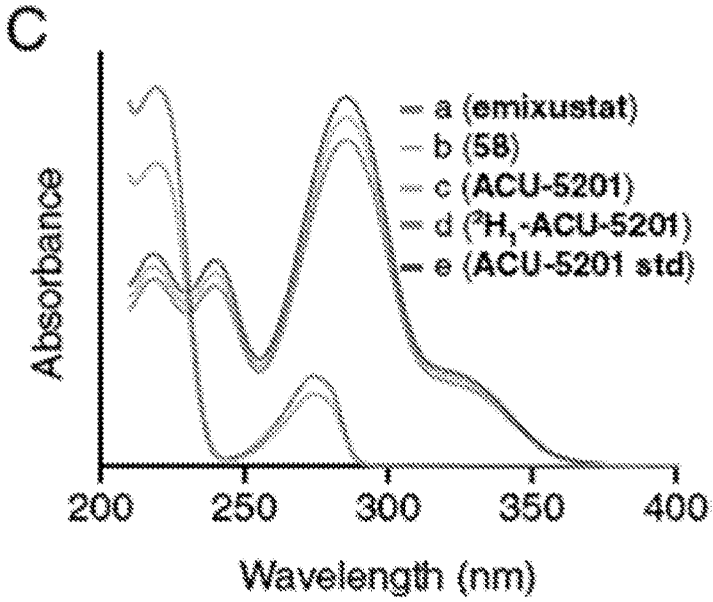
Figure 3D:
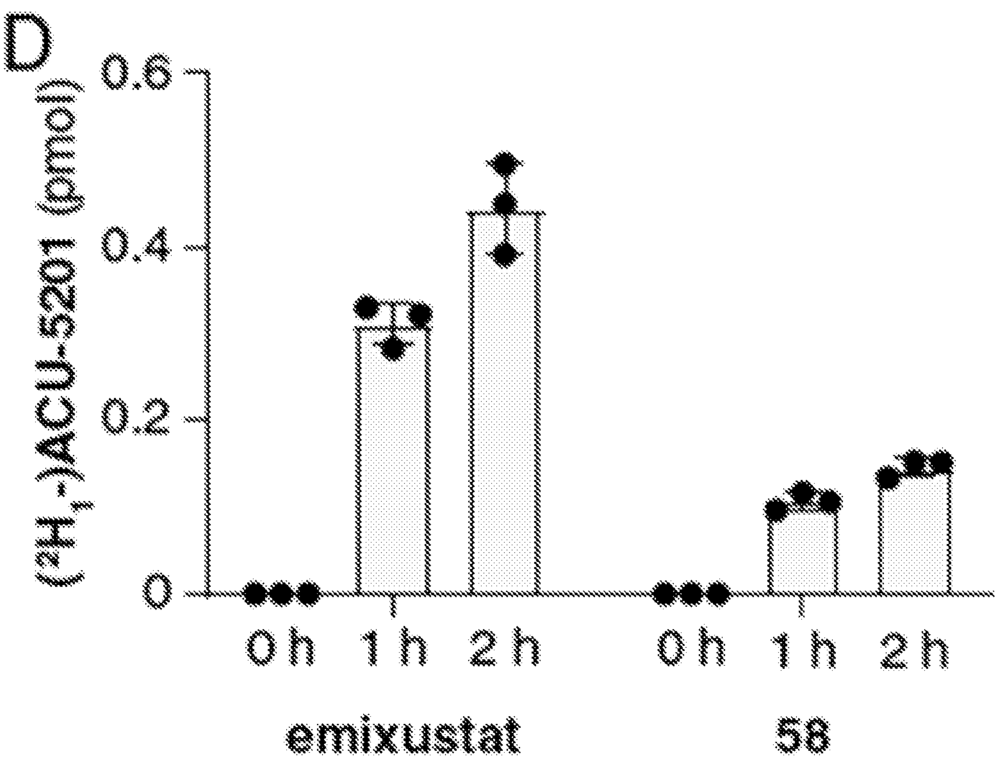
Figure 4A:
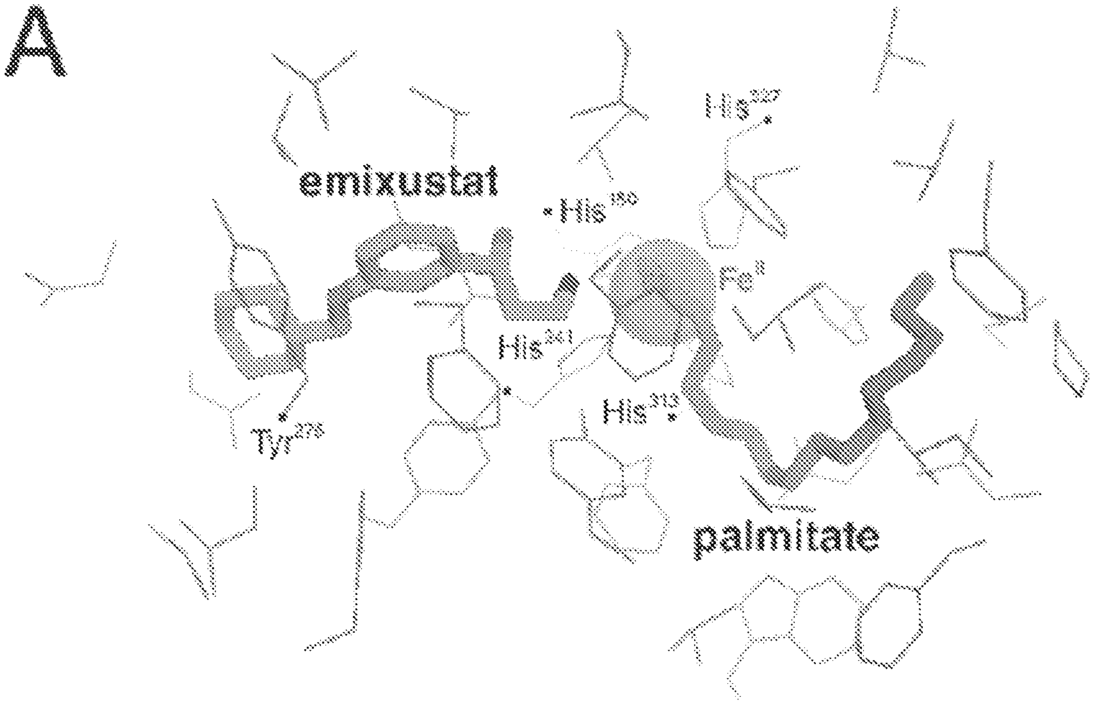
FIGS. 4(A-F) illustrate the crystal structures of bovine RPE65 in complex with A) emixustat (PDB accession code 4RSC) B) MB-004 (PDB accession code 5UL5), C)C-2'-fluoro-emixustat (compound 49), D)C-2'-fluoro-MB-004 (compound 24), E)C-5"-difluoro-emixustat (compound 57), and F) the detergent hexaoxyethylene monooctyl ethyl ($C_8E_6$). Inhibitors are shown as sticks (fluorine atoms colored), protein residue side chains within 4 Å of the ligands as slate-colored lines, the bound palmitate ligands as slate-colored sticks, and the iron ion as a sphere. The mesh represents unbiased sigma-A weighted $|F_o|-|F_c|$ electron density calculated following initial rigid body refinement and prior to modeling the ligand. The density map is contoured at 3 RMSD and shown within 3 Å of the corresponding ligand.
Figure 4B:
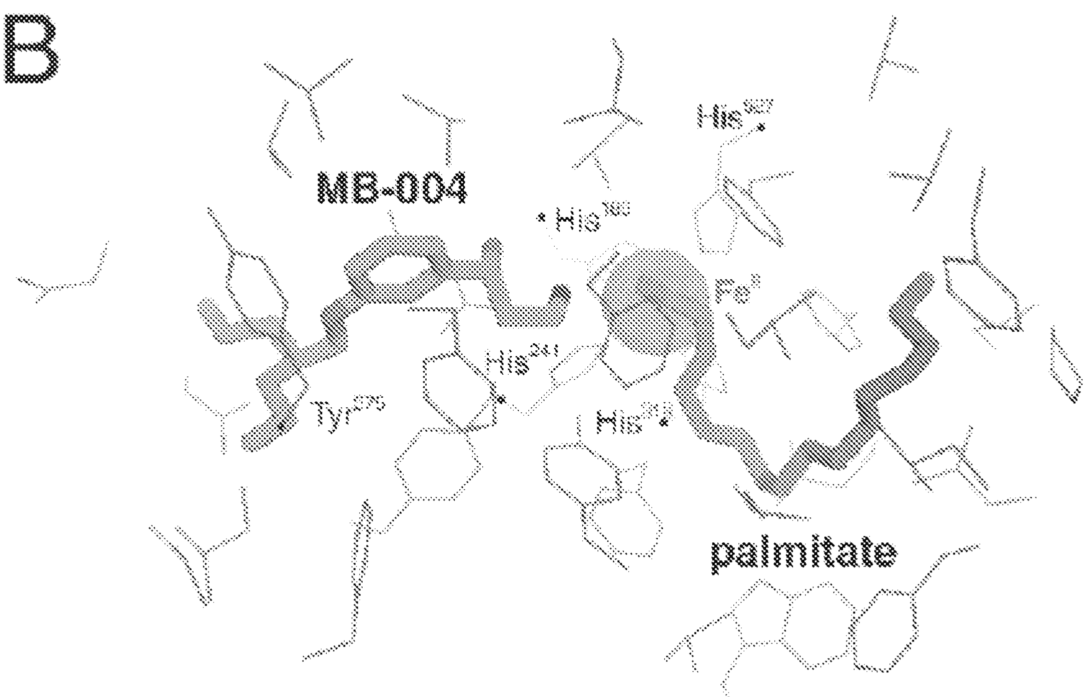
Figure 4C:
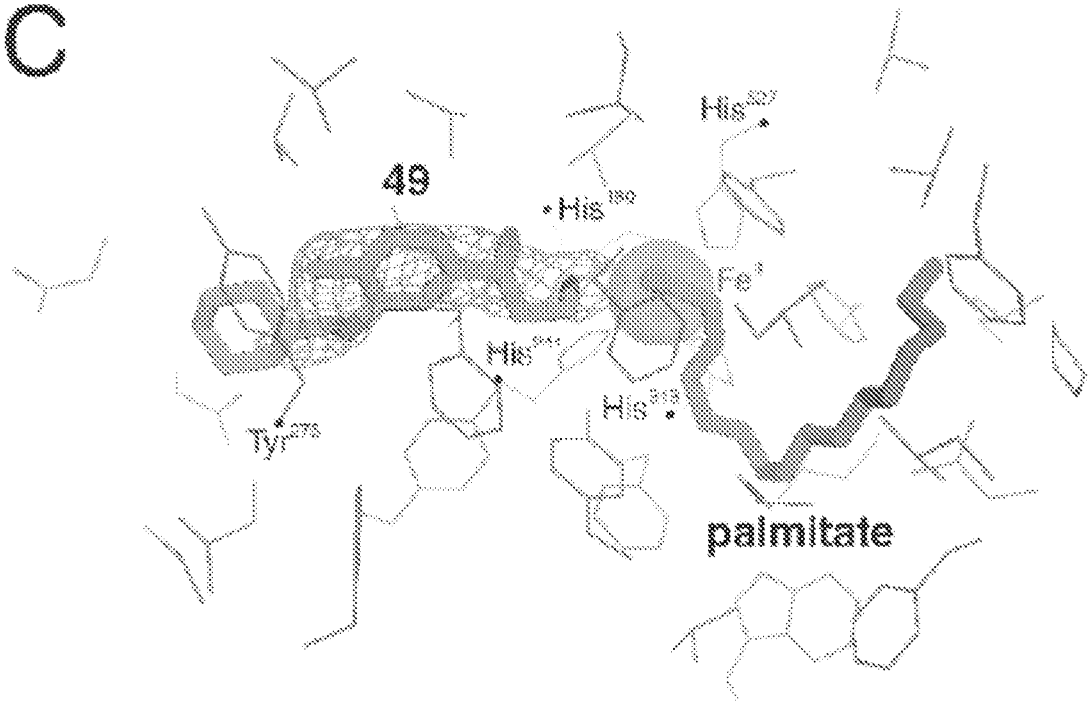
Figure 4D:
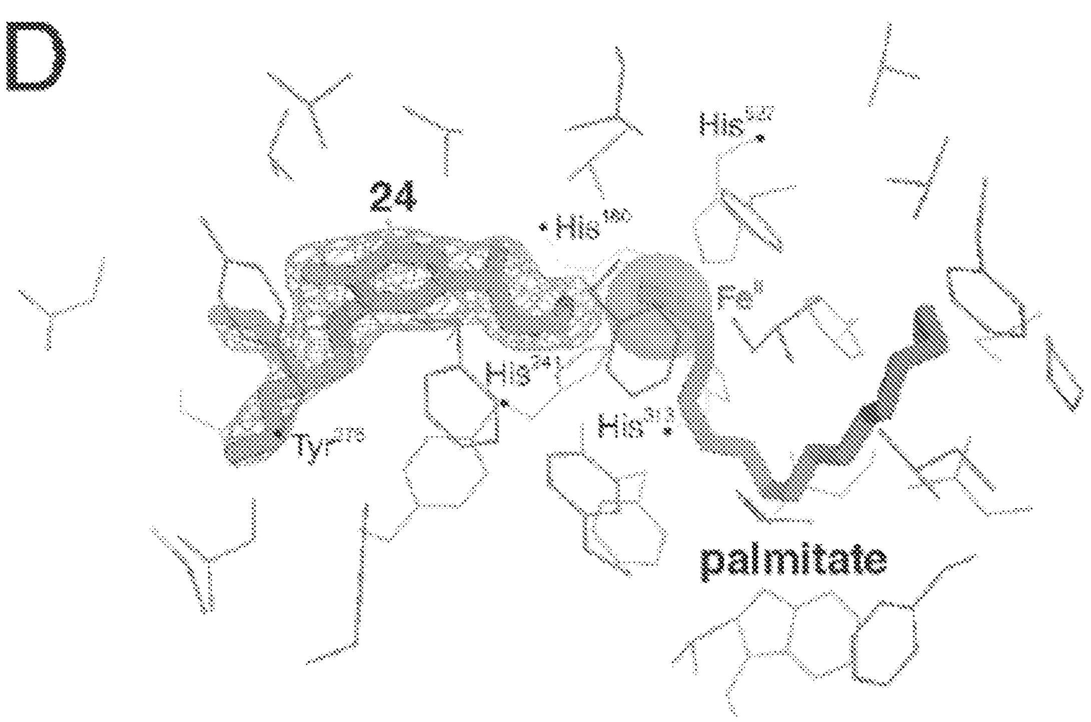
Figure 4E:
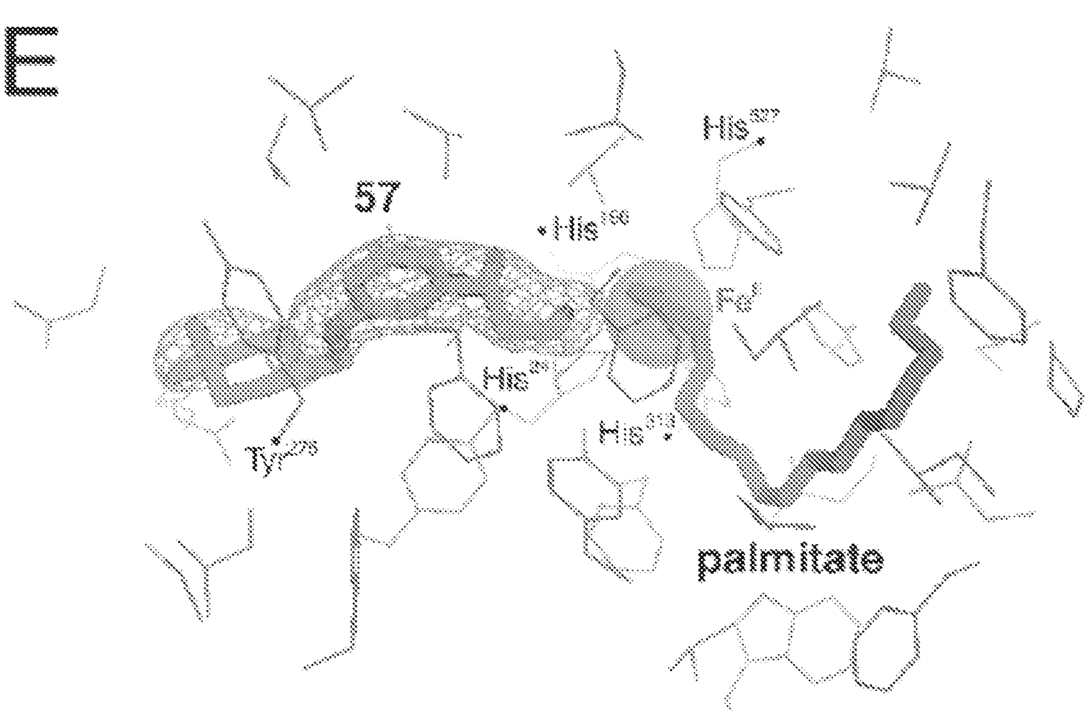
Figure 4F:
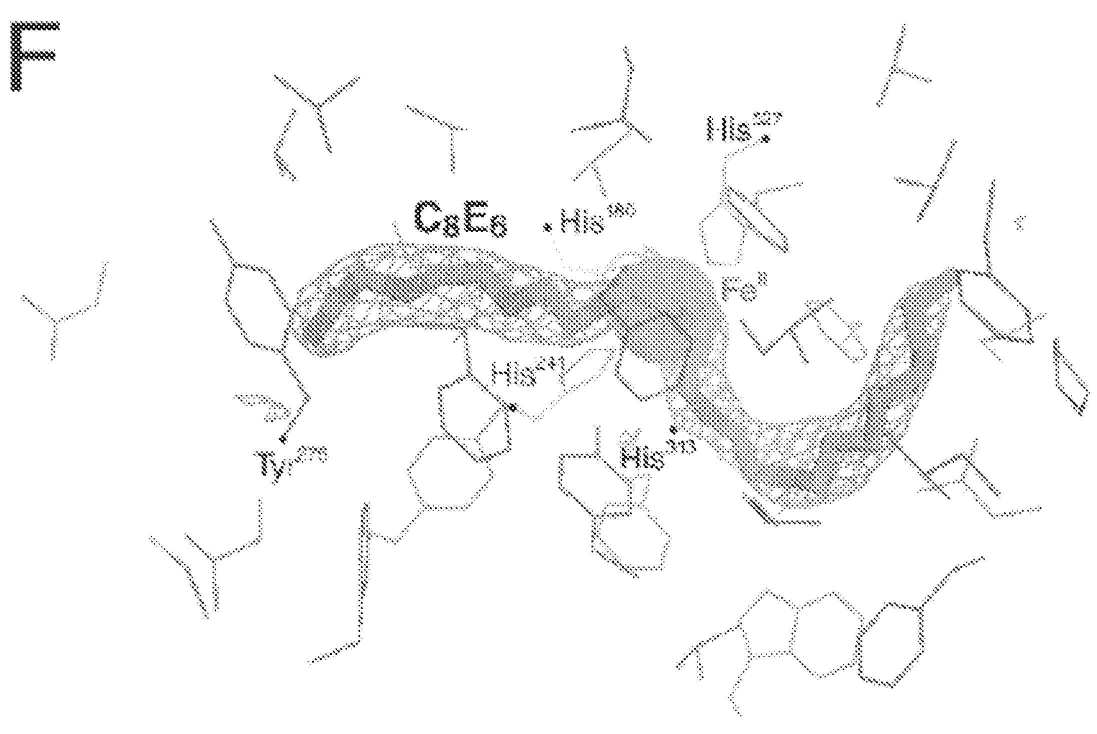
Figure 5A:
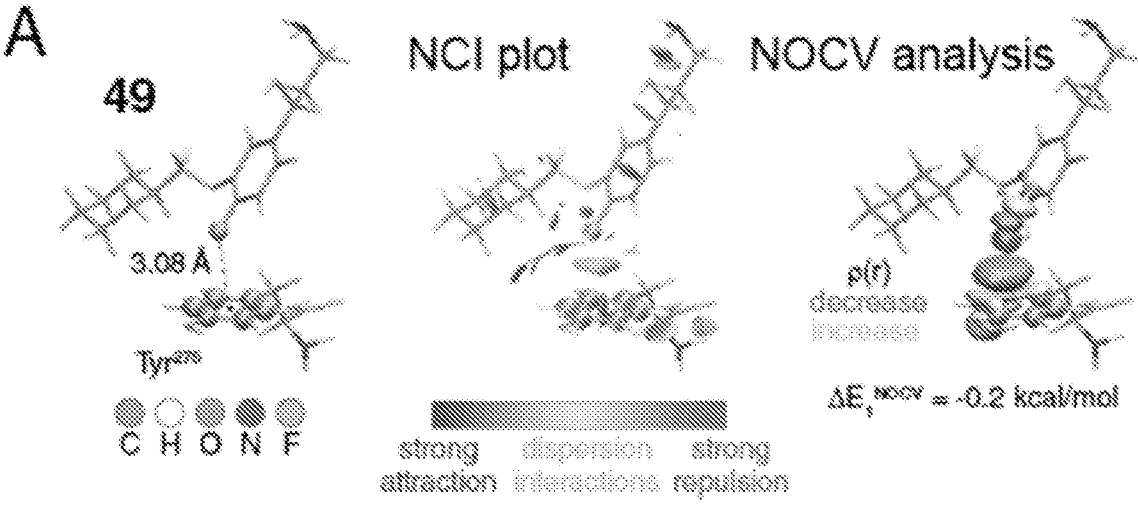
FIGS. 5(A-B) illustrate theoretical analyses of the interactions of compound 49 (A) and compound 24 (B) with $Tyr^{275}$, using a model dimer system. In both panels, the leftmost model under study is shown with the F·π distance highlighted. The next items depict outcomes of the two electron density analyses: non-covalent interaction (NCI) plots, and deformation densities obtained with natural orbitals for chemical valence (NOCV). The former shows regions in 3D space associated with various types of non-covalent interactions; the green arrow points to the F·π dispersion interaction (isovalue of s=0.6 a.u., colored according to $-0.035<\text{sign}(\lambda_2)\rho<0.02$). The isosurface plots (±0.005 a.u.) of the deformation densities are for pairs of NOCVs with significant interaction energies $\Delta E_n^{NOCV}$ (total computed NOCV orbital interaction energy is −0.7 and −2.4 kcal/mol for A and B models, respectively).
Figure 5B:
Figure 5B:
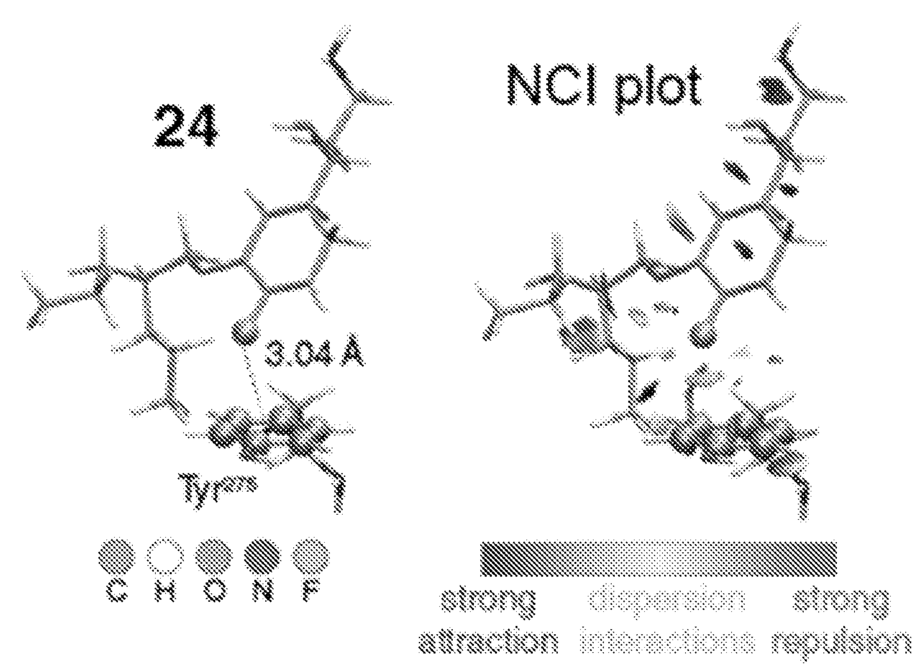
Figure 5B:
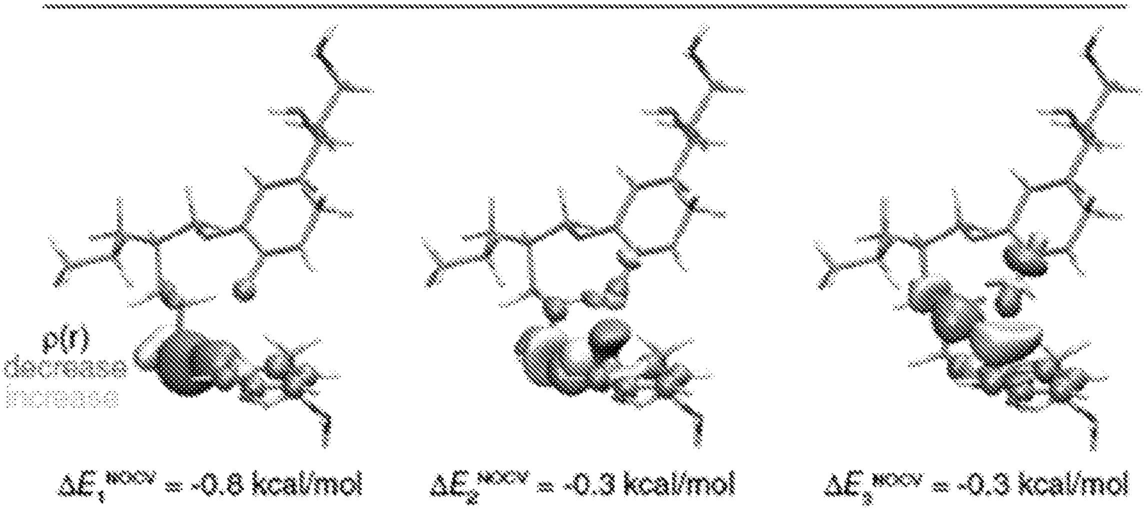

Oxidative deamination, and hydroxylation on the cyclohexyl ring are two pathways for emixustat elimination in vivo; the former being more dominant in the vasculature as compared to the liver. We explored this possibility by comparing the rate of oxidative deamination of emixustat and its α-deuterated derivative of emixustat (compound 58) in an HPLC-based activity assay using mouse aorta homogenates as the source of VAP-1 enzyme (FIG. 3A). We monitored formation of the dehydrated aldehyde product of VAP-1 catalysis (ACU-5201) by reversed phase HPLC (FIG. 3B) whose identity and absolute amount were determined by comparison to an authentic synthetic standard (FIGS. 3, B and C). As compared to emixustat, the formation of ACU-5201 from compound 58 was reduced by approximately 66% at both time points examined (FIG. 3D). This data is consistent with the idea that proton abstraction from the amine α-carbon is a rate-limiting step in the catalytic mechanism of emixustat deamination by VAP-1.

Figure 2A:
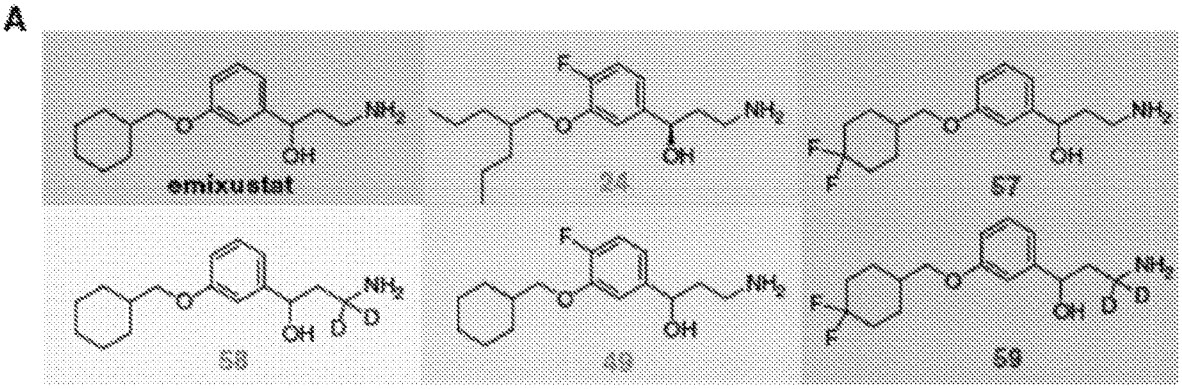
FIGS. 2(A-E) illustrate the inhibitory effects and pharmacokinetics of visual cycle modulators. A) Structures of visual cycle modulators used for pharmacokinetics studies. B) Evaluation of the inhibitory effects of selected visual cycle modulators on 11-cis-retinol production by bovine RPE microsomes. Racemic emixustat served as a positive control. The fluorinated compounds 24 ($IC_{50}$=50±9 nM), 49 ($IC_{50}$=95±5 nM) and 57 ($IC_{50}$=100±29 nM) showed superior inhibitory effects relative to unmodified emixustat ($IC_{50}$=172±29 nM) and the deuterated compound 58 ($IC_{50}$=191±15 nM). Data points are shown as mean±s.d.; n=3. C, D) Quantification of visual cycle modulator levels in mouse serum (C) and eyes (D). Eight week-old wild-type mice were treated with 380 nmol of each of the visual cycle modulators in DMSO through intraperitoneal injection, and sacrificed at 3 h, 1 day, or 7 day later. Then the primary amine levels in mouse serum and eyes were quantified with LC-MS/MS. Data points are shown as mean±s.d.; n=4-5. E) The primary amine levels in mouse eyes on day 7 after the treatments.
Figure 2B:
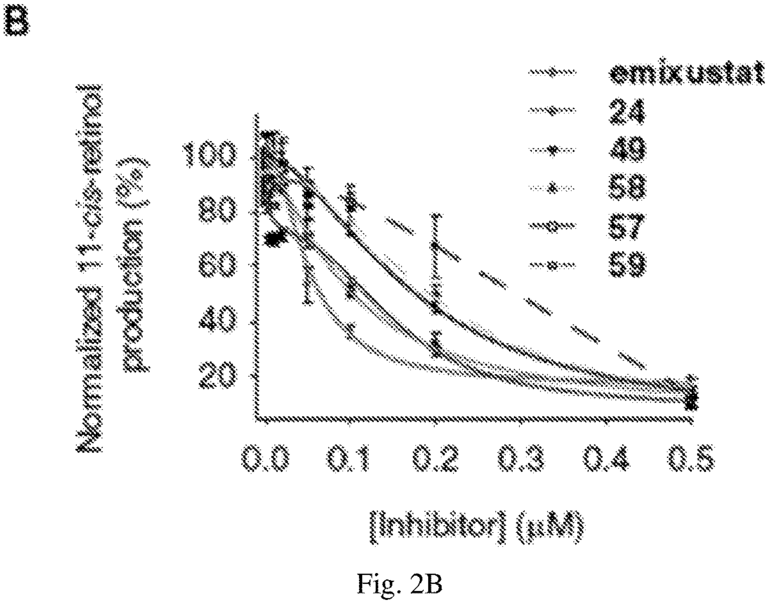

To investigate the impact of fluorination and deuteration on the elimination of emixustat in mouse eyes, a single dose of 380 nmol of emixustat, 24, 49, 57, 58 or 59 was individually administrated to wild type mice by intraperitoneal injection. The concentrations of the administered compounds found in mouse eyes were quantified by a mass spectrometry method (FIGS. 2A, D and E). Most compounds were monitored for the loss of a water (~18 Da) in the LC-MS/MS-ESI fragmentation spectra. An exception was 58, in which loss of a water plus a methylene imine (~47 Da) was monitored due to a high background effect of the fragmentation at minus 18.

Quantification was based on the area under the chromatographic peak for each compound, which accurately reflected the amount of each compound, with a coefficient of determination ($R^2$) above 0.999.

Figure 2C:
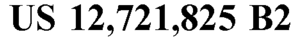
Figure 2C:
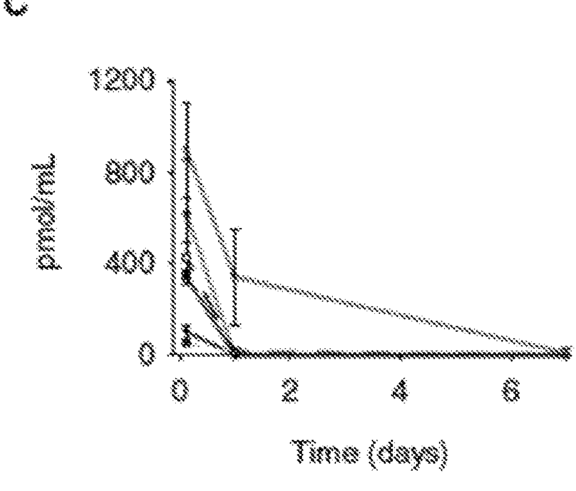
Figure 2D:
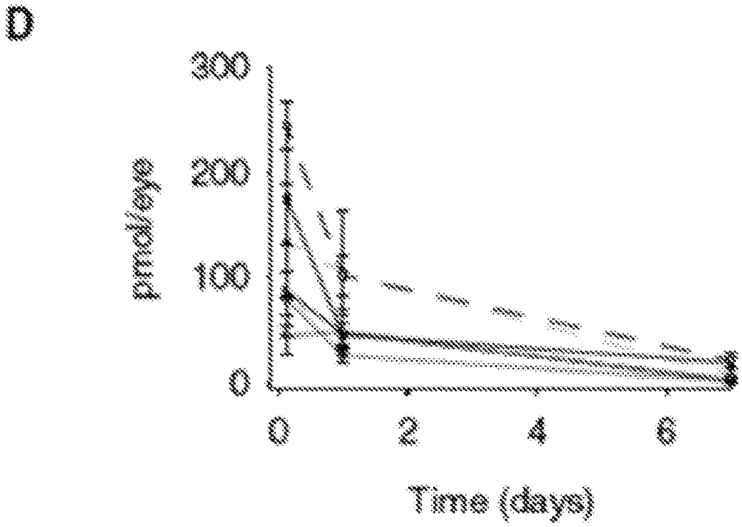
Figure 2E:
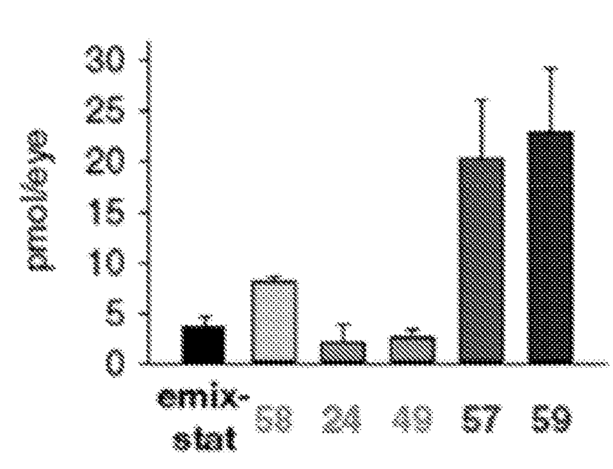

We first measured the total plasma concentrations of these compounds 3 h, 1 d, or 7 d after compound administration (FIG. 2C). Interestingly, we observed that compounds 24 and 49, which both contain a 2'-fluoro substituents, exhibited the highest initial plasma levels suggesting that this modification can deactivate elimination pathway(s) of relevance in mice. Unexpectedly, we observed that $^2H_2$-emixustat had an initial serum concentration comparable to that of emixustat, which suggests that VAP-1 may not be a major pathway of emixustat clearance in the mouse. At 1 d after injection all compounds besides 24 were below the limits of detection. The longer plasma half-life of compound 24 is likely due to its more flexible alkyl substituents, which may be less susceptible to oxidation.

Next, we measured the distribution and retention of these compounds into the mouse eye. Emixustat efficiently distributed to ocular tissue reaching 88±43 pmol/eye at 3 h after i.p. drug administration, nearly equal to 15% of the rhodopsin content in mouse eyes. 5"-gem-difluorination of the emixustat cyclohexyl (i.e., compound 57) further enhanced ocular distribution. Interestingly, we observed that compounds 24 and 49, which displayed the highest initial plasma concentrations, exhibited the poorest distribution within ocular tissue. These data point to a possible ocular uptake mechanism for emixustat that is disrupted by 2'-fluorination. Scrutiny of the mass spectra for 24 and 59 standards revealed that their peak intensities in methanol were much weaker than (about 5-10%) the peak intensities of emixustat and 57 standards in methanol at the same concentration. In the tandem mass spectra, 24 and 49 were also resistant to losing the methylene imine fragment. The difficulty of ionization and fragmentation of 24 and 49 in mass spectrometry imply that 2'-fluorination on the phenyl ring might intensify the intra-molecular N·H·O hydrogen bonding interaction and reduce the molecule flexibility to hamper drug delivery to the eye. In our previous studies, most drug candidates against light-induced retinal degeneration decayed to negligible levels just 24 h after a single-dose intraperitoneal injection. By contrast, emixustat and most of its fluorinated derivatives only moderately declined to around 50 pmol/eye during the same period, approximating 10% of the rhodopsin content. On day 7, the level of emixustat further dropped to about 4 pmol/eye, which is too low for all-trans-retinal sequestration, but still sufficient to inhibit RPE65 activity and visual chromophore recovery.

The level of deuterated emixustat, 58, in the eye was approximately two-fold higher than that of emixustat. In light of the plasma level data presented above we cannot attribute this elevation to high circulating concentrations favoring distribution into the ocular tissue. Instead, it is possible that deuteration could positively impact ocular drug retention or affect metabolism within the eye by as-yet undefined processes.

Crystal Structures of RPE65 in Complex with Fluorinated Visual Cycle Modulators

To gain an understanding of the factors underlying the enhanced potency of compounds 24, 49, and 57 compared to their parent molecules, we determined the crystal structures of RPE65 in complex with each of these compounds. The crystals were isomorphous to prior RPE65 structures in space group $P6_5$ and diffracted X-rays to resolutions of 1.95, 2.15, and 1.90 Å, respectively (Table 3). The structures were refined to overall $R_{free}$ values of 21.1%, 21.7%, and 20.1% with excellent geometrical and clash score statistics (Table 3). A 2.1 Å resolution structure of apo-RPE65 was also determined for comparison (Table 3). Unbiased residual maps obtained after the first rounds of refinement in the absence of modeled ligands revealed a clear $|F_o|-|F_c|$ density for the bound visual cycle modulators in the proximal active site region, including well-defined features corresponding to the fluoro substituents (FIG. 4). Residual electron density was also present in the distal cavity corresponding to a palmitate molecule forming a coordinate bond with the iron prosthetic group via its carboxylate moiety, consistent with prior findings. Electron density maps following the inclusion of the inhibitor ligand in the model showed a well-defined density for the aryl γ-hydroxypropylamine moiety in all cases. The β,β-dipropylethoxy group of 24 was similarly well defined whereas the densities for the cyclohexylmethoxy groups of 49 and 57 were comparatively much weaker (FIG. 4). The relative quality of the electron density support for these different moieties is consistent with prior studies on emixustat and MB-004. The crystal structure of apo-RPE65 featured an active site $|F_o|-|F_c|$ density consistent with hexaethylene glycol monooctyl ether ($C_8E_6$).

Linear detergents are known to inhibit the activity of RPE65, and related carotenoid oxygenase enzymes. The structure of apo-RPE65 solved with $C_8E_6$ bound to its active site provides evidence that such inhibition can be partially attributed to direct active site binding. Despite the high concentration of detergent in the crystallization mother liquor (>16 mM), compounds 24, 49, and 57 were able to outcompete the detergent for binding to the RPE65 active site consistent with their strong active site-binding affinities.

The binding modes for compounds 24, 49, and 57 largely overlap with those of MB-004 and emixustat with a few notable exceptions (FIG. 4). The binding mode of the aryl γ-hydroxypropylamine moiety of compound 57 was similar to that of emixustat (FIGS. 4, A and E), whereas its terminal ring was rotated by ~90° as evidenced by clear electron density for its gem-difluoro moiety. This change in cyclohexyl ring position was likely driven by fluorine-associated steric effects. Notably, a similar ring positioning was observed previously for emixustat in a $P6_522$ RPE65 crystal form (PDB accession code 4RYX). In this position, the gem-difluoro moiety engages in only a single van der Waals interaction with the $Asn^{194}$ side-chain oxygen atom. Although the bi-phasic $IC_{50}$ curve for 57 suggested two modes of RPE65 binding, we could not discern such behavior from the structural data, although it is notable that RPE65 is more poorly ordered near the active site opening in the structure of the RPE65-compound 57 complex as compared to the structure with emixustat bound. It is thus possible that multiple conformations, one of which has a higher affinity for 57, could be responsible for the bi-phasic inhibition results. In the case of 49, the C1'-O—C3-C2 dihedral angle is rotated by ~49° compared to the corresponding angle in emixustat, which is nearly planar. The analogous dihedral angle in 24 similarly deviates from the planarity seen in MB-004 by ~31°. These differences can be attributed to the presence of the nearby 4-fluoro group giving rise to two effects. First, the presence of the fluorine causes a ~0.4 Å downward shift in the binding position of the aryl ring, which may necessitate a corresponding rotation in the $C_3$—O bond to avoid steric clashes with the oxy-linked alkane moieties. Second, the rotation could also be driven by electrostatic effects between the electron-dense fluoro moiety and the lone pair electrons on the O-atom of the aryl ether. In addition, the structure of the enzyme-compound 24 complex revealed a conformational difference in one of the propyl groups of 24 as compared to the complex with MB-004.

The enzyme environment around the 4-fluoro substituent of the bound modulator is likely an important factor that could help explain the greater potency of the 4-fluoro compounds 24 and 49 compared to their parent molecules. The dominant interaction occurs with $Tyr^{275}$ where the fluoro group makes a close (~3-3.1 Å) enface contact with the aromatic ring. Compared to structures with the parent molecules bound, the $Tyr^{275}$ side-chain is rotated by ~8° around the Cβ-Cγ bond, likely to alleviate steric clashes with the fluoro moiety or to facilitate the en face interaction.

Quantum Chemical Analysis of the Aromatic-Fluoro Interaction Observed in Crystals To further elucidate the energetics of the aromatic-fluoro interaction observed in the crystal structures, we employed quantum chemistry calculations. One would expect the ~3 Å interaction to be repulsive in the first approximation as a highly electronegative F atom is brought in the close vicinity of an electron-rich π cloud. However, analogous stabilizing Cl·π dispersion-driven interactions are known in protein chemistry. Their strength is on the order of 2 kcal/mol and are thought to be dispersion-driven forces. In contrast, F·π contacts have not been investigated thoroughly. Experiments based on synthetic models provide estimates of the stabilizing interaction of roughly 1.6 kcal/mol. In recent work, Li and co-workers found that the stability of the F·π interaction increases with positive charge accumulation in the π-system. Thus, the interaction seems to be mostly electrostatically-driven.

Using dimer model systems obtained from the crystal structures (FIG. 5), we estimated the strength of the interaction ($\Delta E_{int}$) between $Tyr^{275}$ and each of the two fluorinated compounds 49 and 24 to be −2.34 and −2.69 kcal/mol, respectively, using the state-of-the-art DLPNO-CCSD(T) method at the basis set limit. The interaction energy was broken down into various contributions using the local energy decomposition (LED) scheme. According to Table 1, the overall electrostatic interaction has a repulsive characteristic ($\Delta E_{HF\text{-}CCSD}$(electro) >0). Here, key stabilizing factors within this contribution are the electrostatic attraction between 'prepared' wave-functions of the fragments $\Delta E_{HF}$ (elstat) and charge-transfer contributions $\Delta E_{CCSD}$(CT). Both are significantly more negative for compound 24. Within the latter, 24→Tyr double excitations have a significant contribution (÷3.70 kcal/mol). Overall repulsive electrostatic effects are compensated by the dispersion interactions $\Delta E_{CCSD}$(disp) of −4.28 and −8.23 kcal/mol for compounds 49 and 24, respectively. The magnitudes of $\Delta E_{HF}$(elstat) and $\Delta E_{CCSD}$(disp) are similar, thus both electrostatic and van der Waals forces are driving the examined interactions.

To further investigate the nature of the interaction between $Tyr^{275}$ and compounds 49 and 24 in 3D space we performed a non-covalent interaction (NCI) analysis (FIG. 5). Briefly, the NCI plot shows low-density and low-gradient regions that are associated with non-covalent interactions colored according to one of the components of the density Laplacian ($\lambda_2$): strong attractive interactions appear at $\lambda_2<0$ (e.g., H-bonds; blue in FIG. 5), while steric repulsion is associated with positive values of $\lambda_2$ (red in FIG. 5). Dispersion forces appear with small negative values around $\lambda_2\approx 0$ (green in FIG. 5). The examined systems' NCI plots revealed a significant dispersion interaction region in the middle between the F atom of both 24 and 49 and the π-plane of $Tyr^{275}$ (see FIG. 5). Another way to look at intermolecular interactions is to study natural orbitals for chemical valence (NOCV) within the density functional theory (DFT, here we used ωB97X-$D_3$BJ functional). Briefly, we start by considering isolated fragments 1 and 2 at the geometry of a dimer. The two are characterized with the electron densities $\rho_1$ and $\rho_2$, respectively. Simple union of these densities yields promolecular density $\rho^{pro}=\rho_1+\rho_2$ along with an associated promolecular wavefunction $\Psi^{pro}$. Self-consistent optimization of the latter provides $\Psi^{opt}$ with the optimal density $\rho^{opt}$. We then define deformation density $\Delta\rho$ as the difference between promolecular density and self-consistently converged density $\Delta\rho=\rho^{pro}-\rho^{opy}$. Eigenorbitals of the corresponding deformation density operator are called NOCVs and typical bonding and antibonding pairs are described with complementary NOCVs ($\varphi_{\pm n}$).

With each such pair, we associate the orbital deformation density $\Delta\rho^{orb}{}_n$:

$$\Delta\rho^{orb}{}_n=-v(\varphi_{-n})^2+v(\varphi_n)^2$$

where v is a corresponding NOCV eigenvalue. By using extended transition state theory (ETS), one assigns a particular energy portion to such orbital interaction. By summing up all NOCVs interaction energies, one obtains the so-called orbital-interaction energy. In the case of our dimers this yields ~0.7 and ~2.4 kcal/mol for 49 and 24, respectively. The orbital-interaction energies should be attributed mainly to electrostatic stabilization of the electron density in the dimers and less to dispersion. The latter is added a posteriori in our calculations and it does not influence the density distribution directly—total interaction energy (including dispersion correction) is ~2.3 kcal/mol for 49 and ~3.4 kcal/mol for 24. In this context, up to three significant NOCVs complementary pairs yield deformation densities shown in FIG. 5 that account for up to 60% of the orbital interaction energies in both cases. In the case of 24, the key ingredients are the interactions between the n-propyl chain and the $Tyr^{275}$ phenyl ring ($\Delta\rho^{orb}{}_1$, $\Delta\rho^{orb}{}_2$). The inspection of $\Delta\rho^{orb}{}_3$ shows that the region between the F atom and phenyl ring gains some electron density. At the same time, electron density reorganization takes place at both fragments within σ(C−F)/σ*(C−F)/n(F) and π(phenyl)/π*(phenyl) orbitals of 24 and $Tyr^{275}$, respectively. The electron density reorganization for 49 compared to 24 is less pronounced and is reflected in the overall diminished interaction energy.

TABLE 1

Local energy decomposition analysis of the DLPNO-CCSD(T) total interaction energy ($\Delta E_{int}$) in the crystal structure-derived dimers of compounds 49 or 24 with $Tyr^{275}$. All values are in kcal/mol

| ΔE [kcal/mol] | 49 | 24 |
|---|---|---|
| $\Delta E_{HF\text{-}CCSD}$(electro) | 1.87 | 5.80 |
| including: | | |
| $\Delta E_{HF}$(el-prep) | 8.46 | 27.11 |
| $\Delta E_{CCSD}$(el-prep) | 1.51 | 5.33 |
| $\Delta E_{HF}$(elstat) | −4.77 | −15.21 |
| $\Delta E_{HF}$(exch) | −1.58 | −5.71 |
| $\Delta E_{CCSD}$(CT EmixF → Tyr) | −1.58 | −3.70 |
| $\Delta E_{CCSD}$(CT Tyr → EmixF) | −0.17 | −2.02 |
| $\Delta E_{CCSD}$(disp) | −4.28 | −8.23 |
| ΔE(T) | −0.47 | −1.10 |
| ΔE(CBS) | 0.54 | 1.01 |
| $\Delta E_{int}$ | −2.34 | −2.69 |

CONCLUSIONS

Visual cycle modulation represents a critical therapeutic target with no currently approved drugs for the treatment of retinal diseases. Emixustat, a first-in-class visual cycle modulation drug candidate and inhibitor of the retinoid isomerase RPE65, has displayed promising in vitro and in vivo properties for the treatment of a variety of retinal diseases. Despite this, emixustat suffers from sub-optimal efficacy, problematic side effects, and rapid metabolism which cloud its clinical future.

A central goal of this example was to investigate whether fluorination and/or deuteration of emixustat could overcome some of the pharmacokinetic shortcomings of this clinical candidate. To accomplish this goal, we developed novel synthetic approaches to produce specific chiral products as emixustat inhibitory activity towards RPE65 was previously shown to depend on the C1 stereochemistry. The clear advance we present here in terms of chemical methodology is the introduction of an advanced three-component Mannich reaction utilizing (S)-(−)-α-methylbenzylamine to produce the desired stereoisomer. In this reaction scheme, the resultant from subsequent reduction step γ-hydroxypropylaminobenzyl product(s) consists of a mixture of diastereomers that can be carbamylated and separated using conventional flash column chromatography on silica gel as opposed to chiral chromatography required for separation of the parent enantiomers. Facile hydrolysis of the carbamate succeeding by debenzylation regenerates the key γ-hydroxypropylamine framework with the defined stereochemistry. This method thus provides clear advantages in terms of cost and scalability over chiral separation methods and perhaps can extend to other similar compounds.

We investigated the impact of these compounds on RPE65 activity in vitro and in live mice. Our first observation from these studies was that RPE65 inhibition does not correlate with accumulation in the eye. Two additional mechanisms for eye accumulation could include prolonging metabolic stability or selective uptake and/or retention by an as-yet undefined ocular components. In comparing emixustat to its deuterated derivative (58), and 57 to 59 it is clear that metabolic stability plays at least some role in this process. When the hydrogens at C-3 are replaced with deuterium, accumulation in the eye is increased at a level that is roughly proportional to the attenuation of VAP-1 oxidation.

The metabolism of primary amine drugs by VAP-1 is a lesser known phase 1 metabolic pathway, but has nevertheless been shown important for primary amine oxidation of clinically used drugs including primaquine and tresperimus in addition to emixustat. The results we present here suggest that deuteration of primary amines susceptible to VAP-1 oxidation could be a generally effective approach to prolonging their in vivo lifespan. The impact of alpha deuterium substitution of amines on VAP-1 metabolic susceptibility was previously studied in vitro using benzylamine and various phenylethylamines as test substrates. In the case of benzylamine, a large kinetic isotope effect was observed for ($k_{cat}/K_m$) but not for $k_{cat}$ which was interpreted as arising from a combined effect of deuteration on several isotopically-sensitive steps of the reaction mechanism. By contrast, a variety of para-substituted phenylethylamines, whose amine protons are in an environment similar to those of emixustat, all displayed kinetic isotope effects on $k_{cat}$ of ~5-8, which is within the theoretically expected primary kinetic isotope effect (i.e., KIE=3-7), expected for a reaction with a rate-limiting proton abstraction step. Our data showing impaired oxidation of deuterated emixustat as compared to emixustat is consistent with hydrogen abstraction being at least partially rate-limiting step in the mechanism of emixustat oxidation by VAP-1.

The structure-activity relationships that we observed in this study are largely consistent with previous observations including higher inhibitory activity for the R- vs S-isomer of the γ-aminoalcohol (Table 2, compare 24 to 23), as well as compounds with a β,β-dipropylethoxy substituent as opposed to a cyclohexyl or β-ionone moiety. Our structural biology results support our previous findings that the β,β-dipropylethoxy group can engage binding pockets within the RPE65 active site cavity that are not accessible to a cyclohexyl group, which likely improves the binding affinity of these compounds. In the present study, we expand the known SAR of RPE65 inhibitors to include the effects of fluorine substitution throughout the base structures of emixustat, MB-001 and MB-004. In general, we found that fluorine substitution on the aryl moiety could have either a positive or negative impact on inhibitory activity. A notable instance of a favorable impact was noted for the 2-fluoro derivative of MB-004 (compound 24) which exhibited an $IC_{50}$ value (50 nM) approximately two-fold lower than MB-004. A similar improvement in binding affinity was noted for 2'-fluoro-emixustat (49) as compared to emixustat. Structurally, the enhanced affinity appears to result from an energetically favorable interaction between the fluoro substituent and an active site tyrosyl side chain ($Tyr^{275}$). This finding is an interesting example of apparently favorable F·π interactions that have recently been described in the literature. Our electronic structure calculations suggest that the favorable interaction is dominated by van der Waals contributions as opposed to electrostatic interactions consistent with the electron rich nature of the phenolic side chain.

TABLE 2

Inhibition of the RPE65-mediated isomerization reaction[a]

| # | Inhibitor | Structure | $IC_{50}$ ± SD (nM) |
|---|---|---|---|
| 1 | Racemic-emixustat | 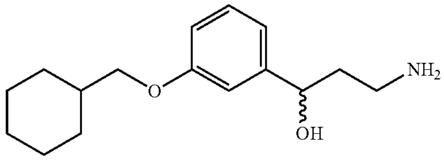 [SMILES: NCCC(O)c1cccc(OCC2CCCCC2)c1] | 172 ± 29 |
| 2 | (R)-MB-001 | 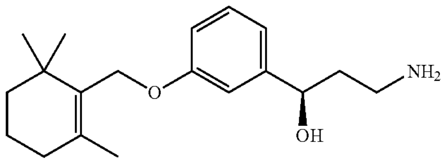 [SMILES: CC1=C(COc2cccc([C@H](O)CCN)c2)C(C)(C)CCC1] | 323 ± 145 |
| 3 | 24 | 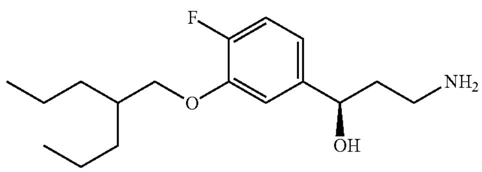 [SMILES: CCCC(CCC)COc1cc([C@H](O)CCN)ccc1F] | 50 ± 9 |

TABLE 2-continued
| Inhibition of the RPE65-mediated isomerization reaction[a] | | | |
|---|---|---|---|
| # | Inhibitor | Structure | $IC_{50} \pm SD$ (nM) |
| 4 | 49 | 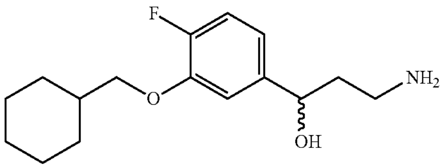 [SMILES: NCCC(O)c1ccc(F)c(OCC2CCCCC2)c1] | 95 ± 5 |
| 5 | 57 | 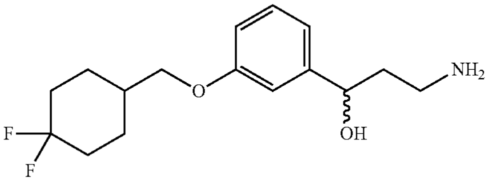 [SMILES: NCCC(O)c1cccc(OCC2CCC(F)(F)CC2)c1] | 103 ± 29 |
| 6 | 55 | 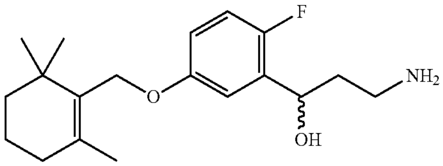 [SMILES: CC1=C(COc2ccc(F)c(C(O)CCN)c2)C(C)(C)CCC1] | 124 ± 21 |
| 7 | 28 | 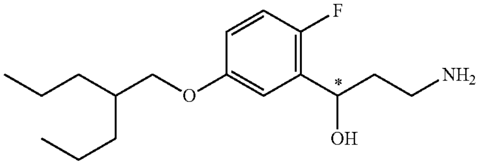 [SMILES: CCCC(CCC)COc1ccc(F)c(C(O)CCN)c1] | 132 ± 19 |
| 8 | 51 | 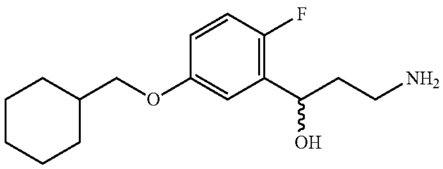 [SMILES: NCCC(O)c1cc(OCC2CCCCC2)ccc1F] | 145 ± 9 |
| 9 | 27 | 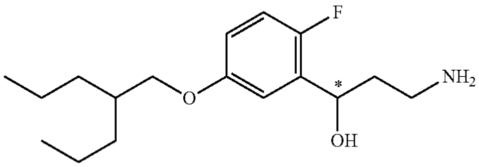 [SMILES: CCCC(CCC)COc1ccc(F)c(C(O)CCN)c1] | 157 ± 24 |
| 10 | 56 | 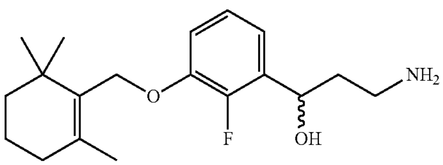 [SMILES: CC1=C(COc2cccc(C(O)CCN)c2F)C(C)(C)CCC1] | 169 ± 13 |
| 11 | 23 | 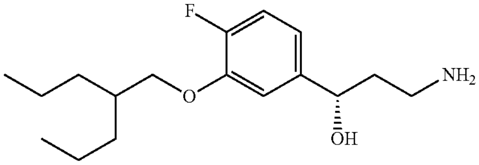 [SMILES: CCCC(CCC)COc1cc([C@@H](O)CCN)ccc1F] | 177 ± 11 |

TABLE 2-continued
| Inhibition of the RPE65-mediated isomerization reaction[a] | | | |
|---|---|---|---|
| # | Inhibitor | Structure | $IC_{50}$ ± SD (nM) |
| 12 | 26 | 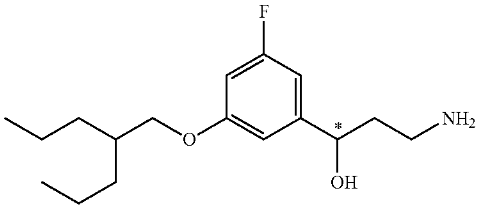 [SMILES: CCCC(CCC)COc1cc(F)cc(C(O)CCN)c1] | 184 ± 24 |
| 13 | 58 | 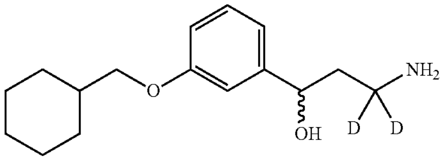 [SMILES: [2H]C([2H])(N)CC(O)c1cccc(OCC2CCCCC2)c1] | 190 ± 15 |
| 14 | 50 | 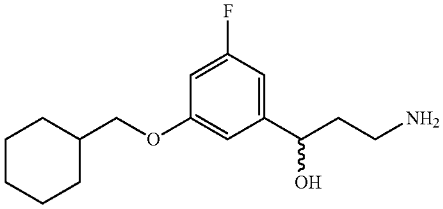 [SMILES: NCCC(O)c1cc(F)cc(OCC2CCCCC2)c1] | 201 ± 23 |
| 15 | 59 | 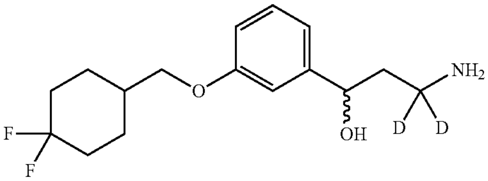 [SMILES: [2H]C([2H])(N)CC(O)c1cccc(OCC2CCC(F)(F)CC2)c1] | 269 ± 40 |
| 16 | 30 | 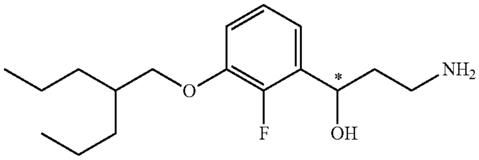 [SMILES: CCCC(CCC)COc1cccc(C(O)CCN)c1F] | 274 ± 47 |
| 17 | 53 | 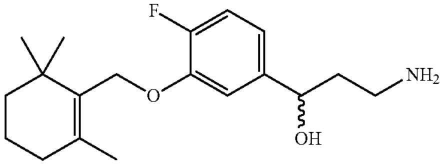 [SMILES: CC1=C(COc2cc(C(O)CCN)ccc2F)C(C)(C)CCC1] | 284 ± 20 |
| 18 | 29 | 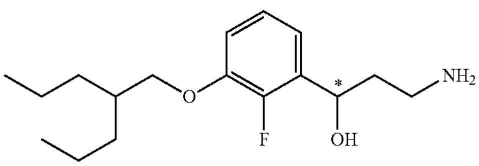 [SMILES: CCCC(CCC)COc1cccc(C(O)CCN)c1F] | 287 ± 283 |
| 19 | 54 | 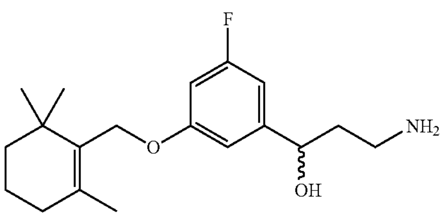 [SMILES: CC1=C(COc2cc(F)cc(C(O)CCN)c2)C(C)(C)CCC1] | 292 ± 89 |

TABLE 2-continued

Inhibition of the RPE65-mediated isomerization reaction[a]

| # | Inhibitor | Structure | $IC_{50}$ ± SD (nM) |
|---|---|---|---|
| 20 | 25 | 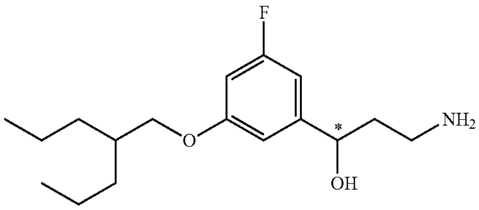 [SMILES: CCCC(CCC)COc1cc(F)cc(C(O)CCN)c1] | 295 ± 132 |
| 21 | 52 | 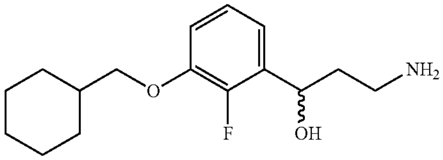 [SMILES: NCCC(O)c1cccc(OCC2CCCCC2)c1F] | 358 ± 42 |

[a]All of the compounds were tested as described in the methods section, "RPE65 retinoid isomerase activity assay." Inhibition of RPE65 enzymatic activity was measured as a decline in 11-cis-retinol production.

Asterisks denote compounds with chiral centers that were synthesized and chirally separated, but their chirality was not determined.

TABLE 3

X-ray data collection, processing and refinement

Data collection and processing

| Crystal | RPE65 $C_8E_6$ | RPE65 49 | RPE65 23 | RPE65 57 |
|---|---|---|---|---|
| X-ray source | NSLS-II FMX 17-ID-2 | SSRL 12-2 | NSLS-II FMX 17-ID-2 | APS NE-CAT 24-ID-E |
| Wavelength (Å) | 0.979300 | 0.979460 | 0.979358 | 0.979180 |
| Space group | $P6_5$ | $P6_5$ | $P6_5$ | $P6_5$ |
| Unit cell lengths (Å) | a = 175.92, c = 86.31 | a = 175.69, c = 86.21 | a = 175.51, c = 86.66 | a = 175.43, c = 86.67 |
| Resolution (Å)† | 50-2.1 (2.23-2.10) | 50-2.15 (2.28-2.15) | 50-1.95 (2.07-1.95) | 50-1.90 (2.02-1.90) |
| Unique reflections | 88,260 (14,309) | 82,432 (13,267) | 110,605 (17,591) | 118,471 (19,003) |
| Multiplicity | 5.2 (5.4) | 6.8 (6.8) | 10.4 (9.8) | 10.4 (10.5) |
| Completeness (%) | 99.4 (99.7) | 99.9 (99.7) | 99.7 (98.4) | 99.7 (99.5) |
| <I/σI> | 8.3 (0.9) | 9.8 (1.1) | 11.0 (1.0) | 13.1 (0.96) |
| $R_{merge}$I (%) | 11.6 (170.3) | 16.6 (176.7) | 16.3 (234.6) | 11.3 (248.2) |
| $CC_{1/2}$ (%) | 99.6 (37.3) | 99.6 (40.8) | 99.8 (46.3) | 99.9 (43.0) |
| Wilson B factor ($Å^2$) | 51 | 46 | 40 | 45 |
| **Refinement** | | | | |
| Resolution (Å) | 47.9-2.1 | 47.8-2.15 | 47.9-1.95 | 47.9-1.90 |
| No reflections‡ | 83,735 (4,523) | 78,245 (4,187) | 104,965 (5,639) | 112,436 (6,033) |
| $R_{work}/R_{free}$ (%) | 18.9/22.0 | 18.9/21.7 | 19.5/21.1 | 17.7/20.1 |
| No atoms⁋ | 9,011 | 9,204 | 9,220 | 9,205 |
| Protein | 8,148 | 8,292 | 8,253 | 8,276 |
| Metal | 2 | 2 | 2 | 2 |
| Water | 787 | 800 | 851 | 844 |
| Ligand | 54 C86 | 40 W4J/ 36 PLM | 42 W9A/ 72 PLM | 42 XQ7/ 36 PLM |
| <B-factor> ($Å^2$) | 52.7 | 44.0 | 39.4 | 47.3 |
| Protein | 51.9 | 43.0 | 38.4 | 46.0 |
| Metal | 42.9 | 34 | 29.3 | 36.5 |
| Water | 59.2 | 50.6 | 49.1 | 57.0 |
| Ligand | 64.2 C86 | 71.6 W4J/ 56.7 PLM | 51.8 W9A/ 48.8 PLM | 73.8 XQ7/ 62.4 PLM |
| RMS deviations | | | | |
| Bond lengths (Å) | 0.003 | 0.002 | 0.002 | 0.003 |
| Bond angles (°) | 1.2 | 1.2 | 1.2 | 1.2 |
| Ramachandran plot (% favored/outliers)* | 97.2/0 | 98.2/0 | 97.7/0 | 97.8/0 |

TABLE 3-continued

| X-ray data collection, processing and refinement Data collection and processing | | | | |
|---|---|---|---|---|
| Molprobity score (%) | 100th | 100th | 100th | 100th |
| PDB accession code | 7K88 | 7K89 | 7K8G | 7L0E |

†Values in parentheses are for the highest resolution shell of data
‡Values in parentheses indicate the number of reflections used for cross-validation
*Evaluated using Molprobity[6]

TABLE 4

| Detection of primary amines with mass spectrometry | | | | |
|---|---|---|---|---|
| | Retention Time (min) | Precursor ion (m/z) | Daughter ion (m/z) | Capillary Temperature (° C.) |
| Emixustat | 7.67 | 264.1 | 246.0 | 275 |
| 58 | 7.67 | 266.1 | 217.1 | 275 |
| 49 | 7.73 | 282.2 | 264.0 | 350 |
| 24 | 8.62 | 298.2 | 280.0 | 350 |
| 57 | 7.17 | 300.2 | 282.1 | 275 |
| 59 | 7.17 | 302.1 | 284.0 | 275 |

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of treating an ocular disorder in a subject in need thereof, the method comprising:

administering to the subject a therapeutically effective amount of a compound of formula (II):

(II)

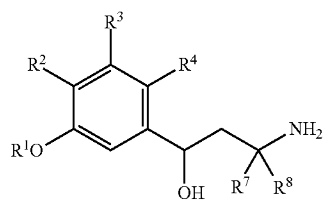

or a pharmaceutically acceptable salt, tautomer, or solvate thereof;

where $R^1$ is a substituted or unsubstituted $C_1$-$C_{12}$ alkyl, $C_2$-$C_{12}$ alkenyl, $C_2$-$C_{12}$ alkynyl, $C_3$-$C_{12}$ aryl, heteroaryl, heterocyclyl, or $C_6$-$C_{12}$ alkaryl;

$R^2$ is H or F;

$R^3$ and $R^4$ are each H; and $R^7$ and $R^8$ are H or D, wherein both of $R^7$ and $R^8$ are D if $R^2$ is H;

wherein the ocular disorder comprises at least one of light induced retinal degeneration, macular degeneration, Stargardt's disease, geographic atrophy, and retinitis pigmentosa.

2. The method of claim 1, wherein at least one of $R^7$ or $R^8$ is D.

3. The method of claim 1, wherein both of $R^7$ and $R^8$ are D.

4. The method of claim 1, wherein $R^2$ is F.

5. The method of claim 1, wherein $R^1$ is selected from the group consisting of:

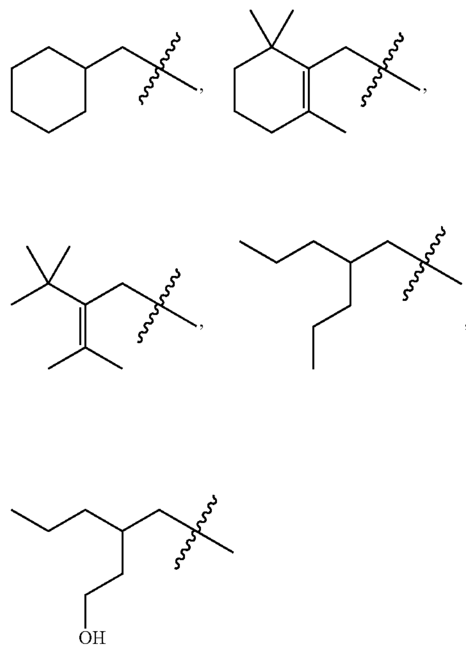

and fluoro derivatives thereof.

6. The method of claim 1, wherein $R^1$ is selected from the group consisting of:

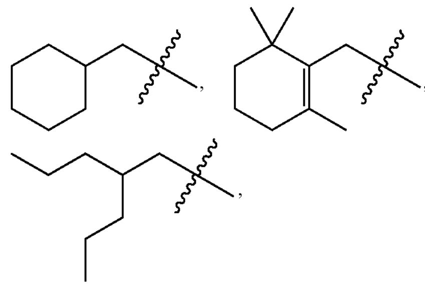

and fluoro derivatives thereof.

7. A method of treating an ocular disorder in a subject in need thereof, the method comprising:

administering to the subject a therapeutically effective amount of a compound of formula (IV):

(IV)

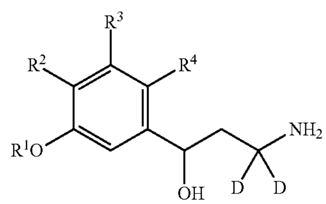

or a pharmaceutically acceptable salt, tautomer, or solvate thereof;

wherein $R^1$ is a substituted or unsubstituted $C_1$-$C_{12}$ alkyl, $C_2$-$C_{12}$ alkenyl, $C_2$-$C_{12}$ alkynyl, $C_5$-$C_{12}$ aryl, heteroaryl, heterocyclyl, or $C_6$-$C_{12}$ alkaryl;

$R^2$ is H or F;

$R^3$ and $R^4$ are H; and wherein the ocular disorder comprises at least one of light induced retinal degeneration, macular degeneration, Stargardt's disease, geographic atrophy, and retinitis pigmentosa.

8. The method of claim 7, wherein $R^2$ is F.

9. The method of claim 7, wherein $R^1$ is selected from the group consisting of:

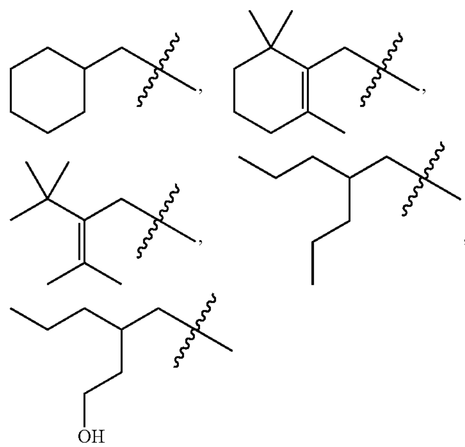

and fluoro derivatives thereof.

10. The method of claim 7, wherein $R^1$ is selected from the group consisting of:

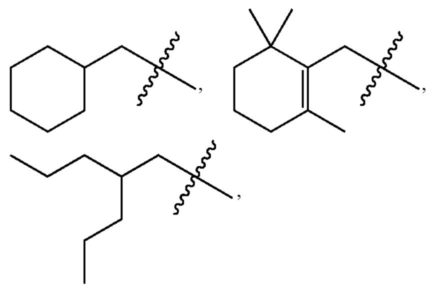

and fluoro derivatives thereof.

11. A method of treating an ocular disorder in a subject in need thereof, the method comprising:

administering to the subject a therapeutically effective amount of a compound selected from:

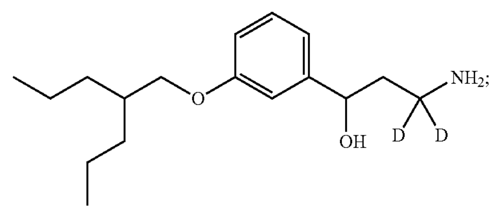

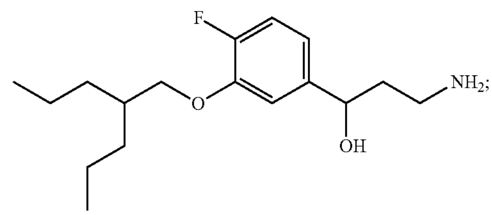

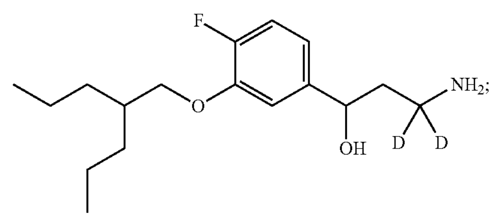

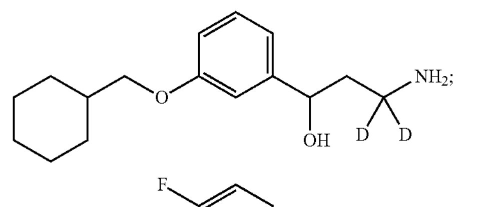

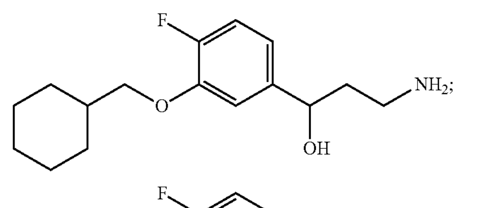

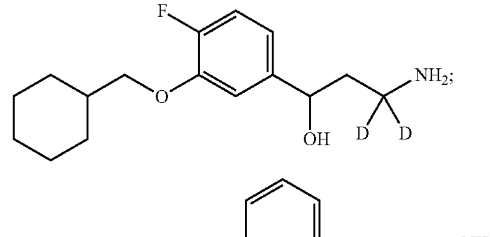

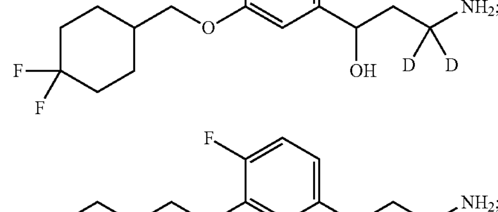

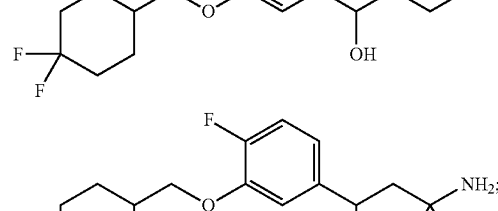

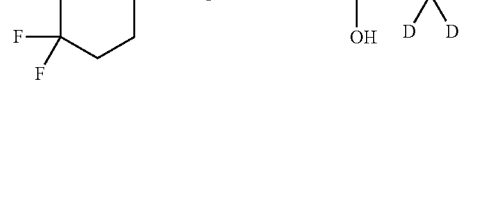

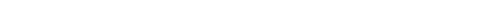

-continued

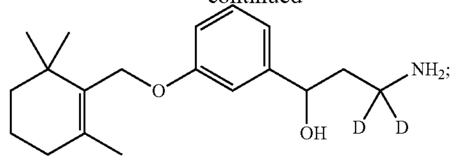

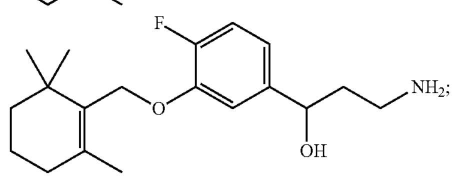

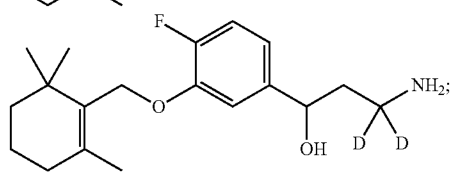

or a pharmaceutically acceptable salt, tautomer, or solvate thereof, wherein the ocular disorder comprises at least one of light induced retinal degeneration, macular degeneration, Stargardt's disease, geographic atrophy, and retinitis pigmentosa.

12. The method of claim 1, the compound being delivered to the subject by at least one of topical administration, systemic administration, intravitreal injection, and intraocular delivery.

* * * * *